US012344875B2

(12) United States Patent
Beauprez et al.

(10) Patent No.: US 12,344,875 B2
(45) Date of Patent: Jul. 1, 2025

(54) SIALYLTRANSFERASES FOR THE PRODUCTION OF SIALYLATED OLIGOSACCHARIDES

(71) Applicant: INBIOSE N.V., Zwijnaarde (BE)

(72) Inventors: Joeri Beauprez, Zwijnaarde (BE); Thomas Decoene, Zwijnaarde (BE); Annelies Vercauteren, Zwijnaarde (BE); Tom Verhaeghe, Zwijnaarde (BE)

(73) Assignee: INBIOSE N.V., Zwijnaarde (BE)

( * ) Notice: Subject to any disclaimer, the term of this patent is extended or adjusted under 35 U.S.C. 154(b) by 0 days.

(21) Appl. No.: 18/847,017

(22) PCT Filed: Mar. 30, 2023

(86) PCT No.: PCT/EP2023/058392
§ 371 (c)(1),
(2) Date: Sep. 13, 2024

(87) PCT Pub. No.: WO2023/187109
PCT Pub. Date: Oct. 5, 2023

(65) Prior Publication Data
US 2025/0109419 A1   Apr. 3, 2025

(30) Foreign Application Priority Data

Apr. 1, 2022  (EP) ..................... 22166399
Apr. 1, 2022  (LU) ........................ 501775
Jan. 16, 2023  (EP) ..................... 23151744

(51) Int. Cl.
*C12P 19/18*     (2006.01)
*C12N 9/10*      (2006.01)
*C12P 19/04*     (2006.01)

(52) U.S. Cl.
CPC ............ *C12P 19/04* (2013.01); *C12N 9/1081* (2013.01); *C12P 19/18* (2013.01); *C12Y 204/99* (2013.01)

(58) Field of Classification Search
None
See application file for complete search history.

(56) References Cited

FOREIGN PATENT DOCUMENTS

| EP | 3789495 A1 | 3/2021 |
|----|------------|--------|
| WO | 2014/153253 A1 | 9/2014 |
| WO | 2019/020707 A1 | 1/2019 |
| WO | 2021/123113 A1 | 6/2021 |
| WO | 2022/034080 A1 | 2/2022 |

OTHER PUBLICATIONS

Li et al., "Sialic acid metabolism and sialyltransferases: natural functions and applications," Appl. Microbiol. Biotechnol. 94:887-905, 2012 (Year: 2012).*

Bozue J A et al, "Heamophilus Ducreyi Produces a Novel Sialyltransferase Identification of the Sialyltransferase Gene and Construction of Mutants Deficient in the Production of the Sialic Acid-Containing Glycoform of the Lipooligosaccharide", Journal of Biological Chemistry, American Society For Biochemistry and Molecular Biology, vol. 274, No. 7, Feb. 12, 1999, pp. 4106-4114.
Chaffin D et al, "CpsK of *Streptococcus agalactiae* exhibits alpha2,3-sialyltransferase activity in Haemophilus ducreyi," Molecular Microbiology, vol. 45, No. 1, Jul. 1, 2002, pp. 109-122.
Cieslewicz et al., "Structural and Genetic Diversity of Group B *Streptococcus* Capsular Polysaccharides," Infection and Immunity, vol. 73, No. 5, May 1, 2005, pp. 3096-3103.
Coutinho et al., "An Evolving Hierarchical Family Classification for Glycosyltransferases," Journal of Molecular Biology, vol. 328, No. 2, Apr. 25, 2003, pp. 307-317.
Coutinho et al., "An evolving hierarchical family classification for glycosyltransferases," J Mol Biol, vol. 328, Issue 2, 2003, pp. 307-317, Accession No. WP_075099170.
Coutinho et al., "An evolving hierarchical family classification for glycosyltransferases," J Mol Biol, vol. 328, Issue 2, 2003, pp. 307-317, Accession No. WP_075099170. Accession No. WP_076996443.
Database UniProt [Online] Oct. 10, 2018, "RecName: Full=Sialyltransferase PMO188 {ECO:00002561Google: ProtNLM};", XP002809607, retrieved from EBI accession No. UNIPROT:A0A328BV32 Database accession No. A0A328BV32.
Database UniProt [Online] Oct. 11, 2004, "SubName: Full=Cps7K {ECO:00003131EMBL:AAR25954.I};", XP002807886, retrieved from EBI accession No. UNIPROT:Q67A31 Database accession No. Q67A31.
Database UniProt Jun. 1, 2001, "SubName: Full=Capsular biosynthesis protein {ECO:00003131EMBL:RDY91295. I}; SubName: Full=CpsK {ECO:00003131EMBL:ABD95546.I}; SubName: Full=CpsVK {ECO:00003131EMBL: AAK29659.I}; SubName: Full=Polysaccharide biosynthesis protein CpsK {ECO:00003131EMBL:AKI95574.I};", XP002807885, retrieved from EBI accession No. UNIPROT:Q9AFH2 Database accession No. Q9AFH2.
Database, UDP-N-acetylglucosamine 2-epimerase [Algoriphagus Sanaruensis], Aug. 23, 2021, Database accession No. WP_067548943.
Database, "Uncharacterized protein," Sep. 12, 2018, Database accession No. A0A2W5K627.

(Continued)

*Primary Examiner* — David Steadman
(74) *Attorney, Agent, or Firm* — TraskBritt

(57) ABSTRACT

The present invention is in the technical field of synthetic biology, metabolic engineering and cell cultivation. The present invention relates to newly identified sialyltransferases having alpha-2,3-sialyltransferase activity on the galactose residue of lactose. The invention also describes methods for the production of a 3'sialylated oligosaccharide using any one of the newly identified sialyltransferases as well as the purification of the 3'sialylated oligosaccharide. The present invention also provides a cell for production of the 3'sialylated oligosaccharide and the use of the cell in a cultivation or incubation.

17 Claims, No Drawings

Specification includes a Sequence Listing.

(56) References Cited

OTHER PUBLICATIONS

Gilbert M et al., "Cloning of the Lipooligosaccharide ALPHA-2,3-Sialyltransferase From the Bacterial Pathogens Neisseria Meningitidis and Neisseria Gonorrhoeae," Journal of Biological Chemistry, American Society for Biochemistry and Molecular Biology, US, vol. 271, No. 45, Nov. 8, 1996, pp. 28271-28276.

Gilbert M et Al, "The synthesis of sialylated oligosaccharides using a CMP-Neu5Ac synthetase/sialyltransferase fusion", Nature Biotechnology, Nature Publishing Group US, New York, vol. 16, No. 8, Aug. 1, 1998, pp. 769-772.

International Search Report for International Application No. PCT/EP2023/058392, mailed Sep. 4, 2023, 11 pages.

International Written Opinion for International Application No. PCT/EP2023/058392, mailed Sep. 4, 2023, 13 pages.

Jones Paul A et al., "Haemophilus influenzae Type b Strain A2 Has Multiple Sialyltransferases Involved in Lipooligosaccharide Sialylation*," The Journal of Biological Chemistry, vol. 277, No. 17, Feb. 12, 2002, pp. 14598-14611.

Li Y et al, "Sialic acid metabolism and sialyltransferases: natural functions and applications," Applied Microbiology and Biotechnology, Springer Berlin Heidelberg, Berlin/Heidelberg, vol. 94, No. 4, Apr. 13, 2012, pp. 887-905.

Li Z et al, "Efficient Production of 3'-Sialyllactose by Single Whole-Cell in One-Pot Biosynthesis," Processes, vol. 9, No. 6, May 26, 2021, pp. 12.

Li et al., "Enhancement of Production of d-Glucosamine in *Escherichia coli* by Blocking Three Pathways Involved in the Consumption of GlcN and GlcNAc," Molecular Biotechnology, vol. 62, 2020, pp. 387-399.

Lu et al., "Engineered Microbial Routes for Human Milk Oligosaccharides Synthesis," Acs synth. Biol, vol. 10, 2021, pp. 923-938.

Schelch et al., "Bacterial sialyltransferases and their use in biocatalytic cascades for sialooligosaccharide production," Biotechnology Advances, vol. 44, Aug. 18, 2020, 107613, pp. 31.

Zhang et al., "Microbial production of sialic acid and sialylated human milk oligosaccharides: Advances and perspectives," Biotechnology Advances, vol. 37, Apr. 24, 2019, pp. 787-800.

\* cited by examiner

SEQUENCE LISTING

```
Sequence total quantity: 15
SEQ ID NO: 1           moltype = AA  length = 303
FEATURE                Location/Qualifiers
source                 1..303
                       mol_type = protein
                       organism = Streptococcus acidominimus
SEQUENCE: 1
MKKLYICHTV YHLLITMCHL DFCEDSHLLL FDTISDRELL VKRLRKLNYT GLVFFEAKDC   60
TDYAQYDLQD FDEIYLFNDW TYIGQYLRSN KQSYSLIEDG YNYYAYHSYP ESFSRLRQIY  120
HCIFRNSLPL GYSKYVKQIE LNSLEVLKDT DKRRKKCKEV PRLALFSNLS DLKKERLLSL  180
FAVKPIEVRS QDTLLVLTQP LYQDGLAGFE TAEKQLAFYQ KIVDSYKQER TIYFKVHPRD  240
EIDYSAIEDV VFLRQDVPME LYEFVGNYYF DTGITHSSTA LEYLSCVGEK IVLCDMKGKM  300
SEK                                                                303

SEQ ID NO: 2           moltype = AA  length = 303
FEATURE                Location/Qualifiers
source                 1..303
                       mol_type = protein
                       organism = Streptococcus azizii
SEQUENCE: 2
MKKIYICHTV YHLLITMCHV DWCEESQLLL FDSIRDRELL VERLRSLNYT GTIFLEDETC   60
TNYEQYDLKA DSDIYLFNDW THIGQYLRRH KIPHYLLEDG YNYYAYHSYP DEFSRLRQIY  120
YFIFRNYLPF GYSKHAKQIE LNSIDVLKET DKRRKKCKEV PRVELFSNLS DPQKERLLAL  180
FAVEPIEVGP QDSLLVLTQP LYQDGLPGFE TAEQQLAFYQ EIVDSYKDNR TIYFKVHPRD  240
QVDYSAIKGV IFLKQNVPME LYEFVGKYYF DTGITHSSTA LEYLSCVGEK IVLWDMRGKM  300
CEK                                                                303

SEQ ID NO: 3           moltype = AA  length = 281
FEATURE                Location/Qualifiers
source                 1..281
                       mol_type = protein
```

```
                          note = 12198
                          organism = Helicobacter mustelae
SEQUENCE: 3
MNKRAVVIAG NGPSLAQIDY SLLPRDFDVF RCNQFYFEDK YFLGKKIQAV FFNPGVFFEQ    60
YYTLKQLEER GEYCYEEVYS SMMHWAGERD YEELDFKRLY PEVKIAHDEA LKCPRLASHF   120
KYQDMYFKKR ITSGMLMLFV AAIKGYREIY LAGIDFYETG NYAFEHKSTN ANSLIGYEEG   180
VVTEQHSKEV DLEALDLIRD FFDLHIYALC PQSPIASYLS IPFPSPANFF PPKKKEGYIC   240
DILIPQVRNP LLKEIPPGIA RRILNRLQRY FGFLFPFVTK K                      281

SEQ ID NO: 4              moltype = AA   length = 400
FEATURE                   Location/Qualifiers
source                    1..400
                          mol_type = protein
                          note = strain W16181
                          organism = Actinobacillus vicugnae
SEQUENCE: 4
MESTTQVQAI DIYIDFATIP SLCYFLHFLK HKSDQQRLRF FSLARFEIPS TFIEQNGNDT    60
IHFSRNQDHD ITQLLTQLQR FFSQGEKQFE LRLHLNMFHS FEIFLSFNHI YERYKDRISK   120
VSLHLYDDGS EGLMKQYQLQ QSHSLTQDLA ETKRALVSLF ETGEGSFKHV DLIRYTWHAV   180
FDTRYYLLSD HFLSHENLQP LKAELADYQL LNLMEYQHLS ATDLLWLKQI LKVDADLDML   240
LQKLNTQPVY FFSGTTLFNI NFEHKKRLAN IHAALIREHL DPNSSLFIGE PYLFVFKGHP   300
NSPEINKALR EHYPDIVFLP ENIPPEILAL LGFAPAKIGG FASTIHVNSA KQKLANLFFL   360
SSTDEQERNC FDGYIKQYAF AQAMLAMQLV NQDQVFYCSL                        400

SEQ ID NO: 5              moltype = AA   length = 405
FEATURE                   Location/Qualifiers
source                    1..405
                          mol_type = protein
                          note = strain HS4635
                          organism = Glaesserella australis
SEQUENCE: 5
MNKEEYQKVE IYLDFATIPT LNYFFHFIEN YQDKDTIRLF GLGRFKIPDS VIEQYPAGKI    60
YFAKSEIDAQ HEFKQLCFGV LKNIDQKMVL NLHVNLTHSF VILASLLDIL FSLEERKCHS   120
ICLHLYDDGA EGPRQLYTLS QRSDLEELVA FHKNQMANLL HAGKATISVL GVFRYLWQEI   180
FTTHYHLLDT KVLDLASLAP LKSEMINYHK MSFNHFHKFN QEQKRLFLTL LDLDTKYENQ   240
IIDLFKNNKT FVFTGTTMFD CDSNLLNFLE NAHTQIIENM IYPEGKYYHQ YDDYIFLYKG   300
HPHAKELNKR ILEKFNKLIN IPEHLPFEVL YLLGLNPTKI GGFFSTSYFQ VESDRIADVF   360
FLSSSDPEKN KKYYVFSEQY DLMKVLLALD YVKEEQCHLI NFNIK                  405

SEQ ID NO: 6              moltype = AA   length = 402
FEATURE                   Location/Qualifiers
source                    1..402
                          mol_type = protein
                          organism = Vespertiliibacter pulmonis
SEQUENCE: 6
MANIVTKNVE VYLDYATIPS LNYFLHFVKN KDDMETIRLF GLSRFTIPDS IVNAYPEGII    60
QYYPVKTGDQ DKFNQAFACL ISESSTKLKF NIHLNLFHSL MMFVPLLQIC NQYSDKVEEI   120
KLNFYDDGAE GISLYLSLSK MDIDLIKEVD FHYSILSKLN ETREIKFNFL NILRYLWNAN   180
FSSHYYLMQS NYLDIAQLSP LKEKLNGSYS EMDLTRYSSL SVEQWQMILA ILNLPLDLVN   240
SYIKLSSEYK VFVFTGTTIF DGNETVLEKL HIKLLLQYLD PKSKYYIGDN YLIFYKGHPN   300
SPEINKKVDD IFKSVIRLPD NIPLEILFLL GFKAKKLGGF ASSLYLSLDL KKREAEIESL   360
AFLTSNEDKT KHSLFETQYN LAQQLMIDLGY VTSNQIIYYT DI                    402

SEQ ID NO: 7              moltype = AA   length = 318
FEATURE                   Location/Qualifiers
source                    1..318
                          mol_type = protein
                          note = 7271 (VII)
                          organism = Streptococcus agalactiae
SEQUENCE: 7
MNYFVCHTLY HLLITIIKLK DKENTRIFIC DTIPDYGAWI KILNNQGIKT ELFKELDYRE    60
QLQNKNVEEV MNLVDSYLKH YFERVNTQVY LFNDDTLMGR YMAYLGKNYH LIEDGYNCFQ   120
AKLFFGGSVV KRIIKTYFLK KYVPYGFSKY CLSIEVNSLE GLPHDRRSKK YKELPRKELF   180
DSLTQEGSKL IFKLFKMKPI TIAPKSVLLL TQPLAQDKWY KTATERFQSI QEQYDYFEGI   240
VHDYRERGYN IYLKVHPRDA VDYSKLPVEL LPSNIPMEII ELMLTGRFEV GITHSSTALD   300
FLTCVDRKII LVNLKDIK                                                318

SEQ ID NO: 8              moltype = AA   length = 318
FEATURE                   Location/Qualifiers
source                    1..318
                          mol_type = protein
                          note = 2603V/R
                          organism = Streptococcus agalactiae
SEQUENCE: 8
MNNFVCHTLY HLLITIIKLK DKENTRIFIC DTITNYETWV KTLNEQGIRT EAVKEFAYRE    60
QLQSKNIEEV MELVDSDLNH YFERVDTQVY LFNDDTLIGR YMVYLGKNYH LIEDGYNCFQ   120
AKLFLGGSVV KRVIKTYLFK KYVPYGFSKY CLSIEVNSLV GLPHDIRSKK YKELPRKKLF   180
DSLNKEQKSL IFKIFKTKPL TITPKSVLLL TQPLAQDKCY KTPTERFQSI QEQYDYFDDI   240
VQEYRTLGYN VYLKVHPRDV VDYSKLPVEL LPSNIPMEII ELMLTGRFEF GITHSSTALD   300
```

-continued

```
FLTCVDKKIT LVDLKDIK                                                         318

SEQ ID NO: 9              moltype = AA  length = 223
FEATURE                   Location/Qualifiers
source                    1..223
                          mol_type = protein
                          organism = Pasteurella multocida
SEQUENCE: 9
MTNIAIIPAR AGSKGIPDKN LQPVGGHSLI GRAILAAKNA DVFDMIVVTS DGDNILREAE            60
KYGALALKRP AELAQDNSRT IDAILHALES LNIREGTCTL LQPTSPLRDH LDIKNAMDMY           120
VNGGVHSVVS ACECEHHPYK AFALSKDHEV LPVREIADFE AARQTLPKMY RANGAIYIND           180
IAQLLKEKYF FIPPLKFYLM PTYRSVDIDV KQDLELAEIL SNK                             223

SEQ ID NO: 10             moltype = AA  length = 609
FEATURE                   Location/Qualifiers
source                    1..609
                          mol_type = protein
                          note = MG1655
                          note = K-12 strain
                          organism = Escherichia coli
SEQUENCE: 10
MCGIVGAIAQ RDVAEILLEG LRRLEYRGYD SAGLAVVDTE GHMTRLRRLG KVQMLAQAAE            60
EHPLHGGTGI AHTRWATHGE PSEVNAHPHV SEHIVVHNG IIENHEPLRE ELKARGYTFV            120
SETDTEVIAH LVNWELKQGG TLREAVLRAI PQLRGAYGTV IMDSRHPDTL LAARSGSPLV           180
IGLGMGENFI ASDQLALLPV TRRFIFLEEG DIAEITRRSV NIFDKTGAEV KRQDIESNLQ           240
YDAGDKGIYC HYMQKEIYEQ PNAIKNTLTG RISHGQVDLS ELGPNADELL SKVEHIQILA           300
CGTSYNSGMV SRYWFESLAG IPCDVEIASE FRYRKSAVRR NSLMITLSQS GETADTLAGL           360
RLSKELGYLG SLAICNVPGS SLVRESDLAL MTNAGTEIGV ASTKAFTTQL TVLLMLVAKL           420
SRLKGLDASI EHDIVHGLQA LPSRIEQMLS QDKRIEALAE DFSDKHHALF LSRGDQYPIA           480
LEGALKLKEI SYIHAEAYAA GELKHGPLAL IDADMPVIVV APNNELLEKL KSNIEEVRAR           540
GGQLYVFADQ DAGFVSSDNM HIIEMPHVEE VIAPIFYTVP LQLLAYHVAL IKGTDVDQPR           600
NLAKSVTVE                                                                   609

SEQ ID NO: 11             moltype = AA  length = 268
FEATURE                   Location/Qualifiers
source                    1..268
                          mol_type = protein
                          organism = Pasteurella multocida
SEQUENCE: 11
MDKFAEHEIP KAVIVAGNGE SLSQIDYRLL PKNYDVFRCN QFYFEERYFL GNKIKAVFFT            60
PGVFLEQYYT LYHLKRNNEY FVDNVILSSF NHPTVDLEKS QKIQALFIDV INGYEKYLSK           120
LTAFDVYLRY KELYENQRIT SGVYMCAVAI AMGYTDIYLT GIDFYQASEE NYAFDNKKPN           180
IIRLLPDFRK EKTLFSYHSK DIDLEALSFL QQHYHVNFYS ISPMSPLSKH FPIPTVEDDC           240
ETTFVAPLKE NYINDILLPP HFVYEKLG                                             268

SEQ ID NO: 12             moltype = AA  length = 425
FEATURE                   Location/Qualifiers
source                    1..425
                          mol_type = protein
                          organism = Avibacterium paragallinarum
SEQUENCE: 12
MFNRKYNKRD NKKMIIYFDV ATLPSLNMIF DLLKQKENNE IERIVGFSRF ELDETILKHF            60
PDNKISFHKV DLDSKLELFA KKILEIIKNS PTKYALTIHT NLCHSLVIIP KLMSILNLVK           120
HKYYIEQLYL YDDGSSDYLD LYNQRENNLA LLFKTAKKNT SLRLKQEIIY YFPRVHPYRL           180
IYKVIRFKFF LRKYFHFTYL NKYTWHTLFP TKYIVLCPEY FETDKKMSYV NKELEKHFTK           240
MNFQQFHTLT SENKSLFLHF INIDSQQLHT LARTLKQKNT LILTGTTTWK DERLEFAKLQ           300
ANLLKNLIDT NFKNYHILFK GHPAATDINT FIIDTLKIES IPENIPLEIL IILDLLPDTI           360
CGMPSSIYFS LPKEKVGKLI FLENKYIENT NPEKLTKFEK LISVILKINT NKSIELLKNK           420
QNAIK                                                                       425

SEQ ID NO: 13             moltype = AA  length = 722
FEATURE                   Location/Qualifiers
source                    1..722
                          mol_type = protein
                          organism = Homo sapiens
SEQUENCE: 13
MEKNGNNRKL RVCVATCNRA DYSKLAPIMF GIKTEPEFFE LDVVVLGSHL IDDYGNTYRM            60
IEQDDPFDINT RLHTIVRGED EAAMVESVGL ALVKLPDVLN RLKPDIMIVH GDRFDALALA          120
TSAALMNIRI LHIEGGEVSG TIDDSIRHAI TKLAHYHVCC TRSAEQHLIS MCEDHDRILL           180
AGCPSYDKLL SAKNKDYMSI IRMWLGDDVK SKDYIVALQH PVTTDIKHSI KMFELTLDAL           240
ISFNKRTLVL FPNIDAGSKE MVLVMRKKGI EHHPNFRAVK HVPFDQFIQL VAHAGCMIGN           300
SSCGVREVGA FGTPVINLGT RQIGRETGEN VLHVRDADTQ DKILQALHLQ FGKQYPCSKI           360
YGDGNAVPRI LKFLKSIDLQ EPLQKKFCFP PVKENISQDI DHILETLSAL AVDLGGTNLR           420
VAIVSMKGEI VKKYTQFNPK TYEERINLIL QMCVEAAAEA VKLNCRILGV GISTGGRVNP           480
REGIVLHSTK LIQEWNSVDL RTPLSDTLHL PVWVDNDGNC AALAERKFGQ GKGLENFVTL           540
ITGTGIGGGI IHQHELIHGS SFCAAELGHL VVSLDGPDCS CGGSHGCIEAY ASGMALQREA         600
KKLHDEDLLL VEGMSVPKDE AVGALHLIQA AKLGNAKAQS ILRTAGTALG LGVVNILHTM           660
NPSLVILSGV LASHYIHIVK DVIRQQALSS VQDVDVVVSD LVDPALLGAA SMVLDYTTRR          720
IY                                                                          722
```

```
SEQ ID NO: 14         moltype = AA  length = 371
FEATURE               Location/Qualifiers
source                1..371
                      mol_type = protein
                      note = MC58
                      organism = Neisseria meningitidis
SEQUENCE: 14
MGLKKACLTV LCLIVFCFGI FYTFDRVNQG ERNAVSLLKE KLFNEEGEPV NLIFCYTILQ    60
MKVAERIMAQ HPGERFYVVL MSENRNEKYD YYFNQIKDKA ERAYFFHLPY GLNKSFNFIP   120
TMAELKVKSM LLPKVKRIYL ASLEKVSIAA FLSTYPDAEI KTFDDGTGNL IQSSSYLGDE   180
FSVNGTIKRN FARMMIGDWS IAKTRNASDE HYTIFKGLKN IMDDGRRKMT YLPLFDASEL   240
KTGDETGGTV RILLGSPDKE MKEISEKAAK NFKIQYVAPH PRQTYGLSGV TTLNSPYVIE   300
DYILREIKKN PHTRYEIYTF FSGAALTMKD FPNVHVYALK PASLPEDYWL KPVYALFTQS   360
GIPILTFDDK N                                                       371

SEQ ID NO: 15         moltype = AA  length = 371
FEATURE               Location/Qualifiers
source                1..371
                      mol_type = protein
                      organism = Neisseria gonorrhoeae
SEQUENCE: 15
MGLKKVCLTV LCLIVFCFGI FYTFDRVNQG ERNAVSLLKD KLFNEEGKPV NLIFCYTILQ    60
MKVAERIMAQ HPGERFYVVL MSENRNEKYD YYFNQIKDKA ERAYFFYLPY GLNKSFNFIP   120
TMAELKVKSM LLPKVKRIYL ASLEKVSIAA FLSTYPDAEI KTFDDGTNNL IRESSYLGGE   180
FAVNGAIKRN FARMMVGDWS IAKTRNASDE HYTIFKGLKN IMDDGRRKMT YLPLFDASEL   240
KAGDETGGTV RILLGSPDKE MKEISEKAAK NFNIQYVAPH PRQTYGLSGV TALNSPYVIE   300
DYILREIKKN PHTRYEIYTF FSGAALTMKD FPNVHVYALK PASLPEDYWL KPVYALFRQA   360
DIPILTFDDK N                                                       371
```

SIALYLTRANSFERASES FOR THE PRODUCTION OF SIALYLATED OLIGOSACCHARIDES

CROSS-REFERENCE TO RELATED APPLICATIONS

This application is a national phase entry under 35 U.S.C. § 371 of International Patent Application PCT/EP2023/058392, filed Mar. 30, 2023, designating the United States of America and published as International Patent Publication WO 2023/187109 A1 on Oct. 5, 2023, which claims the benefit under Article 8 of the Patent Cooperation Treaty of European Union Patent Application Serial No. 22166399.0, filed Apr. 1, 2022, of European Union Patent Application Serial No. 23151744.2, filed Jan. 16, 2023, and of Luxembourg Patent Application Serial No. LU501775, filed Apr. 1, 2022.

STATEMENT REGARDING ELECTRONIC FILING OF A SEQUENCE LISTING

Pursuant to 37 C.F.R. § 1.831 through 1.835, a Sequence Listing XML file entitled "2024-09-20_Sequence Listing_18185US", 21,020 bytes in size, generated Sept. 20, 2024, has been submitted via EFS-Web is provided in lieu of a paper copy. This Sequence Listing is hereby incorporated by reference into the specification for its disclosures.

TECHNICAL FIELD

This disclosure is in the technical field of synthetic biology, metabolic engineering and cell cultivation. This disclosure relates to newly identified sialyltransferases having alpha-2,3-sialyltransferase activity on the galactose residue of lactose. This disclosure also describes methods for the production of a 3'sialylated oligosaccharide using any one of the newly identified sialyltransferases as well as the purification of the 3'sialylated oligosaccharide. This disclosure also provides a cell for production of the 3'sialylated oligosaccharide and the use of the cell in a cultivation or incubation.

BACKGROUND

More than 150 structurally distinct human milk oligosaccharides (HMOs) have been identified to date. Although HMOs represent only a minor amount of total human milk nutrients, their beneficial effects on the development of breast-fed infants became evident over the past decades.

Among the HMOs, sialylated HMOs (SHMOs) were observed to support several beneficial effects as described in the art. Among the sialylated oligosaccharides in human milk, 3'sialyllactose, 6'sialyllactose, sialyllacto-N-tetraose a, sialyl lacto-N-tetraose b, sialyllacto-N-tetraose c and disialyllacto-N-tetraose are the most prevalent members.

Sialylated oligosaccharides are found to be a complex structure and their chemical or (chemo-)enzymatic syntheses has been proven challenging: there are extensive difficulties, e.g., control of stereochemistry, formation of specific linkages, availability of feedstocks, etc. As a consequence, alternative production methods have been developed, amongst which efforts in metabolic engineering of microorganisms to produce sialylated oligosaccharides have been made.

Several sialyltransferases have been identified and characterized to date, from bacterial species e. g. from *Neisseria*, *Campylobacter*, *Pasteurella*, *Helicobacter* and Photobacterium, as well as from mammals and viruses. Sialyltransferases have been generally classified into six glycosyltransferase (GT) families, based on protein sequence similarities. Sialyltransferases are distinguished due to the glycosidic linkages that they form, e. g. into a-2,3-, a-2,6- and a-2,8-sialyltransferases. All of these sialyltransferases transfer the sialic acid residue from cytidine 5'-monophosphate sialic acid (e. g. CMP-NeuNAc) to a variety of acceptor molecules, usually a galactose (Gal) moiety, an N-acetylgalactosamine (GalNAc) moiety or an N-acetylglucosamine (GlcNAc) moiety or another sialic acid (Sia) moiety. Several bacterial a-2,3-sialyltransferases were well characterized in the past and are already proven to be suitable for the production of 3'sialyllactose (6'SL). The most commonly used enzyme for microbial 3'SL production is the beta-galactoside alpha-2,3-sialyltransferase from *Pasteurella multocida*.

BRIEF SUMMARY

Provided are tools and methods by means of which a sialylated oligosaccharide, preferably a 3'sialylated oligosaccharide, more preferably 3'sialyllactose (3'SL, Neu5Ac-a2,3-Gal-b1,4-Glc) and/or 3'KDO-lactose, can be produced, preferably in an efficient, time and cost-effective way and which yields high amounts of the desired oligosaccharide.

Provided are newly identified sialyltransferases as described herein, each of which can be used in a method for the production of a sialylated oligosaccharide, preferably a 3'sialylated oligosaccharide, more preferably 3'SL and/or 3'KDO-lactose. Furthermore, any one of the newly identified sialyltransferases can be used in a cell for production of a sialylated oligosaccharide, preferably a 3'sialylated oligosaccharide, more preferably 3'SL and/or 3'KDO-lactose.

More specifically, this disclosure provides newly identified sialyltransferases having alpha-2,3-sialyltransferase activity on the galactose (Gal) residue of lactose (Gal-b1,4-Glc) and comprising an amino acid sequence that is at least 67.0% identical over a stretch of at least 150 amino acid residues, preferably at least 200 amino acid residues, to any one of the amino acid sequences as represented by SEQ ID NOs:05, 01, 02, 03, 06, 07 or 08, or that is at least 85.0% identical over a stretch of at least 150 amino acid residues, preferably at least 200 amino acid residues, to the amino acid sequence as represented by SEQ ID NO:04 or that is at least 60.0% identical over a stretch of at least 150 amino acid residues, preferably at least 200 amino acid residues, to the amino acid sequence as represented by SEQ ID NO:12. Even more specifically, this disclosure provides newly identified sialyltransferases having alpha-2,3-sialyltransferase activity on the galactose (Gal) residue of lactose (Gal-b1,4-Glc) and comprising an amino acid sequence that is at least 80.0% identical to any one of the full-length amino acid sequences as represented by SEQ ID NOs:05, 04, 12, 01, 02, 03, 06, 07 or 08.

This disclosure also provides methods and a cell for the production of a sialylated oligosaccharide, preferably a 3'sialylated oligosaccharide, more preferably 3'SL and/or 3'KDO-lactose. This disclosure also provides methods for the purification of the sialylated oligosaccharide, preferably a 3'sialylated oligosaccharide, more preferably 3'SL and/or 3'KDO-lactose. Furthermore, this disclosure provides a cell that is metabolically engineered with any one of the newly identified sialyltransferases as described herein and that comprises a pathway for the production of the sialylated oligosaccharide, preferably a 3'sialylated oligosaccharide, more preferably 3'SL and/or 3'KDO-lactose.

DETAILED DESCRIPTION

Definitions

The words used in this disclosure to describe the invention and its various embodiments are to be understood not only in the sense of their commonly defined meanings, but to include by special definition in this disclosure structure, material or acts beyond the scope of the commonly defined meanings. Thus, if an element can be understood in the context of this disclosure as including more than one meaning, then its use in a claim must be understood as being generic to all possible meanings supported by the disclosure and by the word itself.

The various aspects and embodiments of the invention disclosed herein are to be understood not only in the order and context specifically described in this disclosure, but to include any order and any combination thereof. Each embodiment as identified herein may be combined together unless otherwise indicated. All publications, patents, and patent applications mentioned in this disclosure are herein incorporated by reference to the same extent as if each individual publication, patent, or patent application was specifically and individually indicated to be incorporated by reference in its entirety.

Whenever the context requires, unless specifically stated otherwise, all words used in the singular number shall be deemed to include the plural and vice versa. Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry and nucleic acid chemistry and hybridization described herein are those well-known and commonly employed in the art. Standard techniques are used for nucleic acid and peptide synthesis. Generally, enzymatic reactions and purification steps are performed according to the manufacturer's specifications.

In this disclosure, there have been disclosed embodiments of this disclosure, and although specific terms are employed, the terms are used in a descriptive sense only and not for purposes of limitation, the scope of this disclosure being set forth in the following claims. It must be understood that the illustrated embodiments have been set forth only for the purposes of example and that it should not be taken as limiting the invention. It will be apparent to those skilled in the art that alterations, other embodiments, improvements, details and uses can be made consistent with the letter and spirit of the disclosure herein and within the scope of this disclosure, which is limited only by the claims, construed in accordance with the patent law, including the doctrine of equivalents. In the claims that follow, reference characters used to designate claim steps are provided for convenience of description only, and are not intended to imply any particular order for performing the steps, unless specifically stated otherwise.

Throughout this disclosure, unless explicitly stated otherwise, the features "synthesize," "synthesized" and "synthesis" are interchangeably used with the features "produce," "produced" and "production," respectively. Throughout this disclosure, unless explicitly stated otherwise, the expressions "capable of . . . <verb>" and "capable to . . . <verb>" are preferably replaced with the active voice of the verb and vice versa. For example, the expression "capable of expressing" is preferably replaced with "expresses" and vice versa, i.e., "expresses" is preferably replaced with "capable of expressing." In this disclosure and in its claims, the verb "to comprise," "to have" and "to contain" and their conjugations are used in their non-limiting sense to mean that items following the word are included, but items not specifically mentioned are not excluded. Throughout this disclosure, the verb "to comprise" may be replaced by "to consist" or "to consist essentially of" and vice versa. In addition, the verb "to consist" may be replaced by "to consist essentially of" meaning that a composition as defined herein may comprise additional component(s) than the ones specifically identified, the additional component(s) not altering the unique characteristic of the invention. In this disclosure and in its claims, unless specifically stated otherwise, the verbs "to comprise," "to have" and "to contain," and their conjugations, may be replaced by "to consist of" (and its conjugations) or "to consist essentially of" (and its conjugations) and vice versa. In addition, reference to an element by the indefinite article "a" or "an" does not exclude the possibility that more than one of the elements is present, unless the context clearly requires that there be one and only one of the elements. The indefinite article "a" or "an" thus usually means "at least one."

Throughout this disclosure, unless explicitly stated otherwise, the articles "a" and "an" are preferably replaced by "at least two," more preferably by "at least three," even more preferably by "at least four," even more preferably by "at least five," even more preferably by "at least six," most preferably by "at least two." The word "about" or "approximately" when used in association with a numerical value (e.g., "about 10") or with a range (e.g., "about x to approximately y") preferably means that the value or range is interpreted as being as accurate as the method used to measure it. If no error margins are specified, the expression "about" or "approximately" when used in association with a numerical value is interpreted as having the same round-off as the given value. Throughout this disclosure and its claims, unless otherwise stated, the expression "from x to y," wherein x and y represent numerical values, refers to a range of numerical values wherein x is the lower value of the range and y is the upper value of the range. Herein, x and y are also included in the range.

According to this disclosure, the term "polynucleotide(s)" generally refers to any polyribonucleotide or polydeoxyribonucleotide, which may be unmodified RNA or DNA or modified RNA or DNA. "Polynucleotide(s)" include, without limitation, single- and double-stranded DNA, DNA that is a mixture of single- and double-stranded regions or single-, double- and triple-stranded regions, single- and double-stranded RNA, and RNA that is mixture of single- and double-stranded regions, hybrid molecules comprising DNA and RNA that may be single-stranded or, more typically, double-stranded, or triple-stranded regions, or a mixture of single- and double-stranded regions. In addition, "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. As used herein, the term "polynucleotide(s)" also includes DNAs or RNAs as described above that contain one or more modified bases. Thus, DNAs or RNAs with backbones modified for stability or for other reasons are "polynucleotide(s)" according to this disclosure. Moreover, DNAs or RNAs comprising unusual bases, such as inosine, or modified bases, such as tritylated bases, are to be understood to be covered by the term "polynucleotides." It will be appreciated that a great variety of modifications have been made to DNA and RNA that serve many useful purposes known to those of skill in the art. The term "polynucleotide(s)" as it is employed herein embraces such chemically, enzymatically or metabolically modified forms of polynucleotides, as well as the chemical forms of DNA and RNA characteristic of viruses and cells, including, for example, simple and complex cells. The term "polynucleotide(s)" also embraces short polynucleotides often referred to as oligonucleotide(s).

"Polypeptide(s)" refers to any peptide or protein comprising two or more amino acids joined to each other by peptide bonds or modified peptide bonds. "Polypeptide(s)" refers to both short chains, commonly referred to as peptides, oligopeptides and oligomers and to longer chains generally referred to as proteins. Polypeptides may contain amino acids other than the 20 gene encoded amino acids. "Polypeptide(s)" include those modified either by natural processes, such as processing and other post-translational modifications, but also by chemical modification techniques. Such modifications are well described in basic texts and in more detailed monographs, as well as in a voluminous research literature, and they are well known to the skilled person. The same type of modification may be present in the same or varying degree at several sites in a given polypeptide. Furthermore, a given polypeptide may contain many types of modifications. Modifications can occur anywhere in a polypeptide, including the peptide backbone, the amino acid sidechains, and the amino or carboxyl termini. Modifications include, for example, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulphide bond formation, demethylation, formation of covalent cross-links, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, lipid attachment, sulfation, gamma-carboxylation of glutamic acid residues, hydroxylation and ADP-ribosylation, selenoylation, transfer-RNA mediated addition of amino acids to proteins, such as arginylation, and ubiquitination. Polypeptides may be branched or cyclic, with or without branching. Cyclic, branched and branched circular polypeptides may result from post-translational natural processes and may be made by entirely synthetic methods, as well.

The term "polynucleotide encoding a polypeptide" as used herein encompasses polynucleotides that include a sequence encoding a polypeptide of the invention. The term also encompasses polynucleotides that include a single continuous region or discontinuous regions encoding the polypeptide (for example, interrupted by integrated phage or an insertion sequence or editing) together with additional regions that also may contain coding and/or non-coding sequences.

"Isolated" means altered "by the hand of man" from its natural state, i.e., if it occurs in nature, it has been changed or removed from its original environment, or both. For example, a polynucleotide or a polypeptide naturally present in a living organism is not "isolated," but the same polynucleotide or polypeptide separated from the coexisting materials of its natural state is "isolated," as the term is employed herein. Similarly, a "synthetic" sequence, as the term is used herein, means any sequence that has been generated synthetically and not directly isolated from a natural source. "Synthesized," as the term is used herein, means any synthetically generated sequence and not directly isolated from a natural source.

"Recombinant" means genetically engineered DNA prepared by transplanting or splicing genes from one species into the cells of a host organism of a different species. Such DNA becomes part of the host's genetic makeup and is replicated.

The terms "recombinant" or "transgenic" or "metabolically engineered" or "genetically engineered" as used herein with reference to a cell or host cell are used interchangeably and indicates that the cell replicates a heterologous nucleic acid, or expresses a peptide or protein encoded by a heterologous nucleic acid (i.e., a sequence "foreign to the cell" or a sequence "foreign to the location or environment in the cell"). Such cells are described to be transformed with at least one heterologous or exogenous gene or are described to be transformed by the introduction of at least one heterologous or exogenous gene. Recombinant or metabolically engineered or genetically engineered or transgenic cells can contain genes that are not found within the native (non-recombinant) form of the cell. Recombinant cells can also contain genes found in the native form of the cell wherein the genes are modified and re-introduced into the cell by artificial means. The terms also encompass cells that contain a nucleic acid endogenous to the cell that has been modified or its expression or activity has been modified without removing the nucleic acid from the cell; such modifications include those obtained by gene replacement, replacement of a promoter; site-specific mutation; CrispR; riboswitch; recombineering; ssDNA mutagenesis; transposon mutagenesis and related techniques as known to a person skilled in the art. Accordingly, a "recombinant polypeptide" is one that has been produced by a recombinant cell. The terms also encompass cells that have been modified by removing a nucleic acid endogenous to the cell by means of common well-known technologies for a skilled person (like e.g., knocking-out genes).

A "heterologous sequence" or a "heterologous nucleic acid," as used herein, is one that originates from a source foreign to the particular cell (e.g., from a different species), or, if from the same source, is modified from its original form or place in the genome. Thus, a heterologous nucleic acid operably linked to a promoter is from a source different from that from which the promoter was derived, or, if from the same source, is modified from its original form or place in the genome. The heterologous sequence may be stably introduced, e.g., by transfection, transformation, conjugation or transduction, into the genome of the host microorganism cell, wherein techniques may be applied that will depend on the cell and the sequence that is to be introduced. Various techniques are known to a person skilled in the art and are, e.g., disclosed in Sambrook et al., Molecular Cloning: A Laboratory Manual, 2nd Ed., Cold Spring Harbor Laboratory Press, Cold Spring Harbor, N.Y. (1989). The term "mutant" or "engineered" cell or microorganism as used within the context of this disclosure refers to a cell or microorganism that is genetically engineered.

The term "endogenous" within the context of the present disclosure refers to any polynucleotide, polypeptide or protein sequence that is a natural part of a cell and is occurring at its natural location in the cell chromosome and of which the control of expression has not been altered compared to the natural control mechanism acting on its expression. The term "exogenous" refers to any polynucleotide, polypeptide or protein sequence that originates from outside the cell under study and not a natural part of the cell or that is not occurring at its natural location in the cell chromosome or plasmid.

The term "heterologous" when used in reference to a polynucleotide, gene, nucleic acid, polypeptide, or enzyme refers to a polynucleotide, gene, nucleic acid, polypeptide, or enzyme that is from a source or derived from a source other than the host organism species. In contrast a "homologous" polynucleotide, gene, nucleic acid, polypeptide, or enzyme is used herein to denote a polynucleotide, gene, nucleic acid, polypeptide, or enzyme that is derived from the host organism species. When referring to a gene regulatory sequence or to an auxiliary nucleic acid sequence used for maintaining or manipulating a gene sequence (e.g., a promoter, a 5' untranslated region, 3' untranslated region, poly A addition sequence, intron sequence, splice site, ribosome binding site, internal ribosome entry sequence, genome homology region, recombination site, etc.), "heterologous" means that the regulatory sequence or auxiliary sequence is not naturally associated with the gene with which the regulatory or auxiliary nucleic acid sequence is juxtaposed in a construct, genome, chromosome, or episome. Thus, a promoter operably linked to a gene to which it is not operably linked to in its natural state (i.e., in the genome of a non-genetically engineered organism) is referred to herein as a "heterologous promoter," even though the promoter may be derived from the same species (or, in some cases, the same organism) as the gene to which it is linked.

The term "modified expression" of a gene relates to a change in expression compared to the wild-type expression of the gene in any phase of the production process of the desired 3'sialylated oligosaccharide. The modified expression is either a lower or higher expression compared to the wild-type, wherein the term "higher expression" is also defined as "overexpression" of the gene in the case of an endogenous gene or "expression" in the case of a heterologous gene that is not present in the wild-type strain. Lower expression is obtained by means of common well-known technologies for a skilled person (such as the usage of siRNA, CrispR, CrispRi, riboswitch, recombineering, homologous recombination, ssDNA mutagenesis, RNAi, miRNA, asRNA, mutating genes, knocking-out genes, transposon mutagenesis, etc.), which are used to change the genes in such a way that they are "less-able" (i.e., statistically significantly 'less-able' compared to a functional wild-type gene) or completely unable (such as knocked-out genes) to produce functional final products. The term "riboswitch" as used herein is defined to be part of the messenger RNA that folds into intricate structures that block expression by interfering with translation. Binding of an effector molecule induces conformational change(s) permitting regulated expression post-transcriptionally. Next to changing the gene of interest in such a way that lower expression is obtained as described above, lower expression can also be obtained by changing the transcription unit, the promoter, an untranslated region, the ribosome binding site, the Shine Dalgarno sequence or the transcription terminator. Lower expression or reduced expression can, for instance, be obtained by mutating one or more base pairs in the promoter sequence or changing the promoter sequence fully to a constitutive promoter with a lower expression strength compared to the wild-type or an inducible promoter that result in regulated expression or a repressible promoter that results in regulated expression. Overexpression or expression is obtained by means of common well-known technologies for a skilled person (such as the usage of artificial transcription factors, de novo design of a promoter sequence, ribosome engineering, introduction or re-introduction of an expression module at euchromatin, usage of high-copy-number plasmids), wherein the gene is part of an "expression cassette" that relates to any sequence in which a promoter sequence, untranslated region sequence (containing either a ribosome binding sequence, Shine Dalgarno or Kozak sequence), a coding sequence (for instance, a sialyltransferase gene sequence) and optionally a transcription terminator is present, and leading to the expression of a functional active protein. The expression is either constitutive or conditional or regulated or tuneable.

The term "constitutive expression" is defined as expression that is not regulated by transcription factors other than the subunits of RNA polymerase (e.g., the bacterial sigma factors like $s^{70}$, $s^{54}$ or related s-factors and the yeast mitochondrial RNA polymerase specificity factor MTF1 that co-associate with the RNA polymerase core enzyme) under certain growth conditions. Non-limiting examples of such transcription factors are CRP, LacI, ArcA, Cra, Ic1R in *E. coli*, or AftZp, Crz1p, Skn7 in *Saccharomyces cerevisiae*, or DeoR, GntR, Fur in *B. subtilis*. These transcription factors bind on a specific sequence and may block or enhance expression in certain growth conditions. The RNA polymerase is the catalytic machinery for the synthesis of RNA from a DNA template. RNA polymerase binds a specific DNA sequence to initiate transcription, for instance, via a sigma factor in prokaryotic hosts or via MTF1 in yeasts. Constitutive expression offers a constant level of expression with no need for induction or repression.

The term "regulated expression" is defined as expression that is regulated by transcription factors other than the subunits of RNA polymerase (e.g., bacterial sigma factors) under certain growth conditions. Examples of such transcription factors are described above. Commonly expression regulation is obtained by means of an inducer, such as but not limited to IPTG, arabinose, rhamnose, fucose, allolactose or pH shifts, or temperature shifts or carbon depletion or substrates or the produced product.

The term "control sequences" refers to sequences recognized by the cells transcriptional and translational systems, allowing transcription and translation of a polynucleotide sequence to a polypeptide. Such DNA sequences are thus necessary for the expression of an operably linked coding sequence in a particular host cell, cell or organism. Such control sequences can be, but are not limited to, promoter sequences, ribosome binding sequences, Shine Dalgarno sequences, Kozak sequences, transcription terminator sequences. The control sequences that are suitable for prokaryotes, for example, include a promoter, optionally an operator sequence, and a ribosome binding site. Eukaryotic cells are known to utilize promoters, polyadenylation signals, and enhancers. DNA for a presequence or secretory leader may be operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it affects the transcription of the sequence; or a ribosome binding site is operably linked to a coding sequence if it is positioned so as to facilitate translation. The control sequences can furthermore be controlled with external chemicals, such as, but not limited to, IPTG, arabinose, lactose, allo-lactose, rhamnose or fucose via an inducible promoter or via a genetic circuit that either induces or represses the transcription or translation of the polynucleotide to a polypeptide.

Generally, "operably linked" means that the DNA sequences being linked are contiguous, and, in the case of a secretory leader, contiguous and in reading phase. However, enhancers do not have to be contiguous.

The term "wildtype" refers to the commonly known genetic or phenotypical situation as it occurs in nature.

The term "modified expression of a protein" as used herein refers to i) higher expression or overexpression of an endogenous protein, ii) expression of a heterologous protein, iii) expression and/or overexpression of a variant protein that has a higher activity compared to the wild-type (i.e., native in the expression host) protein, iv) reduced expression of an endogenous protein or v) expression and/or overexpression of a variant protein that has a reduced activity compared to the wild-type (i.e., native in the expression host) protein. Preferably, the term "modified expression of a protein" as used herein refers to i) higher expression or overexpression of an endogenous protein, ii) expression of a heterologous protein or iii) expression and/or overexpression of a variant protein that has a higher activity compared to the wild-type (i.e., native in the expression host) protein.

The term "modified activity" of a protein relates to a non-native activity of the protein in any phase of the production process of the desired 3'sialylated oligosaccharide. The term "non-native," as used herein with reference to the activity of a protein indicates that the protein has been modified to have an abolished, impaired, reduced, delayed, higher, accelerated or improved activity compared to the native activity of the protein. A modified activity of a protein is obtained by modified expression of the protein or is obtained by expression of a modified, i.e., mutant form of the protein. A mutant form of the protein can be obtained by expression of a mutant form of the gene encoding the protein, e.g., comprising a deletion, an insertion and/or a mutation of one or more nucleotides compared to the native gene sequence. A mutant form of a gene can be obtained by techniques well-known to a person skilled in the art, such as but not limited to site-specific mutation; CrispR; riboswitch; recombineering; ssDNA mutagenesis; transposon mutagenesis.

The term "non-native," as used herein with reference to a cell producing a 3'sialylated oligosaccharide, indicates that the 3'sialylated oligosaccharide is i) not naturally produced or ii) when naturally produced not in the same amounts by the cell; and that the cell has been genetically engineered to be able to produce the 3'sialylated oligosaccharide or to have a higher production of the 3'sialylated oligosaccharide.

As used herein, the term "mammary cell(s)" generally refers to mammalian mammary epithelial cell(s), mammalian mammary-epithelial luminal cell(s), or mammalian epithelial alveolar cell(s), or any combination thereof. As used herein, the term "mammary-like cell(s)" generally refers to mammalian cell(s) having a phenotype/genotype similar (or substantially similar) to natural mammalian mammary cell(s) but is/are derived from mammalian non-mammary cell source(s). Such mammalian mammary-like cell(s) may be engineered to remove at least one undesired genetic component and/or to include at least one predetermined genetic construct that is typical of a mammalian mammary cell. Non-limiting examples of mammalian mammary-like cell(s) may include mammalian mammary epithelial-like cell(s), mammalian mammary epithelial luminal-like cell(s), mammalian non-mammary cell(s) that exhibits one or more characteristics of a cell of a mammalian mammary cell lineage, or any combination thereof. Further non-limiting examples of mammalian mammary-like cell(s) may include mammalian cell(s) having a phenotype similar (or substantially similar) to natural mammalian mammary cell(s), or more particularly a phenotype similar (or substantially similar) to natural mammalian mammary epithelial cell(s). A mammalian cell with a phenotype or that exhibits at least one characteristic similar to (or substantially similar to) a natural mammalian mammary cell or a mammalian mammary epithelial cell may comprise a mammalian cell (e.g., derived from a mammary cell lineage or a non-mammary cell lineage) that exhibits either naturally, or has been engineered to, be capable of expressing at least one milk component.

As used herein, the term "non-mammary cell(s)" may generally include any mammalian cell of non-mammary lineage. In the context of this disclosure, a non-mammary cell can be any mammalian cell capable of being engineered to express at least one milk component. Non-limiting examples of such non-mammary cell(s) include hepatocyte (s), blood cell(s), kidney cell(s), cord blood cell(s), epithelial cell(s), epidermal cell(s), myocyte(s), fibroblast(s), mesenchymal cell(s), or any combination thereof. In some instances, molecular biology and genome editing techniques can be engineered to eliminate, silence, or attenuate myriad genes simultaneously.

"Variant(s)," as the term is used herein, is a polynucleotide or polypeptide that differs from a reference polynucleotide or polypeptide, respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques, by direct synthesis, and by other recombinant methods known to the persons skilled in the art.

In some embodiments, this disclosure contemplates making functional variants by modifying the structure of an enzyme as used in this disclosure. Variants can be produced by amino acid substitution, deletion, addition, or combinations thereof. For instance, it is reasonable to expect that an isolated replacement of a leucine with an isoleucine or valine, an aspartate with a glutamate, a threonine with a serine, or a similar replacement of an amino acid with a structurally related amino acid (e.g., conservative mutations) will not have a major effect on the biological activity of the resulting molecule. Conservative replacements are those that take place within a family of amino acids that are related in their side chains. Whether a change in the amino acid sequence of a polypeptide of the invention results in a functional homolog can be readily determined by assessing the ability of the variant polypeptide to produce a response in cells in a fashion similar to the wild-type polypeptide.

"Fragment," with respect to a polynucleotide, refers to a clone or any part of a polynucleotide molecule, particularly a part of a polynucleotide that retains a usable, functional characteristic of the full-length polynucleotide molecule. Useful fragments include oligonucleotides and polynucleotides that may be used in hybridization or amplification technologies or in the regulation of replication, transcription or translation. A "polynucleotide fragment" refers to any subsequence of a polynucleotide SEQ ID NO, typically, comprising or consisting of at least about 9, 10, 11, 12 consecutive nucleotides from the polynucleotide SEQ ID NO, for example, at least about 30 nucleotides or at least about 50 nucleotides of any of the polynucleotide sequences provided herein. Exemplary fragments can additionally or alternatively include fragments that comprise, consist essentially of, or consist of a region that encodes a conserved family domain of a polypeptide. Exemplary fragments can additionally or alternatively include fragments that comprise a conserved domain of a polypeptide. As such, a fragment of a polynucleotide SEQ ID NO preferably means a nucleotide sequence that comprises or consists of the polynucleotide SEQ ID NO wherein no more than about 200, 150, 100, 50 or 25 consecutive nucleotides are missing, preferably no more than about 50 consecutive nucleotides are missing, and that retains a usable, functional characteristic (e.g., activity) of the full-length polynucleotide molecule that can be assessed by the skilled person through routine experimentation. Alternatively, a fragment of a polynucleotide SEQ ID NO preferably means a nucleotide sequence that comprises or consists of an amount of consecutive nucleotides from the polynucleotide SEQ ID NO and wherein the amount of consecutive nucleotides is at least 50.0%, 60.0%, 70.0%, 80.0%, 81.0%, 82.0%, 83.0%, 84.0%, 85.0%, 86.0%, 87.0%, 88.0%, 89.0%, 90.0%, 91.0%, 92.0%, 93.0%, 94.0%, 95.0%, 95.5%, 96.0%, 96.5%, 97.0%, 97.5%, 98.0%, 98.5%, 99.0%, 99.5%, 100%, preferably at least 80.0%, more preferably at least 85.0%, even more preferably at least 87.0%, even more preferably at least 90.0%, even more preferably at least 95.0%, most preferably at least 97.0%, of the full-length of the polynucleotide SEQ ID NO and retains a usable, functional characteristic (e.g., activity) of the full-length polynucleotide molecule that can be routinely assessed by the skilled person. As such, a fragment of a polynucleotide SEQ ID NO preferably means a nucleotide sequence that comprises or consists of the polynucleotide SEQ ID NO, wherein an amount of consecutive nucleotides is missing and wherein the amount is no more than 50.0%, 40.0%, 30.0% of the full-length of the polynucleotide SEQ ID NO, preferably no more than 20.0%, 15.0%, 10.0%, 9.0%, 8.0%, 7.0%, 6.0%, 5.0%, 4.5%, 4.0%, 3.5%, 3.0%, 2.5%, 2.0%, 1.5%, 1.0%, 0.5%, more preferably no more than 15.0%, even more preferably no more than 10.0%, even more preferably no more than 5.0%, most preferably no more than 2.5%, of the full-length of the polynucleotide SEQ ID NO and wherein the fragment retains a usable, functional characteristic (e.g., activity) of the full-length polynucleotide molecule that can be routinely assessed by the skilled person.

"Fragment," with respect to a polypeptide, refers to a subsequence of the polypeptide that performs at least one biological function of the intact polypeptide in substantially the same manner, or to a similar or greater extent, as does the intact polypeptide. A "subsequence of the polypeptide" or "a stretch of amino acid residues" as described herein refers to a sequence of contiguous amino acid residues derived from the polypeptide. For example, a polypeptide fragment can comprise a recognizable structural motif or functional domain such as a DNA-binding site or domain that binds to a DNA promoter region, an activation domain, or a domain for protein-protein interactions, and may initiate transcription. Fragments can vary in size from as few as 3 amino acid residues to the full length of the intact polypeptide, for example, at least about 10 amino acid residues in length, for example, at least about 20 amino acid residues in length, for example, at least about 30 amino acid residues in length, for example, at least about 100 amino acid residues in length, for example, at least about 150 amino acid residues in length, for example, at least about 200 amino acid residues in length. As such, a fragment of a polypeptide SEQ ID NO (or UniProt ID) preferably means a polypeptide sequence that comprises or consists of the polypeptide SEQ ID NO (or UniProt ID) wherein no more than about 200, 150, 125, 100, 80, 60, 50, 40, 30, 20 or 15 consecutive amino acid residues are missing, preferably no more than about 100 consecutive amino acid residues are missing, more preferably no more than about 50 consecutive amino acid residues are missing, even more preferably no more than about 40 consecutive amino acid residues are missing, and performs at least one biological function of the intact polypeptide in substantially the same manner, preferably to a similar or greater extent, as does the intact polypeptide that can be routinely assessed by the skilled person. Alternatively, a fragment of a polypeptide SEQ ID NO (or UniProt ID) preferably means a polypeptide sequence that comprises or consists of an amount of consecutive amino acid residues from the polypeptide SEQ ID NO (or UniProt ID) and wherein the amount of consecutive amino acid residues is at least 50.0%, 60.0%, 70.0%, 80.0%, 81.0%, 82.0%, 83.0%, 84.0%, 85.0%, 86.0%, 87.0%, 88.0%, 89.0%, 90.0%, 91.0%, 92.0%, 93.0%, 94.0%, 95.0%, 95.5%, 96.0%, 96.5%, 97.0%, 97.5%, 98.0%, 98.5%, 99.0%, 99.5%, 100%, preferably at least 80.0%, more preferably at least 85.0%, even more preferably at least 87.0%, even more preferably at least 90.0%, even more preferably at least 95.0%, most preferably at least 97.0% of the full-length of the polypeptide SEQ ID NO (or UniProt ID) and that performs at least one biological function of the intact polypeptide in substantially the same manner, preferably to a similar or greater extent, as does the intact polypeptide that can be routinely assessed by the skilled person. As such, a fragment of a polypeptide SEQ ID NO (or UniProt ID) preferably means a polypeptide sequence that comprises or consists of the polypeptide SEQ ID NO (or UniProt ID), wherein an amount of consecutive amino acid residues is missing and wherein the amount is no more than 50.0%, 40.0%, 30.0% of the full-length of the polypeptide SEQ ID NO (or UniProt ID), preferably no more than 20.0%, 15.0%, 10.0%, 9.0%, 8.0%, 7.0%, 6.0%, 5.0%, 4.5%, 4.0%, 3.5%, 3.0%, 2.5%, 2.0%, 1.5%, 1.0%, 0.5%, more preferably no more than 15.0%, even more preferably no more than 10.0%, even more preferably no more than 5.0%, most preferably no more than 2.5%, of the full-length of the polypeptide SEQ ID NO (or UniProt ID) and that performs at least one biological function of the intact polypeptide in substantially the same manner, preferably to a similar or greater extent, as does the intact polypeptide that can be routinely assessed by the skilled person.

Throughout this disclosure, the sequence of a polypeptide can be represented by a SEQ ID NO or alternatively by an UniProt ID. Therefore, the terms "polypeptide SEQ ID NO" and "polypeptide UniProt ID" can be interchangeably used, unless explicitly stated otherwise.

A "functional fragment" of a polypeptide has at least one property or activity of the polypeptide from which it is derived, preferably to a similar or greater extent. A functional fragment can, for example, include a functional domain or conserved domain of a polypeptide. It is understood that a polypeptide or a fragment thereof may have conservative amino acid substitutions that have substantially no effect on the polypeptide's activity. By conservative substitutions is intended substitutions of one hydrophobic amino acid for another or substitution of one polar amino acid for another or substitution of one acidic amino acid for another or substitution of one basic amino acid for another etc. Preferably, by conservative substitutions is intended combinations such as glycine by alanine and vice versa; valine, isoleucine and leucine by methionine and vice versa; aspartate by glutamate and vice versa; asparagine by glutamine and vice versa; serine by threonine and vice versa; lysine by arginine and vice versa; cysteine by methionine and vice versa; and phenylalanine and tyrosine by tryptophan and vice versa.

Homologous sequences as used herein describes those nucleotide sequences that have sequence similarity and encode polypeptides that share at least one functional characteristic such as a biochemical activity. More specifically, the term "functional homolog" as used herein describes those polypeptides that have sequence similarity (in other words, homology) and at the same time have at least one functional similarity such as a biochemical activity (Altenhoff et al., PLoS Comput. Biol. 8 (2012) e1002514).

Homologs can be identified by analysis of nucleotide and polypeptide sequence alignments. For example, performing a query on a database of nucleotide or polypeptide sequences can identify homologs of the nucleotides or polypeptides of interest. Sequence analysis can involve BLAST, Reciprocal BLAST, or PSI-BLAST analysis of non-redundant databases using the amino acid sequence of a reference polypeptide sequence. The amino acid sequence is, in some instances, deduced from the nucleotide sequence. Typically, those polypeptides in the database that have greater than 40% sequence identity to a polypeptide of interest are candidates for further evaluation for suitability as a homologous polypeptide. Amino acid sequence similarity allows for conservative amino acid substitutions, such as substitution of one hydrophobic residue for another or substitution of one polar residue for another or substitution of one acidic amino acid for another or substitution of one basic amino acid for another etc. Preferably, by conservative substitutions is intended combinations such as glycine by alanine and vice versa; valine, isoleucine and leucine by methionine and vice versa; aspartate by glutamate and vice versa; asparagine by glutamine and vice versa; serine by threonine and vice versa; lysine by arginine and vice versa; cysteine by methionine and vice versa; and phenylalanine and tyrosine by tryptophan and vice versa. If desired, manual inspection of such candidates can be carried out in order to narrow the number of candidates to be further evaluated.

A domain can be characterized, for example, by a Pfam (El-Gebali et al., Nucleic Acids Res. 47 (2019) D427-D432), an IPR (InterPro domain) (ebi.ac.uk/interpro) (Mitchell et al., Nucleic Acids Res. 47 (2019) D351-D360), a protein fingerprint domain (PRINTS) (Attwood et al., Nucleic Acids Res. 31 (2003) 400-402), a SUBFAM domain (Gough et al., J. Mol. Biol. 313 (2001) 903-919), a TIGRFAM domain (Selengut et al., Nucleic Acids Res. 35 (2007) D260-D264), a Conserved Domain Database (CDD) designation (www.ncbi.nlm.nih.gov/cdd)(Lu et al., Nucleic Acids Res. 48 (2020) D265-D268), a PTHR domain (www.pantherdb.org) (Mi et al., Nucleic Acids. Res. 41 (2013) D377-D386; Thomas et al., Genome Research 13 (2003) 2129-2141) or a PATRIC identifier or PATRIC DB global family domain (/www.patricbrc.org/) (Davis et al., Nucleic Acids Res. 48(D1) (2020) D606-D612). Protein or polypeptide sequence information and functional information can be provided by a comprehensive resource for protein sequence and annotation data like e.g., the Universal Protein Resource (UniProt) (www.uniprot.org) (Nucleic Acids Res. 2021, 49(D1), D480-D489). UniProt comprises the expertly and richly curated protein database called the UniProt Knowledgebase (UniProtKB), together with the UniProt Reference Clusters (UniRef) and the UniProt Archive (UniParc). The UniProt identifiers (UniProt ID) are unique for each protein present in the database. Throughout this disclosure, the sequence of a polypeptide is represented by a SEQ ID NO or an UniProt ID. Unless stated otherwise, the UniProt IDs of the proteins described correspond to their sequence version 01 as present in the UniProt Database (www.uniprot.org) version release 2021_03 and consulted on 9 Jun. 2021.

InterPro provides functional analysis of proteins by classifying them into families and predicting domains and important sites. To classify proteins in this way, InterPro uses predictive models, known as signatures, provided by several different databases (referred to as member databases) that make up the InterPro consortium. Protein signatures from these member databases are combined into a single searchable resource, capitalizing on their individual strengths to produce a powerful integrated database and diagnostic tool.

It should be understood for those skilled in the art that for the databases used herein, comprising Pfam 32.0 (released Sept 2018), CDD v3.17 (released 3 Apr. 2019), eggnogdb 4.5.1 (released Sept 2016), InterPro 82.0 (released 8 Oct. 2020) and PATRIC 3.6.9 (released March 2020), the content of each database is fixed at each release and is not to be changed. When the content of a specific database is changed, this specific database receives a new release version with a new release date. All release versions for each database with their corresponding release dates and specific content as annotated at these specific release dates are available and known to those skilled in the art.

The terms "identical" or "percent identity" or "% identity" in the context of two or more nucleic acid or polypeptide sequences, refer to two or more sequences or subsequences that are the same or have a specified percentage of nucleotides or amino acid residues that are the same, when compared and aligned for maximum correspondence, as measured using sequence comparison algorithms or by visual inspection. For sequence comparison, one sequence acts as a reference sequence, to which test sequences are compared. When using a sequence comparison algorithm, test and reference sequences are inputted into a computer, subsequence coordinates are designated, if necessary, and sequence algorithm program parameters are designated. The sequence comparison algorithm then calculates the % sequence identity for the test sequence(s) relative to the reference sequence, based on the designated program parameters. The percentage of sequence identity can be, preferably is, determined by alignment of the two sequences and identification of the number of positions with identical residues divided by the number of residues in the shorter of the sequences×100. Percent identity may be calculated globally over the full-length sequence of a given SEQ ID NO, i.e., the reference sequence, resulting in a global % identity score. Alternatively, % identity may be calculated over a partial sequence of the reference sequence, resulting in a local percent identity score. A partial sequence preferably means at least about 50%, 60%, 70%, 80%, 90% or 95% of the full-length reference sequence. In another preferred embodiment, a partial sequence of a reference polypeptide sequence means a stretch of at least 150 amino acid residues up to the total number of amino acid residues of a reference polypeptide sequence. In another more preferred embodiment, a partial sequence of a reference polypeptide sequence means a stretch of at least 200 amino acid residues up to the total number of amino acid residues of a reference polypeptide sequence. Using the full-length of the reference sequence in a local sequence alignment results in a global percent identity score between the test and the reference sequence.

Percent identity can be determined using different algorithms like, for example, BLAST and PSI-BLAST (Altschul et al., 1990, J Mol Biol 215:3, 403-410; Altschul et al., 1997, Nucleic Acids Res 25: 17, 3389-402), the Clustal Omega method (Sievers et al., 2011, Mol. Syst. Biol. 7:539), the MatGAT method (Campanella et al., 2003, BMC Bioinformatics, 4:29) or EMBOSS Needle.

As used herein, a polypeptide comprising or consisting of an amino acid sequence having 67.0% or more sequence identity over a stretch of at least 150 amino acid residues of a reference polypeptide sequence is to be understood as that the amino acid sequence 67.0%, 68.0%, 69.0%, 70.0%, 71.0%, 72.0%, 73.0%, 74.0%, 75.0%, 76.0%, 77.0%, 78.0%, 79.0%, 80.0%, 81.0%, 82.0%, 83.0%, 84.0%, 85.0%, 86.0%, 87.0%, 88.0%, 89.0%, 90.0%, 91.0%, 91.50%, 92.00%, 92.50%, 93.00%, 93.50%, 94.00%, 94.50%, 95.00%, 95.50%, 96.00%, 96.50%, 97.00%, 97.50%, 98.00%, 98.50%, 99.00%, 99.50%, 99.60%, 99.70%, 99.80%, 99.90%, 100% sequence identity over a stretch of at least 150 amino acid residues of the reference polypeptide sequence.

As used herein, a polypeptide comprising or consisting of an amino acid sequence having 67.0% or more sequence identity over a stretch of at least 200 amino acid residues of a reference polypeptide sequence is to be understood as that the amino acid sequence has 67.0%, 68.0%, 69.0%, 70.0%, 71.0%, 72.0%, 73.0%, 74.0%, 75.0%, 76.0%, 77.0%, 78.0%, 79.0%, 80.0%, 81.0%, 82.0%, 83.0%, 84.0%, 85.0%, 86.0%, 87.0%, 88.0%, 89.0%, 90.0%, 91.0%, 91.50%, 92.00%, 92.50%, 93.00%, 93.50%, 94.00%, 94.50%, 95.00%, 95.50%, 96.00%, 96.50%, 97.00%, 97.50%, 98.00%, 98.50%, 99.00%, 99.50%, 99.60%, 99.70%, 99.80%, 99.90%, 100% sequence identity over a stretch of at least 200 amino acid residues of the reference polypeptide sequence.

As used herein, a polypeptide comprising or consisting of an amino acid sequence having 55.0% or more sequence identity to the full-length sequence of a reference polypeptide sequence is to be understood as that the amino acid sequence has 55.0%, 56.0%, 57.0%, 58.0%, 59.0%, 60.0%, 61.0%, 62.0%, 63.0%, 64.0%, 65.0%, 66.0%, 67.0%, 68.0%, 69.0%, 70.0%, 71.0%, 72.0%, 73.0%, 74.0%, 75.0%, 76.0%, 77.0%, 78.0%, 79.0%, 80.0%, 81.0%, 82.0%, 83.0%, 84.0%, 85.0%, 86.0%, 87.0%, 88.0%, 89.0%, 90.0%, 91.0%, 91.50%, 92.00%, 92.50%, 93.00%, 93.50%, 94.00%, 94.50%, 95.00%, 95.50%, 96.00%, 96.50%, 97.00%, 97.50%, 98.00%, 98.50%, 99.00%, 99.50%, 99.60%, 99.70%, 99.80%, 99.90%, 100% sequence identity to the full-length of the amino acid sequence of the reference polypeptide sequence.

Throughout this disclosure, unless explicitly specified otherwise, a polypeptide comprising, consisting of or having an amino acid sequence having 55.0% or more sequence identity to the full-length amino acid sequence of a reference polypeptide, usually indicated with a SEQ ID NO or UniProt ID, preferably has 55.0%, 60.0%, 65.0%, 70.0%, 75.0%, 80.0%, 85.0%, 90.0%, 91.0%, 92.0%, 93.0%, 94.0%, 95.0%, 96.0%, 97.0%, 98.0% or 99.0%, more preferably has at least 60.0%, even more preferably has at least 65.0%, even more preferably has at least 70.0%, even more preferably has at least 80.0%, even more preferably has at least 85.0%, most preferably has at least 90.0%, sequence identity to the full length reference sequence. Additionally, unless explicitly specified otherwise, a polynucleotide sequence comprising, consisting of or having a nucleotide sequence having 55.0%, 60.0%, 65.0%, 70.0%, 75.0%, 80.0%, 85.0%, 90.0%, 91.0%, 92.0%, 93.0%, 94.0%, 95.0%, 96.0%, 97.0%, 98.0% or 99.0%, more preferably has at least 60.0%, even more preferably has at least 65.0%, even more preferably has at least 70.0%, even more preferably has at least 80.0%, even more preferably has at least 85.0%, most preferably has at least 90.0% sequence identity to the full-length reference sequence.

As used herein, a polypeptide comprising or consisting of an amino acid sequence having 85.0% or more sequence identity over a stretch of at least 150 amino acid residues of a reference polypeptide sequence is to be understood as that the amino acid sequence has 85.0%, 86.0%, 87.0%, 88.0%, 89.0%, 90.0%, 91.0%, 91.50%, 92.00%, 92.50%, 93.00%, 93.50%, 94.00%, 94.50%, 95.00%, 95.50%, 96.00%, 96.50%, 97.00%, 97.50%, 98.00%, 98.50%, 99.00%, 99.50%, 99.60%, 99.70%, 99.80%, 99.90%, 100% sequence identity over a stretch of at least 150 amino acid residues of the reference polypeptide sequence.

As used herein, a polypeptide comprising or consisting of an amino acid sequence having 85.0% or more sequence identity over a stretch of at least 200 amino acid residues of a reference polypeptide sequence is to be understood as that the amino acid sequence has 85.0%, 86.0%, 87.0%, 88.0%, 89.0%, 90.0%, 91.0%, 91.50%, 92.00%, 92.50%, 93.00%, 93.50%, 94.00%, 94.50%, 95.00%, 95.50%, 96.00%, 96.50%, 97.00%, 97.50%, 98.00%, 98.50%, 99.00%, 99.50%, 99.60%, 99.70%, 99.80%, 99.90%, 100% sequence identity over a stretch of at least 200 amino acid residues of the reference polypeptide sequence.

As used herein, a polypeptide comprising or consisting of an amino acid sequence having 80.0% or more sequence identity to the full-length sequence of a reference polypeptide sequence is to be understood as that the amino acid sequence has 80.0%, 81.0%, 82.0%, 83.0%, 84.0%, 85.0%, 86.0%, 87.0%, 88.0%, 89.0%, 90.0%, 91.0%, 91.50%, 92.00%, 92.50%, 93.00%, 93.50%, 94.00%, 94.50%, 95.00%, 95.50%, 96.00%, 96.50%, 97.00%, 97.50%, 98.00%, 98.50%, 99.00%, 99.50%, 99.60%, 99.70%, 99.80%, 99.90%, 100% sequence identity to the full-length of the amino acid sequence of the reference polypeptide sequence.

Throughout this disclosure, unless explicitly specified otherwise, a polypeptide comprising, consisting of or having an amino acid sequence having 80.0% or more sequence identity to the full-length amino acid sequence of a reference polypeptide, usually indicated with a SEQ ID NO or UniProt ID, preferably has 80.0%, 85.0%, 90.0%, 91.0%, 92.0%, 93.0%, 94.0%, 95.0%, 96.0%, 97.0%, 98.0% or 99.0%, more preferably has at least 85.0%, even more preferably has at least 90.0%, sequence identity to the full length reference sequence. Additionally, unless explicitly specified otherwise, a polynucleotide sequence comprising, consisting of or having a nucleotide sequence having 80.0%, 85.0%, 90.0%, 91.0%, 92.0%, 93.0%, 94.0%, 95.0%, 96.0%, 97.0%, 98.0% or 99.0%, more preferably has at least 85.0%, even more preferably has at least 90.0% sequence identity to the full-length reference sequence.

As used herein, a polypeptide comprising or consisting of an amino acid sequence having 60.0% or more sequence identity over a stretch of at least 150 amino acid residues of a reference polypeptide sequence is to be understood as that the amino acid sequence has 60.0%, 61.0%, 62.0%, 63.0%, 64.0%, 65.0%, 66.0%, 67.0%, 68.0%, 69.0%, 70.0%, 71.0%, 72.0%, 73.0%, 74.0%, 75.0%, 76.0%, 77.0%, 78.0%, 79.0%, 80.0%, 81.0%, 82.0%, 83.0%, 84.0%, 85.0%, 86.0%, 87.0%, 88.0%, 89.0%, 90.0%, 91.0%, 91.50%, 92.00%, 92.50%, 93.00%, 93.50%, 94.00%, 94.50%, 95.00%, 95.50%, 96.00%, 96.50%, 97.00%, 97.50%, 98.00%, 98.50%, 99.00%, 99.50%, 99.60%, 99.70%, 99.80%, 99.90%, 100% sequence identity over a stretch of at least 150 amino acid residues of the reference polypeptide sequence.

As used herein, a polypeptide comprising or consisting of an amino acid sequence having 60.0% or more sequence identity over a stretch of at least 200 amino acid residues of a reference polypeptide sequence is to be understood as that the amino acid sequence has 60.0%, 61.0%, 62.0%, 63.0%, 64.0%, 65.0%, 66.0%, 67.0%, 68.0%, 69.0%, 70.0%, 71.0%, 72.0%, 73.0%, 74.0%, 75.0%, 76.0%, 77.0%, 78.0%, 79.0%, 80.0%, 81.0%, 82.0%, 83.0%, 84.0%, 85.0%, 86.0%, 87.0%, 88.0%, 89.0%, 90.0%, 91.0%, 91.50%, 92.00%, 92.50%, 93.00%, 93.50%, 94.00%, 94.50%, 95.00%, 95.50%, 96.00%, 96.50%, 97.00%, 97.50%, 98.00%, 98.50%, 99.00%, 99.50%, 99.60%, 99.70%, 99.80%, 99.90%, 100% sequence identity over a stretch of at least 200 amino acid residues of the reference polypeptide sequence.

As used herein, a polypeptide comprising or consisting of an amino acid sequence having 45.0% or more sequence identity to the full-length sequence of a reference polypeptide sequence is to be understood as that the amino acid sequence has 45.0%, 46.0%, 47.0%, 48.0%, 49.0%, 50.0%, 51.0%, 52.0%, 53.0%, 54.0%, 55.0%, 56.0%, 57.0%, 58.0%, 59.0%, 60.0%, 61.0%, 62.0%, 63.0%, 64.0%, 65.0%, 66.0%, 67.0%, 68.0%, 69.0%, 70.0%, 71.0%, 72.0%, 73.0%, 74.0%, 75.0%, 76.0%, 77.0%, 78.0%, 79.0%, 80.0%, 81.0%, 82.0%, 83.0%, 84.0%, 85.0%, 86.0%, 87.0%, 88.0%, 89.0%, 90.0%, 91.0%, 91.50%, 92.00%, 92.50%, 93.00%, 93.50%, 94.00%, 94.50%, 95.00%, 95.50%, 96.00%, 96.50%, 97.00%, 97.50%, 98.00%, 98.50%, 99.00%, 99.50%, 99.60%, 99.70%, 99.80%, 99.90%, 100% sequence identity to the full-length of the amino acid sequence of the reference polypeptide sequence.

Throughout this disclosure, unless explicitly specified otherwise, a polypeptide comprising, consisting of or having an amino acid sequence having 45.0% or more sequence identity to the full-length amino acid sequence of a reference polypeptide, usually indicated with a SEQ ID NO or UniProt ID, preferably has 45.0%, 46.0%, 47.0%, 48.0%, 49.0%, 50.0%, 51.0%, 52.0%, 53.0%, 54.0%, 55.0%, 56.0%, 57.0%, 58.0%, 59.0%, 60.0%, 61.0%, 62.0%, 63.0%, 64.0%, 65.0%, 66.0%, 67.0%, 68.0%, 69.0%, 70.0%, 71.0%, 72.0%, 73.0%, 74.0%, 75.0%, 76.0%, 77.0%, 78.0%, 79.0%, 80.0%, 85.0%, 90.0%, 91.0%, 92.0%, 93.0%, 94.0%, 95.0%, 96.0%, 97.0%, 98.0% or 99.0%, more preferably has at least 50.0%, more preferably has at least 55.0%, more preferably has at least 60.0%, more preferably has at least 65.0%, more preferably has at least 70.0%, more preferably has at least 75.0%, more preferably has at least 80.0%, more preferably has at least 85.0%, even more preferably has at least 90.0%, sequence identity to the full length reference sequence. Additionally, unless explicitly specified otherwise, a polynucleotide sequence comprising, consisting of or having a nucleotide sequence having 45.0%, 50.0%, 55.0%, 60.0%, 65.0%, 70.0%, 75.0%, 80.0%, 85.0%, 90.0%, 91.0%, 92.0%, 93.0%, 94.0%, 95.0%, 96.0%, 97.0%, 98.0% or 99.0%, more preferably has at least 85.0%, even more preferably has at least 90.0% sequence identity to the full-length reference sequence.

For the purposes of this invention, percent identity is determined using MatGAT2.01 (Campanella et al., 2003, BMC Bioinformatics 4:29). The following default parameters for protein are employed: (1) Gap cost Existence: 12 and Extension: 2; (2) The Matrix employed was BLOSUM50. In a preferred embodiment, sequence identity is calculated based on the full-length sequence of a given SEQ ID NO, i.e., the reference sequence, or a part thereof. Part thereof preferably means at least 50%, 60%, 70%, 80%, 90% or 95% of the complete reference sequence.

The terms "sialic acid," "N-acetylneuraminate," "N-acylneuraminate," "N-acetylneuraminic acid" are used interchangeably and refer to an acidic sugar comprising but not limited to Neu4Ac; Neu5Ac; Neu4,5Ac2; Neu5,7Ac2; Neu5,8Ac2; Neu5,9Ac2; Neu4,5,9Ac3; Neu5,7,9Ac3; Neu5,8,9Ac3; Neu4,5,7,9Ac4; Neu5,7,8,9Ac4; Neu4,5,7,8,9Ac5; Neu5Gc and 2-keto-3-deoxymanno-octulonic acid (KDO).

Neu4Ac is also known as 4-O-acetyl-5-amino-3,5-dideoxy-D-glycero-D-galacto-non-2-ulopyranosonic acid or 4-O-acetyl neuraminic acid and has $C_{11}H_{19}NO_9$ as molecular formula. Neu5Ac is also known as 5-acetamido-3,5-dideoxy-D-glycero-D-galacto-non-2-ulopyranosonic acid, D-glycero-5-acetamido-3,5-dideoxy-D-galacto-non-2-ulo-pyranosonic acid, 5-(acetylamino)-3,5-dideoxy-D-glycero-D-galacto-2-nonulopyranosonic acid, 5-(acetylamino)-3,5-dideoxy-D-glycero-D-galacto-2-nonulosonic acid, 5-(acetylamino)-3,5-dideoxy-D-glycero-D-galacto-non-2-nonulosonic acid or 5-(acetylamino)-3,5-dideoxy-D-glycero-D-galacto-non-2-ulopyranosonic acid and has $C_{11}H_{19}NO_9$ as molecular formula. Neu4,5Ac2 is also known as N-acetyl-4-O-acetylneuraminic acid, 4-O-acetyl-N-acetylneuraminic acid, 4-O-acetyl-N-acetylneuraminate, 4-acetate 5-acetamido-3,5-dideoxy-D-glycero-D-galacto-nonulosonate, 4-acetate 5-(acetylamino)-3,5-dideoxy-D-glycero-D-galacto-2-nonulosonate, 4-acetate 5-acetamido-3,5-dideoxy-D-glycero-D-galacto-nonulosonic acid or 4-acetate 5-(acetylamino)-3,5-dideoxy-D-glycero-D-galacto-2-nonulosonic acid and has $C_{13}H_{21}NO_{10}$ as molecular formula. Neu5,7Ac2 is also known as 7-O-acetyl-N-acetylneuraminic acid, N-acetyl-7-0-acetylneuraminic acid, 7-O-acetyl-N-acetylneuraminate, 7-acetate 5-acetamido-3,5-dideoxy-D-glycero-D-galacto-nonulosonate, 7-acetate 5-(acetylamino)-3,5-dideoxy-D-glycero-D-galacto-2-nonulosonate, 7-acetate 5-acetamido-3,5-dideoxy-D-glycero-D-galacto-nonulosonic acid or 7-acetate 5-(acetylamino)-3,5-dideoxy-D-glycero-D-galacto-2-nonulosonic acid and has $C_{13}H_{21}NO_{10}$ as molecular formula. Neu5,8Ac2 is also known as 5-n-acetyl-8-o-acetyl neuraminic acid and has $C_{13}H_{21}NO_{10}$ as molecular formula. Neu5,9Ac2 is also known as N-acetyl-9-O-acetylneuraminic acid, 9-anana, 9-O-acetylsialic acid, 9-O-acetyl-N-acetylneuraminic acid, 5-n-acetyl-9-O-acetyl neuraminic acid, N,9-O-diacetylneuraminate or N,9-O-diacetylneuraminate and has $C_{13}H_{21}NO_{10}$ as molecular formula. Neu4,5,9Ac3 is also known as 5-N-acetyl-4,9-di-O-acetylneuraminic acid. Neu5,7,9Ac3 is also known as 5-N-acetyl-7,9-di-0-acetylneuraminic acid. Neu5,8,9Ac3 is also known as 5-N-acetyl-8,9-di-O-acetylneuraminic acid. Neu4,5,7,9Ac4 is also known as 5-N-acetyl-4,7,9-tri-O-acetylneuraminic acid. Neu5,7,8,9Ac4 is also known as 5-N-acetyl-7,8,9-tri-O-acetylneuraminic acid. Neu4,5,7,8,9Ac5 is also known as 5-N-acetyl-4,7,8,9-tetra-O-acetylneuraminic acid. Neu5Gc is also known as N-glycolyl-neuraminic acid, N-glycolylneuraminic acid, N-glycolylneuraminate, N-glycoloyl-neuraminate, N-glycoloyl-neuraminic acid, N-glycoloylneuraminic acid, 3,5-dideoxy-5-((hydroxyacetyl)amino)-D-glycero-D-galacto-2-nonulosonic acid, 3,5-dideoxy-5-(glycoloylamino)-D-glycero-D-galacto-2-nonulopyranosonic acid, 3,5-dideoxy-5-(glycoloylamino)-D-glycero-D-galacto-non-2-ulopyranosonic acid, 3,5-dideoxy-5-[(hydroxyacetyl)amino]-D-glycero-D-galacto-non-2-ulopyranosonic acid, D-glycero-5-glycolylamido-3,5-dideoxy-D-galacto-non-2-ulo-pyranosonic acid and has C11H19NO10 as molecular formula. 2-keto-3-deoxy-manno-octulonic acid is also known as KDO, Kdo, kdo, 2-keto-3-deoxy-D-mannooctanoic acid, 2-oxo-3-deoxy-D-mannooctonic acid, 3-deoxy-D-manno-2-octulosonic acid, 3-deoxy-D-manno-oct-2-ulo-pyranosonic acid, 3-deoxy-D-manno-oct-2-ulosonic acid, 3-deoxy-D-manno-octulosonic acid, 3-deoxy-D-manno-oct-2-ulopyranosonic acid, ketodeoxyoctonic acid, ketodeoxyoctulonic acid, (6R)-6-(hydroxymethyl)-1-carboxy-2-deoxy-D-lyxo-hexopyranose, keto-deoxy-octulonic acid and has C8H14O8 as molecular formula.

The term "glycosyltransferase" as used herein refers to an enzyme capable to catalyze the transfer of a sugar moiety of a donor to a specific acceptor, forming glycosidic bonds. The donor can be a precursor as defined herein. A classification of glycosyltransferases using nucleotide diphospho-sugar, nucleotide monophospho-sugar and sugar phosphates and related proteins into distinct sequence-based families has been described (Campbell et al., Biochem. J. 326, 929-939 (1997)) and is available on the CAZy (CArbohydrate-Active EnZymes) website (www.cazy.org).

As used herein the glycosyltransferase can be selected from the list comprising but not limited to: fucosyltransferases, sialyltransferases, galactosyltransferases, glucosyltransferases, mannosyltransferases, N-acetylglucosaminyltransferases, N-acetylgalactosaminyltransferases, N-acetylmannosaminyltransferases, xylosyltransferases, glucuronyltransferases, galacturonyltransferases, glucosaminyltransferases, N-glycolylneuraminyltransferases, rhamnosyltransferases, N-acetylrhamnosyltransferases, UDP-4-amino-4,6-dideoxy-N-acetyl-beta-L-altrosamine transaminases, UDP-N-acetylglucosamine enolpyruvyl transferases and fucosaminyltransferases.

Sialyltransferases are glycosyltransferases that transfer a sialic acid (like Neu5Ac) from a donor (like CMP-Neu5Ac) onto an acceptor. Sialyltransferases comprise alpha-2,3-sialyltransferases, alpha-2,6-sialyltransferases and alpha-2,8-sialyltransferases that catalyze the transfer of a sialic acid onto an acceptor via alpha-glycosidic bonds. Sialyltransferases can be found but are not limited to the GT29, GT42, GT52, GT80, GT97 and GT100 CAZy families.

The term "monosaccharide" as used herein refers to a sugar that is not decomposable into simpler sugars by hydrolysis, is classed either an aldose or ketose, and contains one or more hydroxyl groups per molecule. Monosaccharides are saccharides containing only one simple sugar.

The term "phosphorylated monosaccharide" as used herein refers to a monosaccharide that is phosphorylated. Examples of phosphorylated monosaccharides include but are not limited to glucose-1-phosphate, glucose-6-phosphate, glucose-1,6-bisphosphate, galactose-1-phosphate, fructose-6-phosphate, fructose-1,6-bisphosphate, fructose-1-phosphate, glucosamine-1-phosphate, glucosamine-6-phosphate, N-acetylglucosamine-1-phosphate, mannose-1-phosphate, mannose-6-phosphate or fucose-1-phosphate. Some, but not all, of these phosphorylated monosaccharides are precursors or intermediates for the production of activated monosaccharide.

The terms "activated monosaccharide," "nucleotide-activated sugar," "nucleotide-sugar," "activated sugar," "nucleoside" or "nucleotide donor" are used herein interchangeably and refer to activated forms of monosaccharides. Examples of activated monosaccharides include but are not limited to UDP-N-acetylglucosamine (UDP-GlcNAc), UDP-N-acetylgalactosamine (UDP-GalNAc), UDP-N-acetylmannosamine (UDP-ManNAc), UDP-glucose (UDP-Glc), UDP-galactose (UDP-Gal), GDP-mannose (GDP-Man), UDP-glucuronate, UDP-galacturonate, UDP-2-acetamido-2,6-dideoxy-L-arabino-4-hexulose, UDP-2-acetamido-2,6-dideoxy-L-lyxo-4-hexulose, UDP-N-acetyl-L-rhamnosamine (UDP-L-RhaNAc or UDP-2-acetamido-2,6-dideoxy-L-mannose), dTDP-N-acetylfucosamine, UDP-N-acetylfucosamine (UDP-L-FucNAc or UDP-2-acetamido-2,6-dideoxy-L-galactose), UDP-N-acetyl-L-pneumosamine (UDP-L-PneNAC or UDP-2-acetamido-2,6-dideoxy-L-talose), UDP-N-acetylmuramic acid, UDP-N-acetyl-L-quinovosamine (UDP-L-QuiNAc or UDP-2-acetamido-2,6-dideoxy-L-glucose), GDP-L-quinovose, CMP-sialic acid, GDP-fucose (GDP-Fuc), GDP-rhamnose and UDP-xylose. Nucleotide-sugars act as glycosyl donors in glycosylation reactions. Glycosylation reactions are reactions that are catalyzed by glycosyltransferases.

The term "CMP-sialic acid" as used herein refers to a nucleotide-activated form of sialic acid comprising but not limited to CMP-Neu5Ac, CMP-Neu4Ac, CMP-Neu5Ac9N$_3$, CMP-Neu4,5Ac2, CMP-Neu5,7Ac2, CMP-Neu5,9Ac2, CMP-Neu5,7(8,9)Ac2, CMP-N-glycolylneuraminic acid (CMP-Neu5Gc) and CMP-KDO.

The term "disaccharide" as used herein refers to a saccharide polymer containing two simple sugars, i.e., monosaccharides. Examples of disaccharides comprise lactose (Gal-b1,4-Glc), lacto-N-biose (Gal-b1,3-GlcNAc), N-acetyllactosamine (Gal-b1,4-GlcNAc), LacDiNAc (GalNAc-b1,4-GlcNAc), N-acetylgalactosaminylglucose (GalNAc-b1,4-Glc), Neu5Ac-a2,3-Gal, Neu5Ac-a2,6-Gal, fucopyranosyl-(1-4)-N-glycolylneuraminic acid (Fuc-(1-4)-Neu5Gc), sucrose (Glc-a1,2-Fru), maltose (Glc-a1,4-Glc) and melibiose (Gal-a1,6-Glc).

"Oligosaccharide" as the term is used herein and as generally understood in the state of the art, refers to a saccharide polymer containing a small number, typically three to twenty, preferably three to ten, of simple sugars, i.e., monosaccharides. The oligosaccharide as used in this disclosure can be a linear structure or can include branches. The linkage (e.g., glycosidic linkage, galactosidic linkage, glucosidic linkage, etc.) between two sugar units can be expressed, for example, as 1,4, 1→4, or (1-4), used interchangeably herein. For example, the terms "Gal-b1,4-Glc," "Gal-b1,4-Glc," "b-Gal-1→4)-Glc," "b-Gal-(1→4)-Glc," "Galbeta1-4-Glc," "Gal-b(1-4)-Glc" and "Gal-b(1-4)-Glc" have the same meaning, i.e., a beta-glycosidic bond links carbon-1 of galactose (Gal) with the carbon-4 of glucose (Glc). Each monosaccharide can be in the cyclic form (e.g., pyranose or furanose form). Linkages between the individual monosaccharide units may include alpha 1→2, alpha 1→3, alpha 1→4, alpha 1→6, alpha 2→1, alpha 2→3, alpha 2→4, alpha 2→6, beta 1→2, beta 1→3, beta 1→4, beta 1→6, beta 2→1, beta 2→3, beta 2→4, and beta 2->6. An oligosaccharide can contain both alpha- and beta-glycosidic bonds or can contain only alpha-glycosidic or only beta-glycosidic bonds. The term "polysaccharide" refers to a compound consisting of a large number, typically more than twenty, of monosaccharides linked glycosidically.

Examples of oligosaccharides include but are not limited to Lewis-type antigen oligosaccharides, mammalian (including human) milk oligosaccharides, O-antigen, enterobacterial common antigen (ECA), the glycan chain present in lipopolysaccharides (LPS), the oligosaccharide repeats present in capsular polysaccharides, peptidoglycan (PG), amino-sugars, antigens of the human ABO blood group system, neutral (non-charged) oligosaccharides, negatively charged oligosaccharides, fucosylated oligosaccharides, sialylated oligosaccharides, N-acetylglucosamine containing oligosaccharides, N-acetyllactosamine containing oligosaccharides, lacto-N-biose containing oligosaccharides, lactose containing oligosaccharides, non-fucosylated neutral (non-charged) oligosaccharides, N-acetyllactosamine containing fucosylated oligosaccharides, N-acetyllactosamine non-fucosylated oligosaccharides, lacto-N-biose containing fucosylated oligosaccharides, lacto-N-biose containing non-fucosylated oligosaccharides, N-acetyllactosamine containing negatively charged oligosaccharides, lacto-N-biose containing negatively charged oligosaccharides, animal oligosaccharides, preferably selected from the group consisting of N-glycans and O-glycans, and plant oligosaccharides, preferably selected from the group consisting of N-glycans and O-glycans.

As used herein, a 'sialylated oligosaccharide' is to be understood as a negatively charged sialic acid containing oligosaccharide, i.e., an oligosaccharide having a sialic acid residue. It has an acidic nature. Such sialylated oligosaccharide is a saccharide structure comprising at least three monosaccharide subunits linked to each other via glycosidic bonds, wherein at least one of the monosaccharide subunit is a sialic acid residue. A sialylated oligosaccharide can contain more than one sialic acid residue, e.g., two, three or more. The more than one sialic acid residue can be two, three or more identical sialic acid residues. The more than one sialic acid residue can also be two, three or more different sialic acid residues. For example, a sialylated oligosaccharide can contain one or more Neu5Ac residues and one or more KDO residues. Some examples are 3-SL (3'-sialyllactose or 3'SL or Neu5Ac-a2,3-Gal-b1,4-Glc), 3'-sialyllactosamine, 6-SL (6'sialyllactose, 6'-sialyllactose or 6'SL or Neu5Ac-a2,6-Gal-b1,4-Glc), 3,6-disialyllactose (Neu5Ac-a2,3-(Neu5Ac-a2,6)-Gal-b1,4-Glc), 6,6'-disialyllactose (Neu5Ac-a2,6-Gal-b1,4-(Neu5Ac-a2,6)-Glc), 8,3-disialyllactose (Neu5Ac-a2,8-Neu5Ac-a2,3-Gal-b1,4-Glc), 6'-sialyllactosamine, oligosaccharides comprising 6'sialyllactose (also known as 6'sialyllactose, 6'SL and 6'-SL), SGG hexasaccharide (Neu5Acα-2,3Galβ-1,3GalNacβ-1,3Galα-1,4Galβ-1,4Gal), sialylated tetrasaccharide (Neu5Acα-2,3Galβ-1,4GlcNacβ-14GlcNAc), pentasaccharide LSTD (Neu5Acα-2,3Galβ-1,4GlcNacβ-1,3Galβ-1,4Glc), sialylated lacto-N-triose, sialylated lacto-N-tetraose, sialyllacto-N-neotetraose, LSTc (Neu5Ac-a2,6-Gal-b1,4-GlcNAc-b1,3-Gal-b1,4-Glc), monosialyllacto-N-hexaose, disialyllacto-N-hexaose I, monosialyllacto-N-hexaose I, monosialyllacto-N-neohexaose II, disialyllacto-N-neohexaose, disialyllacto-N-tetraose, disialyllacto-N-hexaose II, sialyllacto-N-tetraose a, disialyllacto-N-hexaose I, sialyllacto-N-tetraose b, 3'-sialyl-3-fucosyllactose, disialomonofucosyllacto-N-neohexaose, monofucosylmonosialyllacto-N-octaose (sialyl Lea), sialyllacto-N-fucohexaose IL, disialyllacto-N-fucopentaose II, monofucosyldisialyllacto-N-tetraose, 3'-KDO-lactose, 3'-KDO-lactosamine, 3'-KDO-6'sialyllactose, 3'KDO-8-sialyllactose, KDO-2,3Galβ-1,3GalNacβ-1,3Galα-1,4Galβ-1,4Gal, KDO-2,3Galβ-1, 3GlcNacβ-1,3Galβ-1,4Glc, KDO-2,3Galβ-1,4GlcNacβ-1, 3Galβ-1,4Glc, 3'-KDO-3-fucosyllactose and oligosaccharides bearing one or several sialic acid residue (s), including but not limited to: oligosaccharide moieties of the gangliosides selected from GM3 (3'sialyllactose, Neu5Acα-2,3Galβ-4Glc) and oligosaccharides comprising the GM3 motif, GD3 Neu5Acα-2,8Neu5Acα-2,3Galβ-1,4Glc GT3 (Neu5Acα-2,8Neu5Acα-2,8Neu5Acα-2,3Galβ-1,4Glc); GM2 GalNAcβ-1,4(Neu5Acα-2,3)Galβ-1,4Glc, GM1 Galβ-1,3GalNAcβ-1,4(Neu5Acα-2,3)Galβ-1,4Glc, GD1a Neu5Acα-2,3Galβ-1,3GalNAcβ-1,4(Neu5Acα-2,3) Galβ-1,4Glc, GT1a Neu5Acα-2,8Neu5Acα-2,3Galβ-1, 3GalNAcβ-1,4(Neu5Acα-2,3)Galβ-1,4Glc, GD2 GalNAcβ-1,4(Neu5Acα-2,8Neu5Acα2,3)Galβ-1,4Glc, GT2 GalNAcβ-1,4(Neu5Acα-2,8Neu5Acα-2,8Neu5Acα2,3) Galβ-1,4Glc, GD1b, Galβ-1,3GalNAcβ-1,4(Neu5Acα-2, 8Neu5Acα2,3)Galβ-1,4Glc, GT1b Neu5Acα-2,3Galβ-1, 3GalNAcβ-1,4(Neu5Acα-2,8Neu5Acα2,3)Galβ-1,4Glc, GQ1b Neu5Acα-2,8Neu5Acα-2,3Galβ-1,3GalNAcβ-1,4 (Neu5Acα-2,8Neu5Acα2,3)Galβ-1,4Glc, GT1c Galβ-1, 3GalNAcβ-1,4(Neu5Acα-2,8Neu5Acα-2,8Neu5Acα2,3) Galβ-1,4Glc, GQ1c Neu5Acα-2,3Galβ-1,3GalNAcβ-1,4 (Neu5Acα-2,8Neu5Acα-2,8Neu5Acα2,3)Galβ-1,4Glc, GP1c Neu5Acα-2,8Neu5Acα-2,3Galβ-1,3GalNAcβ-1,4 (Neu5Acα-2,8Neu5Acα-2,8Neu5Acα2,3)Galβ-1,4Glc, GD1a Neu5Acα-2,3Galβ-1,3(Neu5Acα-2,6)GalNAcβ-1, 4Galβ-1,4Glc, Fucosyl-GM1 Fucα-1,2Galβ-1,3GalNAcβ-1, 4(Neu5Acα-2,3)Galβ-1,4Glc; all of which may be extended to the production of the corresponding gangliosides by reacting the above oligosaccharide moieties with ceramide or synthetizing the above oligosaccharides on a ceramide.

As used herein, a '3'sialylated oligosaccharide' is to be understood as a negatively charged sialic acid containing oligosaccharide comprising an oligosaccharide or disaccharide that is alpha-2,3-glycosidically linked to a sialic acid residue. It has an acidic nature.

Such sialylated oligosaccharide is a saccharide structure comprising at least three monosaccharide subunits linked to each other via glycosidic bonds, wherein at least one of the monosaccharide subunit is an alpha-2,3-glycosydically linked sialic acid residue. A 3'sialylated oligosaccharide can contain more than one sialic acid residue, e.g., two, three or more. The more than one sialic acid residue can be two, three or more identical sialic acid residues. The more than one sialic acid residue can also be two, three or more different sialic acid residues. For example, a 3'sialylated oligosaccharide can contain one or more Neu5Ac residues and one or more KDO residues. Some examples are 3-SL (3'-sialyllactose or 3'SL or Neu5Ac-a2,3-Gal-b1,4-Glc), 3'-sialyllactosamine, 3,6-disialyllactose (Neu5Ac-a2,3-(Neu5Ac-a2,6)-Gal-b1,4-Glc), 8,3-disialyllactose (Neu5Ac-a2,8-Neu5Ac-a2,3-Gal-b1,4-Glc), SGG hexasaccharide (Neu5Acα-2, 3Galβ-1,3GalNacβ-1,3Galα-1,4Galβ-1,4Gal), sialylated tetrasaccharide (Neu5Acα-2,3Galβ-1,4GlcNacβ-14GlcNAc), pentasaccharide LSTD (Neu5Acα-2,3Galβ-1, 4GlcNacβ-1,3Galβ-1,4Glc), 3'sialylated lacto-N-triose, 3'sialylated lacto-N-tetraose (e.g., Neu5Acα-2,3Galβ-1, 3GlcNAcβ-1,3Galβ-1,4Glc (LSTa); KDOα-2,3Galβ-1, 3GlcNAcβ-1,3Galβ-1,4Glc), sialyllacto-N-neotetraose (e.g., Neu5Acα-2,3Galβ-1,4GlcNacβ-1,3Galβ-1,4Glc (LSTd)), monosialyllacto-N-hexaose, disialyllacto-N- hexaose I, monosialyllacto-N-neohexaose I, monosialyl-lacto-N-neohexaose II, disialyllacto-N-neohexaose, disialyllacto-N-tetraose, disialyllacto-N-hexaose II, sialyl-lacto-N-tetraose a, disialyllacto-N-hexaose I, 3'-sialyl-3-fucosyllactose, disialomonofucosyllacto-N-neohexaose, monofucosylmonosialyllacto-N-octaose (sialyl Lea), sialyl-lacto-N-fucohexaose II, disialyllacto-N-fucopentaose II, monofucosyldisialyllacto-N-tetraose, 3'-KDO-lactose, 3'-KDO-lactosamine, 3'-KDO-6'sialyllactose, 3'KDO-8-sialyllactose, KDO-2,3Galβ-1,3GalNacβ-1,3Galα-1,4Galβ-1,4Gal, KDO-2,3Galβ-1,3GlcNacβ-1,3Galβ-1,4Glc, KDO-2,3Galβ-1,4GlcNacβ-1,3Galβ-1,4Glc, 3'-KDO-3-fucosyllactose and oligosaccharides bearing one or several sialic acid residue(s), including but not limited to: oligosaccharide moieties of the gangliosides selected from GM3 (3'sialyllactose, Neu5Acα-2,3Galβ-4Glc) and oligosaccharides comprising the GM3 motif, GD3 (Neu5Acα-2,8Neu5Acα-2,3Galβ-1,4Glc), GT3 (Neu5Acα-2,8Neu5Acα-2,8Neu5Acα-2,3Galβ-1,4Glc); GM2 GalNAcβ-1,4(Neu5Acα-2,3)Galβ-1,4Glc, GM1 Galβ-1,3GalNAcβ-1,4(Neu5Acα-2,3)Galβ-1,4Glc, GD1a Neu5Acα-2,3Galβ-1,3GalNAcβ-1,4(Neu5Acα-2,3)Galβ-1,4Glc, GT1a Neu5Acα-2,8Neu5Acα-2,3Galβ-1,3GalNAcβ-1,4 (Neu5Acα-2,3)Galβ-1,4Glc, GD2 GalNAcβ-1,4(Neu5Acα-2,8Neu5Acα2,3)Galβ-1,4Glc, GT2 GalNAcβ-1,4 (Neu5Acα-2,8Neu5Acα-2,8Neu5Acα2,3)Galβ-1,4Glc, GD1b, Galβ-1,3GalNAcβ-1,4(Neu5Acα-2,8Neu5Acα2,3) Galβ-1,4Glc, GT1b Neu5Acα-2,3Galβ-1,3GalNAcβ-1,4 (Neu5Acα-2,8Neu5Acα2,3)Galβ-1,4Glc, GQ1b Neu5Acα-2,8Neu5Acα-2,3Galβ-1,3GalNAcβ-1,4(Neu5Acα-2, 8Neu5Acα2,3)Galβ-1,4Glc, GT1c Galβ-1,3GalNAcβ-1,4 (Neu5Acα-2,8Neu5Acα-2,8Neu5Acα2,3)Galβ-1,4Glc, GQ1c Neu5Acα-2,3Galβ-1,3GalNAcβ-1,4(Neu5Acα-2,8Neu5Acα-2,8Neu5Acα2,3)Galβ-1,4Glc, GP1c Neu5Acα-2,8Neu5Acα-2,3Galβ-1,3GalNAcβ-1,4(Neu5Acα-2, 8Neu5Acα-2,8Neu5Acα2,3)Galβ-1,4Glc, GD1α Neu5Acα-2,3Galβ-1,3(Neu5Acα-2,6)GalNAcβ-1,4Galβ-1,4Glc, Fucosyl-GM1 Fucα-1,2Galβ-1,3GalNAcβ-1,4(Neu5Acα-2, 3)Galβ-1,4Glc; all of which may be extended to the production of the corresponding gangliosides by reacting the above oligosaccharide moieties with ceramide or synthetizing the above oligosaccharides on a ceramide.

A 'neutral oligosaccharide' or a 'non-charged oligosaccharide' as used herein and as generally understood from the state of the art is an oligosaccharide that has no negative charge originating from a carboxylic acid group. Examples of such neutral oligosaccharide are 2'-fucosyllactose (2'FL), 3-fucosyllactose (3FL), 2', 3-difucosyllactose (diFL), lacto-N-triose II (LN3), lacto-N-tetraose (LNT), lacto-N-neotetraose (LNnT), lacto-N-fucopentaose I (LNFP I), lacto-N-neofucopentaose I (LNnFP I), lacto-N-fucopentaose II (LNFP II), lacto-N-fucopentaose III (LNFP III), lacto-N-fucopentaose V (LNFP V), lacto-N-fucopentaose VI, lacto-N-neofucopentaose V (LNnFP V), lacto-N-difucohexaose I (LNDFH I), lacto-N-difucohexaose II (LNDFH II), 6'-galactosyllactose, 3'-galactosyllactose, lacto-N-hexaose, lacto-N-neohexaose, para-lacto-N-hexaose, para-lacto-N-neohexaose, fucosyl-lacto-N-hexaose, difucosyl-lacto-N-hexaose, difucosyl-lacto-N-neohexaose (LNnDFH II), difucosyl-para-lacto-N-neohexaose, trifucosyllacto-N-hexaose, para-lacto-N-fucohexaose and lacto-N-trifucoheptaose.

Mammalian milk oligosaccharides or MMOs comprise oligosaccharides present in milk found in any phase during lactation including colostrum milk from humans (i.e., human milk oligosaccharides or HMOs) and mammals including but not limited to cows (*Bos Taurus*), sheep (*Ovis aries*), goats (*Capra aegagrus hircus*), bactrian camels (*Camelus bactrianus*), horses (*Equus ferus caballus*), pigs (*Sus scropha*), dogs (*Canis lupus familiaris*), ezo brown bears (*Ursus arctos yesoensis*), polar bear (*Ursus maritimus*), Japanese black bears (*Ursus thibetanus japonicus*), striped skunks (*Mephitis mephitis*), hooded seals (*Cystophora cristata*), Asian elephants (*Elephas maximus*), African elephant (*Loxodonta africana*), giant anteater (*Myrmecophaga tridactyla*), common bottlenose dolphins (*Tursiops truncates*), northern minke whales (*Balaenoptera acutorostrata*), tammar wallabies (*Macropus eugenii*), red kangaroos (*Macropus rufus*), common brushtail possum (*Trichosurus Vulpecula*), koalas (*Phascolarctos cinereus*), eastern quolls (*Dasyurus viverrinus*), platypus (*Ornithorhynchus anatinus*). As used herein, "mammalian milk oligosaccharide" or MMO refers to oligosaccharides such as but not limited to 3-fucosyllactose, 2'-fucosyllactose, 6-fucosyllactose, 2',3-difucosyllactose, 2',2-difucosyllactose, 3,4-difucosyllactose, 6'-sialyllactose, 3'-sialyllactose, 3,6-disialyllactose, 6,6'-disialyllactose, 8,3-disialyllactose, 3,6-disialyllacto-N-tetraose, lactodifucotetraose, lacto-N-tetraose, lacto-N-neotetraose, lacto-N-fucopentaose IL, lacto-N-fucopentaose I, lacto-N-fucopentaose III, lacto-N-fucopentaose V, lacto-N-fucopentaose VI, sialyllacto-N-tetraose c, sialyllacto-N-tetraose b, sialyllacto-N-tetraose a, lacto-N-difucohexaose I, lacto-N-difucohexaose II, lacto-N-hexaose, lacto-N-neohexaose, para-lacto-N-hexaose, monofucosylmonosialyllacto-N-tetraose c, monofucosyl para-lacto-N-hexaose, monofucosyllacto-N-hexaose III, isomeric fucosylated lacto-N-hexaose III, isomeric fucosylated lacto-N-hexaose I, sialyllacto-N-hexaose, sialyllacto-N-neohexaose II, difucosyl-para-lacto-N-hexaose, difucosyllacto-N-hexaose, difucosyllacto-N-hexaose a, difucosyllacto-N-hexaose c, galactosylated chitosan, fucosylated oligosaccharides, neutral oligosaccharide and/or sialylated oligosaccharides. As used herein, "mammalian milk oligosaccharide" refers to oligosaccharides such as but not limited to 3-fucosyllactose, 2'-fucosyllactose, 6-fucosyllactose, 2',3-difucosyllactose, 2',2-difucosyllactose, 3,4-difucosyllactose, 6'-sialyllactose, 3'-sialyllactose, 3,6-disialyllactose, 6,6'-disialyllactose, 8,3-disialyllactose, 3,6-disialyllacto-N-tetraose, lactodifucotetraose, lacto-N-tetraose, lacto-N-neotetraose, lacto-N-fucopentaose II, lacto-N-fucopentaose I, lacto-N-fucopentaose III, lacto-N-fucopentaose V, lacto-N-fucopentaose VI, sialyllacto-N-tetraose c, sialyllacto-N-tetraose b, sialyllacto-N-tetraose a, lacto-N-difucohexaose I, lacto-N-difucohexaose II, lacto-N-hexaose, lacto-N-neohexaose, para-lacto-N-hexaose, monofucosylmonosialyl-lacto-N-tetraose c, monofucosyl para-lacto-N-hexaose, monofucosyllacto-N-hexaose III, isomeric fucosylated lacto-N-hexaose III, isomeric fucosylated lacto-N-hexaose I, sialyllacto-N-hexaose, sialyllacto-N-neohexaose II, difucosyl-para-lacto-N-hexaose, difucosyllacto-N-hexaose, difucosyllacto-N-hexaose a, difucosyllacto-N-hexaose c, galactosylated chitosan, fucosylated oligosaccharides, neutral oligosaccharide and/or sialylated oligosaccharides.

The terms "alpha-2,3-sialyltransferase," "alpha 2,3 sialyltransferase," "3-sialyltransferase," "α-2,3-sialyltransferase," "α 2,3 sialyltransferase," "3 sialyltransferase," "3-ST" or "3ST" or "a23-ST" as used in this disclosure, are used interchangeably and refer to a glycosyltransferase that catalyzes the transfer of sialic acid from the donor CMP-sialic acid, to the acceptor molecule in an alpha-2,3-linkage. The terms "3' sialyllactose," "3'-sialyllactose," "alpha-2,3-sialyllactose," "alpha 2,3 sialyllactose," "α-2,3-sialyllactose," "α 2,3 sialyllactose," "3SL" or "3'SL" as used in this disclosure, are used interchangeably and refer to the product obtained by the catalysis of the alpha-2,3-sialyltransferase transferring the sialic acid group from CMP-Neu5Ac to lactose in an alpha-2,3-linkage.

The terms "3'-KDO-lactose," "3'KDO-lactose," "3' KDO lactose," "3' KDO-lactose" as used in this disclosure, are used interchangeably, and refer to the product obtained by the catalysis of the alpha-2,3-sialyltransferase transferring the sialic acid group from CMP-KDO to lactose in an alpha-2,3-linkage.

The terms "LNT II," "LNT-II," "LN3," "lacto-N-triose IL," "lacto-N-triose IL," "lacto-N-triose," "lacto-N-triose" or "GlcNAcβ1-3Galβ31-4Glc" as used in this disclosure, are used interchangeably. The terms "LNT," "lacto-N-tetraose," "lacto-N-tetraose" or "Galβ1-3GlcNAcβ1-3Galβ1-4Glc" as used in this disclosure, are used interchangeably. The terms "LNnT," "lacto-N-neotetraose," "lacto-N-neotetraose," "neo-LNT" or "Galβ1-4GlcNAcβ1-3Galβ1-4Glc" as used in this disclosure, are used interchangeably.

The terms "LSTa," "LS-Tetrasaccharide a," "Sialyl-lacto-N-tetraose a," "sialyllacto-N-tetraose a" or "Neu5Ac-a2,3-Gal-b1,3-GlcNAc-b1,3-Gal-b1,4-Glc" as used in this disclosure, are used interchangeably. The terms "LSTb," "LS-Tetrasaccharide b," "Sialyl-lacto-N-tetraose b," "sialyllacto-N-tetraose b" or "Gal-b1,3-(Neu5Ac-a2,6)-GlcNAc-b1,3-Gal-b1,4-Glc" as used in this disclosure, are used interchangeably. The terms "LSTc," "LS-Tetrasaccharide c," "Sialyl-lacto-N-tetraose c," "sialyllacto-N-tetraose c," "sialyllacto-N-neotetraose c" or "Neu5Ac-a2,6-Gal-b1,4-GlcNAc-b1,3-Gal-b1,4-Glc" as used in this disclosure, are used interchangeably. The terms "LSTd," "LS-Tetrasaccharide d," "Sialyl-lacto-N-tetraose d," "sialyllacto-N-tetraose d," "sialyllacto-N-neotetraose d" or "Neu5Ac-a2,3-Gal-b1,4-GlcNAc-b1,3-Gal-b1,4-Glc" as used in this disclosure, are used interchangeably. The terms "DSLNnT" and "Disialyl-lacto-N-neotetraose" are used interchangeably and refer to Neu5Ac-a2,6-Gal-b1,4-GlcNAc-b1,3-[Neu5Ac-a2,6]-Gal-b1,4-Glc. The terms "DSLNT," "DS-LNT" and "Disialyl-lacto-N-tetraose" are used interchangeably and refer to Neu5Ac-a2,3-Gal-b1,3-[Neu5Ac-a2,6]-GlcNAc-b1,3-Gal-b1,4-Glc.

The term "membrane transporter proteins" as used herein refers to proteins that are part of or interact with the cell membrane and control the flow of molecules and information across the cell. The membrane proteins are thus involved in transport, be it import into or export out of the cell. Such membrane transporter proteins can be but are not limited to porters, P-P-bond-hydrolysis-driven transporters, β-Barrel Porins, auxiliary transport proteins and phosphotransfer-driven group translocators (Forrest et al., Biochim. Biophys. Acta 1807 (2011) 167-188; Lengeler, J. Mol. Microbiol. Biotechnol. 25 (2015) 79-93; Moraes and Reithmeier, Biochim. Biophys. Acta 1818 (2012), 2687-2706; Saier et al., Nucleic Acids Res. 44 (2016) D372-D379).

The major facilitator superfamily (MFS) is a superfamily of membrane transporter proteins that are single-polypeptide secondary carriers with InterPro domain IPR036259, capable of transporting small solutes in response to chemiosmotic ion gradients (Pao et al., J. Microbiol. Mol. Biol. Rev. 62 (1998) 1-34; Walmsley et al., Trends Biochem. Sci. 23 (1998) 476-481; Wang et al., Jr. Biochim. Biophys. Acta Biomembr. 1862 (2020) 183277; Teelucksingh et al. 202 (2020) e00367-20).

"SET" or "Sugar Efflux Transporter" as used herein is part of the MFS superfamily and refers to membrane proteins of the SET family that are proteins with InterPRO domain IPR004750 and/or are proteins that belong to the egg-NOGv5.0.0 family ENOG410XTE9. This family of proteins is an efflux system for lactose, glucose, aromatic glucosides and galactosides, cellobiose, maltose, a-methyl glucoside and other sugar compounds. They are found in both Gram-negative and Gram-positive bacteria (Liu et al., Mol. Microbiol. 31 (1999) 1845-1851; Liu et al., J. Biol. Chem. 274 (1999) 22977-22984; Sun and Vanderpool, J. Bacteriol. 193 (2011) 143-153).

The term "Siderophore" as used herein is referring to the secondary metabolite of various microorganisms that are mainly ferric ion specific chelators (Neilands, J. Biol. Chem. 270 (1995) 26723-26726). A transporter is needed to export the siderophore outside the cell. Four superfamilies of membrane proteins are identified so far in this process: the major facilitator superfamily (MFS); the Multidrug/Oligosaccharidyl-lipid/Polysaccharide Flippase Superfamily (MOP); the resistance, nodulation and cell division superfamily (RND); and the ABC superfamily (Teelucksingh et al. 202 (2020) e00367-20). In general, the genes involved in siderophore export are clustered together with the siderophore biosynthesis genes. The term "siderophore exporter" as used herein refers to such transporters needed to export the siderophore outside of the cell.

The ATP-binding cassette (ABC) superfamily contains both uptake and efflux transport systems, and the members of these two groups generally cluster loosely together. ATP hydrolysis without protein phosphorylation energizes transport. There are dozens of families within the ABC superfamily, and family generally correlates with substrate specificity (Davidson et al. Microbiol. Mol. Biol. Rev. 72 (2008) 317-364; Goffeau et al. (2013). "ABC Transporters." In Lane W J, Lennarz M D (eds.). Encyclopedia of Biological Chemistry (Second ed.). London: Academic Press. pp. 7-11).

It should be understood for those skilled in the art that for the databases used herein, comprising EggNOG 5.0.0 (released November 2018) and InterPro 86.0 (released 3 Jun. 2021), the content of each database is fixed at each release and is not to be changed. When the content of a specific database is changed, this specific database receives a new release version with a new release date. All release versions for each database with their corresponding release dates and specific content as annotated at these specific release dates are available and known to those skilled in the art.

The term "pathway for production of a sialylated oligosaccharide" as used herein is a biochemical pathway consisting of the enzymes and their respective genes involved in the synthesis of a sialylated oligosaccharide as defined herein. The pathway for production of a sialylated oligosaccharide can comprise but is not limited to pathways involved in the synthesis of a nucleotide-activated sugar and the transfer of the nucleotide-activated sugar to an acceptor to create a sialylated oligosaccharide of this disclosure. An example of such pathway is a sialylation pathway. Further examples of such pathway comprise but are not limited to a fucosylation, galactosylation, N-acetylglucosaminylation, N-acetylgalactosaminylation, mannosylation, N-acetylmannosaminylation pathway.

A 'sialylation pathway' is a biochemical pathway consisting of at least one of the enzymes and their respective genes chosen from the list comprising an L-glutamine-D-fructose-6-phosphate aminotransferase, a phosphoglucosamine mutase, an N-acetylglucosamine-6-P deacetylase, an N-acylglucosamine 2-epimerase, a UDP-N-acetylglucosamine 2-epimerase, an N-acetylmannosamine-6-phosphate 2-epimerase, a UDP-GlcNAc 2-epimerase/kinase, a glucosamine 6-phosphate N-acetyltransferase, an N-acetylglucosamine-6-phosphate phosphatase, a phosphoacetylglucosamine mutase, an N-acetylglucosamine 1-phosphate uridylyltransferase, a glucosamine-1-phosphate acetyltransferase, an Neu5Ac synthase, an N-acetylneuraminate lyase, an N-acylneuraminate-9-phosphate synthase, an N-acylneuraminate-9-phosphatase, a sialic acid transporter and a CMP-sialic acid synthase, combined with a sialyltransferase leading to α 2,3; α 2,6 and/or α 2,8 sialylated oligosaccharides.

The terms "pyruvate dehydrogenase," "pyruvate oxidase," "POX," "poxB" and "pyruvate:ubiquinone-8 oxidoreductase" are used interchangeably and refer to an enzyme that catalyzes the oxidative decarboxylation of pyruvate to produce acetate and CO2.

The terms "lactate dehydrogenase," "D-lactate dehydrogenase," "ldhA," "hslI," "htpH," "D-LDH," "fermentative lactate dehydrogenase" and "D-specific 2-hydroxyacid dehydrogenase" are used interchangeably and refer to an enzyme that catalyzes the conversion of lactate into pyruvate hereby generating NADH.

The term "enabled efflux" means to introduce the activity of transport of a solute over the cytoplasm membrane and/or the cell wall. The transport may be enabled by introducing and/or increasing the expression of a membrane transporter protein as described in this disclosure. The term "enhanced efflux" means to improve the activity of transport of a solute over the cytoplasm membrane and/or the cell wall. Transport of a solute over the cytoplasm membrane and/or cell wall may be enhanced by introducing and/or increasing the expression of a membrane transporter protein as described in this disclosure. "Expression" of a membrane transporter protein is defined as "overexpression" of the gene encoding the membrane transporter protein in the case the gene is an endogenous gene or "expression" in the case the gene encoding the membrane transporter protein is a heterologous gene that is not present in the wild-type strain or cell.

The term "purified" refers to material that is substantially or essentially free from components that interfere with the activity of the biological molecule. For cells, saccharides, nucleic acids, and polypeptides, the term "purified" refers to material that is substantially or essentially free from components that normally accompany the material as found in its native state. Typically, purified saccharides, oligosaccharides, proteins or nucleic acids of the invention are at least about 50%, 55%, 60%, 65%, 70%, 75%, 80% or 85% pure, usually at least about 90%, 91%, 92%, 93%, 94%, 95%, 96%, 97%, 98%, or 99.0% pure as measured by band intensity on a silver-stained gel or other method for determining purity. Purity or homogeneity can be indicated by a number of means well known in the art, such as polyacrylamide gel electrophoresis of a protein or nucleic acid sample, followed by visualization upon staining. For certain purposes high resolution will be needed and HPLC or a similar means for purification utilized. For di- and oligosaccharides, purity can be determined using methods such as but not limited to thin layer chromatography, gas chromatography, NMR, HPLC, capillary electrophoresis or mass spectroscopy. Further herein, the terms "contaminants" and "impurities" preferably mean particulates, cells, cell components, metabolites, cell debris, proteins, peptides, amino acids, nucleic acids, glycolipids and/or endotoxins that can be present in an aqueous medium like e.g., a cultivation or an incubation.

The term "clarifying" as used herein refers to the act of treating an aqueous medium like e.g., a cultivation or an incubation, to remove suspended particulates and contaminants from the production process, like e.g., cells, cell components, insoluble metabolites and debris, that could interfere with the eventual purification of the one or more bioproduct(s). Such treatment can be carried out in a conventional manner by centrifugation, flocculation, flocculation with optional ultrasonic treatment, gravity filtration, microfiltration, foam separation or vacuum filtration (e.g., through a ceramic filter that can include a Celite™ filter aid).

The term "cultivation" refers to the culture medium wherein the cell is cultivated, or fermented, the cell itself, and a sialylated oligosaccharide, preferably a 3'sialylated oligosaccharide that is produced by the cell in whole broth, i.e., inside (intracellularly) as well as outside (extracellularly) of the cell. The terms "culture medium" and "cultivation medium" as used herein are used interchangeably and refer to the medium wherein the cell is cultivated.

The term "incubation" refers to a mixture wherein a sialylated oligosaccharide, preferably a 3'sialylated oligosaccharide, is produced. The mixture can comprise one or more enzyme(s), one or more precursor(s) and one or more acceptor(s) as defined herein present in a buffered solution and incubated for a certain time at a certain temperature enabling production of a sialylated oligosaccharide, preferably a 3'sialylated oligosaccharide, catalyzed by the one or more enzyme(s) using the one or more precursor(s) and the one or more acceptor(s) in the mixture. The mixture can also comprise i) the cell obtained after cultivation or incubation, optionally the cell is subjected to cell lysis, ii) a buffered solution or the cultivation or incubation medium wherein the cell was cultivated or fermented, and iii) a sialylated oligosaccharide, preferably a 3'sialylated oligosaccharide, that is produced by the cell in whole broth, i.e., inside (intracellularly) as well as outside (extracellularly) of the cell. The incubation can also be the cultivation as defined herein.

The terms "reactor" and "incubator" refer to the recipient filled with the cultivation or incubation. Examples of reactors and incubators comprise but are not limited to microfluidic devices, well plates, tubes, shake flasks, fermenters, bioreactors, process vessels, cell culture incubators, CO2 incubators.

As used herein, the term "cell productivity index (CPI)" refers to the mass of the sialylated oligosaccharide produced by the cells divided by the mass of the cells produced in the culture.

The term "precursor" as used herein refers to substances that are taken up or synthetized by the cell for the specific production of a sialylated oligosaccharide according to this disclosure. In this sense a precursor can be an acceptor as defined herein, but can also be another substance, metabolite, which is first modified within the cell as part of the biochemical synthesis route of a sialylated oligosaccharide. The term "precursor" as used herein is also to be understood as a chemical compound that participates in a chemical or enzymatic reaction to produce another compound like e.g., an intermediate or an acceptor as defined herein, as part in the metabolic pathway of a sialylated oligosaccharide, preferably a 3'sialylated oligosaccharide. The term "precursor" as used herein is also to be understood as a donor that is used by a glycosyltransferase to modify an acceptor as defined herein with a sugar moiety in a glycosidic bond, as part in the metabolic pathway of a sialylated oligosaccharide, preferably a 3'sialylated oligosaccharide. Examples of such precursors comprise the acceptors as defined herein, and/or dihydroxyacetone, glucosamine, N-acetylglucosamine, N-acetylmannosamine, galactosamine, N-acetylgalactosamine, galactosyllactose, phosphorylated sugars or sugar phosphates like e.g., but not limited to glucose-1-phosphate, galactose-1-phosphate, glucose-6-phosphate, fructose-6-phosphate, fructose-1,6-bisphosphate, mannose-6-phosphate, mannose-1-phosphate, glycerol-3-phosphate, glyceraldehyde-3-phosphate, dihydroxyacetone-phosphate, glucosamine-6-phosphate, N-acetylglucosamine-6-phosphate, N-acetylmannosamine-6-phosphate, N-acetylglucosamine-1-phosphate, N-acetylneuraminic acid-9-phosphate and nucleotide-activated sugars like nucleotide diphospho-sugars and nucleotide monophospho-sugars as defined herein like e.g., UDP-glucose, UDP-galactose, UDP-N-acetylglucosamine, CMP-sialic acid, GDP-mannose, GDP-4-dehydro-6-deoxy-α-D-mannose, GDP-fucose.

Optionally, the cell is transformed to comprise and to express at least one nucleic acid sequence encoding a protein selected from the group consisting of lactose transporter, N-acetylneuraminic acid transporter, fucose transporter, glucose transporter, galactose transporter, transporter for a nucleotide-activated sugar wherein the transporter internalizes to the medium added precursor for the synthesis of the sialylated oligosaccharide, preferably 3'sialylated oligosaccharide.

The term "acceptor" as used herein refers to a mono-, di- or oligosaccharide, which can be modified by a glycosyltransferase. Examples of such acceptors comprise glucose, galactose, fructose, glycerol, sialic acid, fucose, mannose, maltose, sucrose, lactose, lacto-N-triose, lacto-N-tetraose (LNT), lacto-N-neotetraose (LNnT), lacto-N-pentaose (LNP), lacto-N-neopentaose, para lacto-N-pentaose, para lacto-N-neopentaose, lacto-N-novopentaose I, lacto-N-hexaose (LNH), lacto-N-neohexaose (LNnH), para lacto-N-neohexaose (pLNnH), para lacto-N-hexaose (pLNH), lacto-N-heptaose, lacto-N-neoheptaose, para lacto-N-neoheptaose, para lacto-N-heptaose, lacto-N-octaose (LNO), lacto-N-neooctaose, iso lacto-N-octaose, para lacto-N-octaose, iso lacto-N-neooctaose, novo lacto-N-neooctaose, para lacto-N-neooctaose, iso lacto-N-nonaose, novo lacto-N-nonaose, lacto-N-nonaose, lacto-N-decaose, iso lacto-N-decaose, novo lacto-N-decaose, lacto-N-neodecaose, and oligosaccharide containing 1 or more N-acetyllactosamine units and/or 1 or more lacto-N-biose units or an intermediate into oligosaccharide, fucosylated and sialylated versions thereof, ceramide, N-acylated sphingoid, glucosylceramide, lactosylceramide, sphingosine, phytosphingosine, sphingosine synthons, peptide backbones with beta-GlcNAc-Asn residues, glycoproteins with terminal GlcNAc and Gal residues, immunoglobulins.

In a first aspect, this disclosure provides a method for the production of a sialylated oligosaccharide, preferably a 3'sialylated oligosaccharide, more preferably 3'SL (Neu5Ac-a2,3-Gal-b1,4-Glc). The method comprising contacting a sialyltransferase with a mixture comprising a donor comprising a sialic acid residue, and an acceptor chosen from the list comprising an oligosaccharide or disaccharide, under conditions wherein the sialyltransferase catalyzes the transfer of a sialic acid residue from the donor to the acceptor, thereby producing the sialylated oligosaccharide. Herein, the sialyltransferase has alpha-2,3-sialyltransferase activity on the galactose (Gal) residue of lactose and comprises an amino acid sequence that is i) at least 67.0% identical over a stretch of at least 150 amino acid residues, preferably at least 200 amino acid residues, to any one of the amino acid sequences as represented by SEQ ID NOs:5, 1, 2, 3, 6, 7 or 8 or ii) at least 85.0% identical over a stretch of at least 150 amino acid residues, preferably at least 200 amino acid residues, to the amino acid sequence as represented by SEQ ID NO:4 or iii) at least 60.0% identical over a stretch of at least 150 amino acid residues, preferably at least 200 amino acid residues, to the amino acid sequence as represented by SEQ ID NO:12. Preferably, the sialylated oligosaccharide is a 3'sialylated oligosaccharide, more preferably 3'SL and the acceptor substrate is lactose. In a preferred embodiment, the sialyltransferase has also alpha-2,3-sialyltransferase activity on the galactose (Gal) residue of acceptors other than lactose, e.g., lacto-N-tetraose or lacto-N-neotetraose.

In a preferred aspect, this disclosure provides a method for the production of a 3'sialylated oligosaccharide. The method comprising contacting a sialyltransferase with a mixture comprising a donor comprising a sialic acid residue, and an acceptor chosen from the list comprising an oligosaccharide or disaccharide, under conditions wherein the sialyltransferase catalyzes the transfer of a sialic acid residue from the donor to the acceptor, thereby producing the 3'sialylated oligosaccharide. Herein, the sialyltransferase has alpha-2,3-sialyltransferase activity on the galactose (Gal) residue of lactose and comprises an amino acid sequence that is at least 80.0% identical to any one of the full-length amino acid sequences as represented by SEQ ID NOs:5, 4, 12, 1, 2, 3, 6, 7, or 8. Preferably, the 3'sialylated oligosaccharide is separated. In a preferred embodiment, the sialyltransferase has also alpha-2,3-sialyltransferase activity on the galactose (Gal) residue of acceptors other than lactose, e.g., lacto-N-tetraose or lacto-N-neotetraose.

In a specific embodiment, this disclosure provides a method for the production of a sialylated oligosaccharide, preferably a 3'sialylated oligosaccharide, more preferably 3'SL (Neu5Ac-a2,3-Gal-b1,4-Glc) wherein the method comprises the steps of:
a) providing
  i. CMP-sialic acid
  ii. an acceptor, preferably lactose
  iii. a sialyltransferase, wherein the sialyltransferase is a sialyltransferase that has alpha-2,3-sialyltransferase activity on the galactose (Gal) residue of lactose and comprises an amino acid sequence that is i) at least 67.0% identical over a stretch of at least 150 amino acid residues, preferably at least 200 amino acid residues, to any one of the amino acid sequences as represented by SEQ ID NOs:5, 1, 2, 3, 6, 7 or 8 or ii) at least 85.0% identical over a stretch of at least 150 amino acid residues, preferably at least 200 amino acid residues, to the amino acid sequence as represented by SEQ ID NO:04 or iii) at least 60.0% identical over a stretch of at least 150 amino acid residues, preferably at least 200 amino acid residues, to the amino acid sequence as represented by SEQ ID NO:12,
b) contacting the sialyltransferase and CMP-sialic acid with the acceptor, preferably lactose, under conditions where the sialyltransferase catalyzes the transfer of a sialic acid residue from the CMP-sialic acid to the acceptor resulting in the production of a sialylated oligosaccharide, preferably a 3'sialylated oligosaccharide, more preferably 3'SL (Neu5Ac-a2,3-Gal-b1,4-Glc),
c) preferably, separating the produced sialylated oligosaccharide.

Preferably, the sialyltransferase is any one of the sialyltransferase as described herein.

In a specific embodiment, this disclosure provides a method for the production of a 3'sialylated oligosaccharide, wherein the method comprises the steps of:
a) providing
  i. CMP-sialic acid
  ii. an acceptor, preferably lactose
  iii. a sialyltransferase, wherein the sialyltransferase is a sialyltransferase that has alpha-2,3-sialyltransferase activity on the galactose (Gal) residue of lactose and comprises an amino acid sequence that is at least 80.0% identical to any one of the full-length amino acid sequences as represented by SEQ ID NOs:5, 4, 12, 1, 2, 3, 6, 7, or 8, b) contacting the sialyltransferase and CMP-sialic acid with the acceptor, preferably lactose, under conditions where the sialyltransferase catalyzes the transfer of a sialic acid residue from the CMP-sialic acid to the acceptor resulting in the production of a 3'sialylated oligosaccharide, c) preferably, separating the produced 3'sialylated oligosaccharide.

Preferably, the sialyltransferase is any one of the sialyltransferase as described herein.

In an alternative specific embodiment, this disclosure provides a method wherein a cell extract comprising a sialyltransferase as described herein is contacted with a mixture comprising a donor comprising a sialic acid residue, and an acceptor comprising an oligosaccharide or disaccharide, under conditions wherein the sialyltransferase catalyzes the transfer of a sialic acid residue from the donor to the acceptor, thereby producing the sialylated oligosaccharide. Preferably the sialylated oligosaccharide is a 3'sialylated oligosaccharide, more preferably 3'SL.

In an alternative embodiment of the method of this disclosure, the sialylated oligosaccharide is produced in a cell-free system. Preferably the sialylated oligosaccharide is α 3'sialylated oligosaccharide, more preferably 3'SL.

In another aspect, this disclosure provides a method for the production of a sialylated oligosaccharide, preferably a 3'sialylated oligosaccharide, more preferably 3'SL (Neu5Ac-a2,3-Gal-b1,4-Glc), wherein the method comprises the steps of:

i. providing a cell, preferably a single cell, expressing, preferably heterologously expressing, more preferably overexpressing, even more preferably heterologously overexpressing, a sialyltransferase wherein the sialyltransferase has alpha-2,3-sialyltransferase activity on the galactose (Gal) residue of lactose and comprises an amino acid sequence that is i) at least 67.0% identical over a stretch of at least 150 amino acid residues, preferably at least 200 amino acid residues, to any one of the amino acid sequences as represented by SEQ ID NOs:05, 01, 02, 03, 06, 07 or 08, or ii) at least 85.0% identical over a stretch of at least 150 amino acid residues, preferably at least 200 amino acid residues, to the amino acid sequence as represented by SEQ ID NO:04, or iii) at least 60.0% identical over a stretch of at least 150 amino acid residues, preferably at least 200 amino acid residues, to the amino acid sequence as represented by SEQ ID NO:12, ii. providing CMP-sialic acid, optionally the CMP-sialic acid is produced by the cell, and iii. providing an oligosaccharide or disaccharide, optionally the oligosaccharide or disaccharide is produced by the cell, and iv. cultivating and/or incubating the cell under conditions permissive to express the sialyltransferase, optionally permissive to produce the CMP-sialic acid and/or the oligosaccharide or disaccharide, preferably, separating the sialylated oligosaccharide, preferably 3'sialylated oligosaccharide, more preferably 3'SL, from the cultivation or incubation.

In another aspect, this disclosure provides a method for the production of a 3'sialylated oligosaccharide, wherein the method comprises the steps of:

i. providing a cell, preferably a single cell, expressing, preferably heterologously expressing, more preferably overexpressing, a sialyltransferase wherein the sialyltransferase has alpha-2,3-sialyltransferase activity on the galactose (Gal) residue of lactose and comprises an amino acid sequence that is at least 80.0% identical to any one of the full-length amino acid sequences as represented by SEQ ID NOs:5, 4, 12, 1, 2, 3, 6, 7 or 8, ii. providing CMP-sialic acid, optionally the CMP-sialic acid is produced by the cell, and iii. providing an oligosaccharide or disaccharide, optionally the oligosaccharide or disaccharide is produced by the cell, and iv. cultivating and/or incubating the cell under conditions a) permissive to express the sialyltransferase, optionally permissive to produce the CMP-sialic acid and/or the oligosaccharide or disaccharide, and b) wherein the sialyltransferase catalyzes the transfer of a sialic residue from the CMP-sialic acid to the acceptor resulting in the production of the 3'sialylated oligosaccharide, preferably, separating the 3'sialylated oligosaccharide from the cultivation or incubation.

In a specific embodiment of the method of this disclosure, the sialylated oligosaccharide is produced by a cell, preferably a single cell, wherein the cell expresses i) a sialyltransferase that has alpha-2,3-sialyltransferase activity on the Gal residue of lactose and comprises an amino acid sequence that is i) at least 67.0% identical over a stretch of at least 150 amino acid residues, preferably at least 200 amino acid residues, to any one of the amino acid sequences as represented by SEQ ID NOs:5, 1, 2, 3, 6, 7 or 8, ii) at least 85.0% identical over a stretch of at least 150 amino acid residues, preferably at least 200 amino acid residues, to the amino acid sequence as represented by SEQ ID NO:04, iii) at least 60.0% identical over a stretch of at least 150 amino acid residues, preferably at least 200 amino acid residues, to the amino acid sequence as represented by SEQ ID NO:12, or iv) any of the sialyltransferases as described herein.

In a preferred embodiment of the method of this disclosure, the 3'sialylated oligosaccharide is produced by a cell, preferably a single cell, wherein the cell expresses i) a sialyltransferase that has alpha-2,3-sialyltransferase activity on the Gal residue of lactose and comprises an amino acid sequence that is at least 80.0% identical to any one of the full-length amino acid sequences as represented by SEQ ID NOs:5, 4, 12, 1, 2, 3, 6, 7 or 8, or ii) any of the sialyltransferases as described herein.

The cell used can be a metabolically engineered cell as described herein, preferably wherein the cell is metabolically engineered for the production of the sialylated oligosaccharide. Preferably the sialylated oligosaccharide is a 3'sialylated oligosaccharide, more preferably 3'SL. Preferably, the cell is metabolically engineered for the production of a 3'sialylated oligosaccharide.

In a preferred embodiment of the method and/or cell, the sialyltransferase as described herein comprises an amino acid sequence that is at least 67.0%, at least 70.0%, at least 75.0%, at least 80.0%, at least 85.0%, at least 90.0%, at least 95.0%, at least 96.0%, at least 97.0%, at least 98.0%, at least 98.5%, or at least 99.0% identical to any one of the amino acid sequences as represented by SEQ ID NOs:05, 01, 02, 03, 06, 07 or 08 over a stretch of at least 150, at least 160, at least 170, at least 180, at least 190, at least 200, at least 210, at least 220, at least 230, at least 240, at least 250, at least 260, at least 270, at least 280, at least 290 or at least 300 amino acid residues.

In a more preferred embodiment, the sialyltransferase comprises an amino acid sequence that is at least 55.0%, at least 60.0%, at least 65.0%, at least 70.0%, at least 75.0%, at least 80.0%, at least 85.0%, at least 90.0%, at least 95.0%, at least 96.0%, at least 97.0%, at least 98.0%, at least 98.5%, or at least 99.0% identical to any one of the full-length amino acid sequences as represented by SEQ ID NOs:5, 1, 2, 3, 6, 7, or 8.

In another preferred embodiment of the method and/or cell hereof, the sialyltransferase as described herein comprises an amino acid sequence that is at least 85.0%, at least 90.0%, at least 95.0%, at least 96.0%, at least 97.0%, at least 98.0%, at least 98.5%, or at least 99.0% identical to the amino acid sequence as represented by SEQ ID NO:04 over a stretch of at least 150, at least 160, at least 170, at least 180, at least 190, at least 200, at least 210, at least 220, at least 230, at least 240, at least 250, at least 260, at least 270, at least 280, at least 290 or at least 300 amino acid residues.

In another more preferred embodiment, the sialyltransferase comprises an amino acid sequence that is at least 80.0%, at least 85.0%, at least 90.0%, at least 95.0%, at least 96.0%, at least 97.0%, at least 98.0%, at least 98.5%, or at least 99.0% identical to the full-length amino acid sequence as represented by SEQ ID NO:4.

In another preferred embodiment of the method and/or cell hereof, the sialyltransferase as described herein comprises an amino acid sequence that is at least 60.0%, at least 65.0%, at least 70.0%, at least 75.0%, at least 80.0%, at least 85.0%, at least 90.0%, at least 95.0%, at least 96.0%, at least 97.0%, at least 98.0%, at least 98.5%, or at least 99.0% identical to the amino acid sequence as represented by SEQ ID NO:12 over a stretch of at least 150, at least 160, at least 170, at least 180, at least 190, at least 200, at least 210, at least 220, at least 230, at least 240, at least 250, at least 260, at least 270, at least 280, at least 290 or at least 300 amino acid residues.

In another more preferred embodiment, the sialyltransferase comprises an amino acid sequence that is at least 45.0%, at least 50.0%, at least 55.0%, at least 60.0%, at least 65.0%, at least 70.0%, at least 75.0%, at least 80.0%, at least 85.0%, at least 90.0%, at least 95.0%, at least 96.0%, at least 97.0%, at least 98.0%, at least 98.5%, or at least 99.0% identical to the full-length amino acid sequence as represented by SEQ ID NO:12.

Alternatively, the sialyltransferase as described herein comprises an amino acid sequence comprising a fragment of any one of the amino acid sequences as represented by SEQ ID NOs:5, 4, 12, 1, 2, 3, 6, 7, or 8 and having alpha-2,3-sialyltransferase activity on the Gal residue of lactose.

Most preferably, the sialyltransferase comprises an amino acid sequence as represented by any one of the SEQ ID NOs:5, 4, 12, 1, 2, 3, 6, 7, or 8.

In the scope of this disclosure, permissive conditions are understood to be conditions relating to physical or chemical parameters including but not limited to temperature, pH, pressure, osmotic pressure and product/donor/precursor/acceptor concentration.

In a particular embodiment, the permissive conditions may include a temperature-range of about 30+/−20 degrees centigrade, a pH-range of 2.0-10.0, preferably a pH range of 3.0-7.0.

In another and/or additional preferred embodiment of the method and/or cell hereof, the sialic acid residue is at least one chosen from the list consisting of Neu4Ac; Neu5Ac; Neu4,5Ac2; Neu5,7Ac2; Neu5,8Ac2; Neu5,9Ac2; Neu4,5,9Ac3; Neu5,7,9Ac3; Neu5,8,9Ac3; Neu4,5,7,9Ac4; Neu5,7,8,9Ac4; Neu4,5,7,8,9Ac5; Neu5Gc and 2-keto-3-deoxy-manno-octulonic acid (KDO). In a more preferred embodiment, the sialic acid residue is Neu5Ac. In another more preferred embodiment, the sialic acid residue is KDO.

In another and/or additional preferred embodiment of the method and/or cell hereof, the donor comprising a sialic acid residue is CMP-sialic acid. In a more preferred embodiment, the donor comprising a sialic acid residue is chosen from the list consisting of CMP-Neu5Ac, CMP-Neu4Ac, CMP-Neu5Ac9N$_3$, CMP-Neu4,5Ac$_2$, CMP-Neu5,7Ac$_2$, CMP-Neu5,9Ac$_2$, CMP-Neu5,7(8,9)Ac$_2$, CMP-N-glycolylneuraminic acid (CMP-Neu5Gc) and CMP-KDO. In an even more preferred embodiment, the donor comprising a sialic acid residue is CMP-Neu5Ac. In another even more preferred embodiment, the donor comprising a sialic acid residue is CMP-KDO.

Preferably, the sialylated oligosaccharide is a 3'sialylated oligosaccharide, more preferably 3'SL and the acceptor is lactose. Alternatively, the sialylated oligosaccharide is α 3'sialylated oligosaccharide and the 3' sialylated oligosaccharide is a saccharide modified with KDO, more preferably 3'KDO-lactose and the acceptor is lactose. Alternatively, the sialylated oligosaccharide is a 3'sialylated oligosaccharide and the 3'sialylated oligosaccharide is a mixture of 3'sialyl-lactose and 3'KDO-lactose, and the acceptor is lactose.

In an embodiment of the method hereof, the cultivation medium contains at least one carbon source selected from the group consisting of glucose, fructose, sucrose, and glycerol.

In another embodiment of the method hereof, the cultivation or incubation medium contains at least one compound selected from the group consisting of lactose, galactose, glucose, sialic acid, CMP-sialic acid, CMP-Neu5Ac and CMP-KDO.

Preferably, the sialylated oligosaccharide is recovered from the cultivation or incubation medium and/or the cell or separated from the cultivation or incubation as explained herein. More preferably, the sialylated oligosaccharide is a 3'sialylated oligosaccharide and the 3'sialylated oligosaccharide is recovered from the cultivation or incubation medium and/or the cell or separated from the cultivation or incubation as explained herein.

According to an embodiment of the method of this disclosure, the conditions permissive to produce the sialylated oligosaccharide comprise the use of a cultivation or incubation medium comprising at least one precursor and/or acceptor for the production of a sialylated oligosaccharide, preferably a 3'sialylated oligosaccharide, as described herein. Preferably, the cultivation or incubation medium contains at least one precursor and/or acceptor, wherein the precursor is selected from the group comprising a monosaccharide like e.g., galactose, glucose, fucose, sialic acid, GlcNAc, GalNAc; a nucleotide-activated sugar like e.g., CMP-sialic acid, CMP-Neu5Ac, CMP-KDO, UDP-Gal, UDP-GlcNAc, GDP-fucose; a disaccharide like e.g., lactose; and an oligosaccharide like e.g., lacto-N-triose (LN3), lacto-N-tetraose (LNT) and lacto-N-neotetraose (LNnT) and/or wherein the acceptor is selected from the group comprising a disaccharide like e.g., lactose, and an oligosaccharide like e.g., LN3, LNT, LNnT. In a more preferred embodiment of the method of this disclosure, the precursor is chosen from the list comprising sialic acid, CMP-sialic acid, CMP-KDO, glucose, galactose and UDP-galactose. In another more preferred embodiment of the method of this disclosure, the acceptor is lactose.

According to an alternative and/or additional embodiment of the method of this disclosure, the conditions permissive to produce the sialylated oligosaccharide, preferably 3'sialylated oligosaccharide, comprise adding to the cultivation or incubation medium at least one precursor and/or acceptor feed for the production of the sialylated oligosaccharide, preferably 3'sialylated oligosaccharide.

According to an alternative embodiment of the method of this disclosure, the conditions permissive to produce the sialylated oligosaccharide, preferably 3'sialylated oligosaccharide, comprise the use of a cultivation or incubation medium wherein the cultivation or incubation medium lacks any precursor and/or acceptor for the production of the sialylated oligosaccharide, preferably 3'sialylated oligosaccharide, and is combined with a further addition to the cultivation or incubation medium of at least one precursor and/or acceptor feed for the production of the sialylated oligosaccharide, preferably 3'sialylated oligosaccharide.

According to an embodiment of the method of this disclosure, the cultivation or incubation is contained in a reactor or incubator, as defined herein. The volume of the reactor or incubator ranges from microliter (µL) scale to 10,000 m3 (cubic meter). In a preferred embodiment, the volume of the reactor or incubator ranges from 250 mL (milliliter) to 10,000 m3 (cubic meter).

In a preferred embodiment, the method for the production of a sialylated oligosaccharide, preferably 3'sialylated oligosaccharide, as described herein comprises at least one of the following steps:
  i) Use of a cultivation or incubation medium comprising at least one precursor and/or acceptor;
  ii) Adding to the cultivation or incubation medium in a reactor or incubator at least one precursor and/or acceptor feed wherein the total reactor or incubator volume ranges from 250 mL (milliliter) to 10,000 $m^3$ (cubic meter), preferably in a continuous manner, and preferably so that the final volume of the cultivation or incubation medium is not more than three-fold, preferably not more than two-fold, more preferably less than two-fold of the volume of the cultivation or incubation medium before the addition of the precursor and/or acceptor feed;
  iii) Adding to the cultivation or incubation medium in a reactor or incubator at least one precursor and/or acceptor feed wherein the total reactor or incubator volume ranges from 250 mL (milliliter) to 10,000 $m^3$ (cubic meter), preferably in a continuous manner, and preferably so that the final volume of the cultivation or incubation medium is not more than three-fold, preferably not more than two-fold, more preferably less than two-fold of the volume of the cultivation or incubation medium before the addition of the precursor and/or acceptor feed and wherein preferably, the pH of the precursor and/or acceptor feed is set between 2.0 and 10.0 and wherein preferably, the temperature of the precursor and/or acceptor feed is kept between 20° C. and 80° C.;
  iv) Adding at least one precursor and/or acceptor feed in a continuous manner to the cultivation or incubation medium over the course of 1 day, 2 days, 3 days, 4 days, 5 days by means of a precursor and/or acceptor feeding solution;
  v) Adding at least one precursor and/or acceptor feed in a continuous manner to the cultivation or incubation medium over the course of 1 day, 2 days, 3 days, 4 days, 5 days by means of a precursor and/or acceptor feeding solution and wherein preferably, the pH of the precursor and/or acceptor feeding solution is set between 2.0 and 10.0 and wherein preferably, the temperature of the precursor and/or acceptor feeding solution is kept between 20° C. and 80° C.;

the method resulting in a sialylated oligosaccharide, preferably a 3'sialylated oligosaccharide, more preferably 3'SL and/or 3'KDO-lactose, with a concentration of at least 50 g/L, preferably at least 75 g/L, more preferably at least 90 g/L, more preferably at least 100 g/L, more preferably at least 125 g/L, more preferably at least 150 g/L, more preferably at least 175 g/L, more preferably at least 200 g/L in the final volume of the cultivation or incubation. In a more preferred embodiment of the method of this disclosure, the precursor is chosen from the list comprising sialic acid, CMP-sialic acid, CMP-Neu5Ac, CMP-KDO, glucose, galactose and UDP-galactose. In another more preferred embodiment of the method of this disclosure, the acceptor is lactose.

In another and/or additional preferred embodiment, the method for the production of a sialylated oligosaccharide, preferably 3'sialylated oligosaccharide, as described herein comprises at least one of the following steps:
  i) Use of a cultivation or incubation medium comprising at least one precursor and/or acceptor;
  ii) Adding to the cultivation or incubation medium in a reactor or incubator at least one precursor and/or acceptor in one pulse or in a discontinuous (pulsed) manner wherein the total reactor or incubator volume ranges from 250 mL (milliliter) to 10,000 $m^3$ (cubic meter), preferably so that the final volume of the cultivation or incubation medium is not more than three-fold, preferably not more than two-fold, more preferably less than two-fold of the volume of the cultivation or incubation medium before the addition of the precursor and/or acceptor feed pulse(s);
  iii) Adding to the cultivation or incubation medium in a reactor or incubator at least one precursor and/or acceptor feed in one pulse or in a discontinuous (pulsed) manner wherein the total reactor or incubator volume ranges from 250 mL (milliliter) to 10,000 $m^3$ (cubic meter), preferably so that the final volume of the cultivation or incubation medium is not more than three-fold, preferably not more than two-fold, more preferably less than two-fold of the volume of the cultivation or incubation medium before the addition of the precursor and/or acceptor feed and wherein preferably, the pH of the precursor and/or acceptor feed pulse(s) is set between 2.0 and 10.0 and wherein preferably, the temperature of the precursor and/or acceptor feed pulse(s) is kept between 20° C. and 80° C.;
  iv) Adding at least one precursor and/or acceptor feed in a discontinuous (pulsed) manner to the cultivation or incubation medium over the course of 5 minutes, 10 minutes, 30 minutes, 1 hour, 2 hours, 4 hours, 10 hours, 12 hours, 1 day, 2 days, 3 days, 4 days, 5 days by means of a precursor and/or acceptor feeding solution;
  v) Adding at least one precursor and/or acceptor feed in a discontinuous (pulsed) manner to the cultivation or incubation medium over the course of 5 minutes, 10 minutes, 30 minutes, 1 hour, 2 hours, 4 hours, 10 hours, 12 hours, 1 day, 2 days, 3 days, 4 days, 5 days by means of a precursor and/or acceptor feeding solution and wherein preferably, the pH of the precursor and/or acceptor feeding solution is set between 2.0 and 10.0 and wherein preferably, the temperature of the precursor and/or acceptor feeding solution is kept between 20° C. and 80° C.;

the method resulting in a sialylated oligosaccharide, preferably a 3'sialylated oligosaccharide, more preferably 3'SL and/or 3'KDO-lactose, with a concentration of at least 50 g/L, preferably at least 75 g/L, more preferably at least 90 g/L, more preferably at least 100 g/L, more preferably at least 125 g/L, more preferably at least 150 g/L, more preferably at least 175 g/L, more preferably at least 200 g/L in the final volume of the cultivation or incubation. In a more preferred embodiment of the method of this disclosure, the precursor is chosen from the list comprising sialic acid, CMP-sialic acid, CMP-Neu5Ac, CMP-KDO, glucose, galactose and UDP-galactose. In another more preferred embodiment of the method of this disclosure, the acceptor is lactose.

In another and/or additional preferred embodiment, the method for the production of a sialylated oligosaccharide, preferably 3'sialylated oligosaccharide, as described herein comprises at least one of the following steps:

i) Use of a cultivation or incubation medium comprising at least 50, more preferably at least 75, more preferably at least 100, more preferably at least 120, more preferably at least 150 grams of precursor per liter of initial reactor or incubator volume wherein the reactor or incubator volume ranges from 250 mL to 10,000 m$^3$ (cubic meter);

ii) Adding to the cultivation or incubation medium in a reactor or incubator at least one precursor feed comprising at least 50, more preferably at least 75, more preferably at least 100, more preferably at least 120, more preferably at least 150 grams of precursor per liter of initial reactor or incubator volume wherein the total reactor or incubator volume ranges from 250 mL (milliliter) to 10,000 m$^3$ (cubic meter), preferably in a continuous manner, and preferably so that the final volume of the cultivation or incubation medium is not more than three-fold, preferably not more than two-fold, more preferably less than two-fold of the volume of the cultivation or incubation medium before the addition of the precursor feed;

iii) Adding to the cultivation or incubation medium in a reactor or incubator at least one precursor feed comprising at least 50, more preferably at least 75, more preferably at least 100, more preferably at least 120, more preferably at least 150 grams of precursor per liter of initial reactor or incubator volume wherein the total reactor or incubator volume ranges from 250 mL (milliliter) to 10,000 m$^3$ (cubic meter), preferably in a continuous manner, and preferably so that the final volume of the cultivation or incubation medium is not more than three-fold, preferably not more than two-fold, more preferably less than two-fold of the volume of the cultivation or incubation medium before the addition of the precursor feed and wherein preferably, the pH of the precursor feed is set between 2.0 and 10.0 and wherein preferably, the temperature of the precursor feed is kept between 20° C. and 80° C.;

iv) Adding at least one precursor feed in a continuous manner to the cultivation or incubation medium over the course of 1 day, 2 days, 3 days, 4 days, 5 days by means of a precursor feeding solution;

v) Adding at least one precursor feed in a continuous manner to the cultivation or incubation medium over the course of 1 day, 2 days, 3 days, 4 days, 5 days by means of a precursor feeding solution and wherein the concentration of the precursor feeding solution is 50 g/L, preferably 75 g/L, more preferably 100 g/L, more preferably 125 g/L, more preferably 150 g/L, more preferably 175 g/L, more preferably 200 g/L, more preferably 225 g/L, more preferably 250 g/L, more preferably 275 g/L, more preferably 300 g/L, more preferably 325 g/L, more preferably 350 g/L, more preferably 375 g/L, more preferably, 400 g/L, more preferably 450 g/L, more preferably 500 g/L, even more preferably, 550 g/L, most preferably 600 g/L; and wherein preferably, the pH of the precursor feeding solution is set between 2.0 and 10.0 and wherein preferably, the temperature of the precursor feeding solution is kept between 20° C. and 80° C.;

the method resulting in a sialylated oligosaccharide, preferably a 3'sialylated oligosaccharide, more preferably 3'SL and/or 3'KDO-lactose, with a concentration of at least 50 g/L, preferably at least 75 g/L, more preferably at least 90 g/L, more preferably at least 100 g/L, more preferably at least 125 g/L, more preferably at least 150 g/L, more preferably at least 175 g/L, more preferably at least 200 g/L in the final volume of the cultivation or incubation. In a more preferred embodiment of the method of this disclosure, the precursor is chosen from the list comprising sialic acid, CMP-sialic acid, CMP-Neu5Ac, CMP-KDO, glucose, galactose and UDP-galactose.

In another and/or additional preferred embodiment, the method for the production of a sialylated oligosaccharide, preferably 3'sialylated oligosaccharide, as described herein comprises at least one of the following steps:

i) Use of a cultivation or incubation medium comprising at least 50, more preferably at least 75, more preferably at least 100, more preferably at least 120, more preferably at least 150 grams of acceptor per liter of initial reactor or incubator volume wherein the reactor or incubator volume ranges from 250 mL to 10,000 m$^3$ (cubic meter);

ii) Adding to the cultivation or incubation medium in a reactor or incubator at least one acceptor feed comprising at least 50, more preferably at least 75, more preferably at least 100, more preferably at least 120, more preferably at least 150 grams of acceptor per liter of initial reactor or incubator volume wherein the total reactor or incubator volume ranges from 250 mL (milliliter) to 10,000 m$^3$ (cubic meter), preferably in a continuous manner, and preferably so that the final volume of the cultivation or incubation medium is not more than three-fold, preferably not more than two-fold, more preferably less than two-fold of the volume of the cultivation or incubation medium before the addition of the acceptor feed;

iii) Adding to the cultivation or incubation medium in a reactor or incubator at least one acceptor feed comprising at least 50, more preferably at least 75, more preferably at least 100, more preferably at least 120, more preferably at least 150 grams of acceptor per liter of initial reactor or incubator volume wherein the total reactor or incubator volume ranges from 250 mL (milliliter) to 10,000 m$^3$ (cubic meter), preferably in a continuous manner, and preferably so that the final volume of the cultivation or incubation medium is not more than three-fold, preferably not more than two-fold, more preferably less than two-fold of the volume of the cultivation or incubation medium before the addition of the acceptor feed and wherein preferably, the pH of the acceptor feed is set between 2.0 and 10.0 and wherein preferably, the temperature of the acceptor feed is kept between 20° C. and 80° C.;

iv) Adding at least one acceptor feed in a continuous manner to the cultivation or incubation medium over the course of 1 day, 2 days, 3 days, 4 days, 5 days by means of an acceptor feeding solution;
v) Adding at least one acceptor feed in a continuous manner to the cultivation or incubation medium over the course of 1 day, 2 days, 3 days, 4 days, 5 days by means of an acceptor feeding solution and wherein the concentration of the acceptor feeding solution is 50 g/L, preferably 75 g/L, more preferably 100 g/L, more preferably 125 g/L, more preferably 150 g/L, more preferably 175 g/L, more preferably 200 g/L, more preferably 225 g/L, more preferably 250 g/L, more preferably 275 g/L, more preferably 300 g/L, more preferably 325 g/L, more preferably 350 g/L, more preferably 375 g/L, more preferably, 400 g/L, more preferably 450 g/L, more preferably 500 g/L, even more preferably, 550 g/L, most preferably 600 g/L; and wherein preferably, the pH of the acceptor feeding solution is set between 2.0 and 10.0 and wherein preferably, the temperature of the acceptor feeding solution is kept between 20° C. and 80° C.;

The method resulting in a sialylated oligosaccharide, preferably a 3'sialylated oligosaccharide, more preferably 3'SL and/or 3'KDO-lactose, with a concentration of at least 50 g/L, preferably at least 75 g/L, more preferably at least 90 g/L, more preferably at least 100 g/L, more preferably at least 125 g/L, more preferably at least 150 g/L, more preferably at least 175 g/L, more preferably at least 200 g/L in the final volume of the cultivation or incubation. In a more preferred embodiment of the method of this disclosure, the acceptor is lactose.

In another and/or additional preferred embodiment, the method for the production of a sialylated oligosaccharide, preferably 3'sialylated oligosaccharide, as described herein comprises at least one of the following steps:
i) Use of a cultivation or incubation medium comprising at least 50, more preferably at least 75, more preferably at least 100, more preferably at least 120, more preferably at least 150 grams of precursor per liter of initial reactor or incubator volume wherein the reactor or incubator volume ranges from 250 mL to 10,000 m³ (cubic meter);
ii) Adding to the cultivation or incubation medium in a reactor or incubator at least one precursor feed comprising at least 50, more preferably at least 75, more preferably at least 100, more preferably at least 120, more preferably at least 150 grams of precursor per liter of initial reactor or incubator volume wherein the total reactor or incubator volume ranges from 250 mL (milliliter) to 10,000 m³ (cubic meter) in one pulse or in a discontinuous (pulsed), preferably so that the final volume of the cultivation or incubation medium is not more than three-fold, preferably not more than two-fold, more preferably less than two-fold of the volume of the cultivation or incubation medium before the addition of the precursor feed pulse(s);
iii) Adding to the cultivation or incubation medium in a reactor or incubator at least one precursor feed comprising at least 50, more preferably at least 75, more preferably at least 100, more preferably at least 120, more preferably at least 150 grams of precursor per liter of initial reactor or incubator volume wherein the total reactor or incubator volume ranges from 250 mL (milliliter) to 10,000 m³ (cubic meter) in one pulse or in a discontinuous (pulsed) manner, preferably so that the final volume of the cultivation or incubation medium is not more than three-fold, preferably not more than two-fold, more preferably less than two-fold of the volume of the cultivation or incubation medium before the addition of the precursor feed and wherein preferably, the pH of the precursor feed pulse(s) is set between 2.0 and 10.0 and wherein preferably, the temperature of the precursor feed pulse(s) is kept between 20° C. and 80° C.;
iv) Adding at least one precursor feed in a discontinuous (pulsed) manner to the cultivation or incubation medium over the course of 5 minutes, 10 minutes, 30 minutes, 1 hour, 2 hours, 4 hours, 10 hours, 12 hours, 1 day, 2 days, 3 days, 4 days, 5 days by means of a precursor feeding solution;
v) Adding at least one precursor feed in a discontinuous (pulsed) manner to the cultivation or incubation medium over the course of 5 minutes, 10 minutes, 30 minutes, 1 hour, 2 hours, 4 hours, 10 hours, 12 hours, 1 day, 2 days, 3 days, 4 days, 5 days by means of a precursor feeding solution and wherein the concentration of the precursor feeding solution is 50 g/L, preferably 75 g/L, more preferably 100 g/L, more preferably 125 g/L, more preferably 150 g/L, more preferably 175 g/L, more preferably 200 g/L, more preferably 225 g/L, more preferably 250 g/L, more preferably 275 g/L, more preferably 300 g/L, more preferably 325 g/L, more preferably 350 g/L, more preferably 375 g/L, more preferably, 400 g/L, more preferably 450 g/L, more preferably 500 g/L, even more preferably, 550 g/L, most preferably 600 g/L; and wherein preferably, the pH of the precursor feeding solution is set between 2.0 and 10.0 and wherein preferably, the temperature of the precursor feeding solution is kept between 20° C. and 80° C.;

The method resulting in a sialylated oligosaccharide, preferably a 3'sialylated oligosaccharide, more preferably 3'SL and/or 3'KDO-lactose, with a concentration of at least 50 g/L, preferably at least 75 g/L, more preferably at least 90 g/L, more preferably at least 100 g/L, more preferably at least 125 g/L, more preferably at least 150 g/L, more preferably at least 175 g/L, more preferably at least 200 g/L in the final volume of the cultivation or incubation. In a more preferred embodiment of the method of this disclosure, the precursor is chosen from the list comprising sialic acid, CMP-sialic acid, CMP-Neu5Ac, CMP-KDO, glucose, galactose and UDP-galactose.

In another and/or additional preferred embodiment, the method for the production of a sialylated oligosaccharide, preferably 3'sialylated oligosaccharide, as described herein comprises at least one of the following steps:
i) Use of a cultivation or incubation medium comprising at least 50, more preferably at least 75, more preferably at least 100, more preferably at least 120, more preferably at least 150 grams of acceptor per liter of initial reactor or incubator volume wherein the reactor or incubator volume ranges from 250 mL to 10,000 m³ (cubic meter);
ii) Adding to the cultivation or incubation medium in a reactor or incubator at least one acceptor feed comprising at least 50, more preferably at least 75, more preferably at least 100, more preferably at least 120, more preferably at least 150 grams of acceptor per liter of initial reactor or incubator volume wherein the total reactor or incubator volume ranges from 250 mL (milliliter) to 10,000 m³ (cubic meter) in one pulse or in a discontinuous (pulsed), preferably so that the final volume of the cultivation or incubation medium is not more than three-fold, preferably not more than two-fold, more preferably less than two-fold of the volume of the cultivation or incubation medium before the addition of the acceptor feed pulse(s);
iii) Adding to the cultivation or incubation medium in a reactor or incubator at least one acceptor feed comprising at least 50, more preferably at least 75, more preferably at least 100, more preferably at least 120, more preferably at least 150 grams of acceptor per liter of initial reactor or incubator volume wherein the total reactor or incubator volume ranges from 250 mL (milliliter) to 10,000 m$^3$ (cubic meter) in one pulse or in a discontinuous (pulsed) manner, preferably so that the final volume of the cultivation or incubation medium is not more than three-fold, preferably not more than two-fold, more preferably less than two-fold of the volume of the cultivation or incubation medium before the addition of the acceptor feed and wherein preferably, the pH of the acceptor feed pulse(s) is set between 2.0 and 10.0 and wherein preferably, the temperature of the acceptor feed pulse(s) is kept between 20° C. and 80° C.;
iv) Adding at least one acceptor feed in a discontinuous (pulsed) manner to the cultivation or incubation medium over the course of 5 minutes, 10 minutes, 30 minutes, 1 hour, 2 hours, 4 hours, 10 hours, 12 hours, 1 day, 2 days, 3 days, 4 days, 5 days by means of an acceptor feeding solution;
v) Adding at least one acceptor feed in a discontinuous (pulsed) manner to the cultivation or incubation medium over the course of 5 minutes, 10 minutes, 30 minutes, 1 hour, 2 hours, 4 hours, 10 hours, 12 hours, 1 day, 2 days, 3 days, 4 days, 5 days by means of an acceptor feeding solution and wherein the concentration of the acceptor feeding solution is 50 g/L, preferably 75 g/L, more preferably 100 g/L, more preferably 125 g/L, more preferably 150 g/L, more preferably 175 g/L, more preferably 200 g/L, more preferably 225 g/L, more preferably 250 g/L, more preferably 275 g/L, more preferably 300 g/L, more preferably 325 g/L, more preferably 350 g/L, more preferably 375 g/L, more preferably, 400 g/L, more preferably 450 g/L, more preferably 500 g/L, even more preferably, 550 g/L, most preferably 600 g/L; and wherein preferably, the pH of the acceptor feeding solution is set between 2.0 and 10.0 and wherein preferably, the temperature of the acceptor feeding solution is kept between 20° C. and 80° C.;

The method resulting in a sialylated oligosaccharide, preferably a 3'sialylated oligosaccharide, more preferably 3'SL and/or 3'KDO-lactose, with a concentration of at least 50 g/L, preferably at least 75 g/L, more preferably at least 90 g/L, more preferably at least 100 g/L, more preferably at least 125 g/L, more preferably at least 150 g/L, more preferably at least 175 g/L, more preferably at least 200 g/L in the final volume of the cultivation or incubation. In a more preferred embodiment of the method of this disclosure, the acceptor is lactose.

In a more preferred embodiment, the method for the production of a sialylated oligosaccharide, preferably 3'sialylated oligosaccharide, as described herein comprises at least one of the following steps:
i) Use of a cultivation or incubation medium comprising at least 50, more preferably at least 75, more preferably at least 100, more preferably at least 120, more preferably at least 150 grams of lactose per liter of initial reactor or incubator volume wherein the reactor or incubator volume ranges from 250 mL to 10,000 m$^3$ (cubic meter);
ii) Adding to the cultivation or incubation medium in a reactor or incubator a lactose feed comprising at least 50, more preferably at least 75, more preferably at least 100, more preferably at least 120, more preferably at least 150 gram of lactose per liter of initial reactor or incubator volume wherein the total reactor or incubator volume ranges from 250 mL (milliliter) to 10,000 m$^3$ (cubic meter), preferably in a continuous manner, and preferably so that the final volume of the cultivation or incubation medium is not more than three-fold, preferably not more than two-fold, more preferably less than two-fold of the volume of the cultivation or incubation medium before the addition of the lactose feed;
iii) Adding to the cultivation or incubation medium in a reactor or incubator a lactose feed comprising at least 50, more preferably at least 75, more preferably at least 100, more preferably at least 120, more preferably at least 150 grams of lactose per liter of initial reactor or incubator volume wherein the total reactor or incubator volume ranges from 250 mL (milliliter) to 10,000 m$^3$ (cubic meter), preferably in a continuous manner, and preferably so that the final volume of the cultivation or incubation medium is not more than three-fold, preferably not more than two-fold, more preferably less than two-fold of the volume of the cultivation or incubation medium before the addition of the lactose feed and wherein preferably, the pH of the lactose feed is set between 2.0 and 10.0, preferably between 3.0 and 7.0, and wherein preferably, the temperature of the lactose feed is kept between 20° C. and 80° C.;
iv) Adding a lactose feed in a continuous manner to the cultivation or incubation medium over the course of 1 day, 2 days, 3 days, 4 days, 5 days by means of a feeding solution;
v) Adding a lactose feed in a continuous manner to the cultivation or incubation medium over the course of 1 day, 2 days, 3 days, 4 days, 5 days by means of a feeding solution and wherein the concentration of the lactose feeding solution is 50 g/L, preferably 75 g/L, more preferably 100 g/L, more preferably 125 g/L, more preferably 150 g/L, more preferably 175 g/L, more preferably 200 g/L, more preferably 225 g/L, more preferably 250 g/L, more preferably 275 g/L, more preferably 300 g/L, more preferably 325 g/L, more preferably 350 g/L, more preferably 375 g/L, more preferably, 400 g/L, more preferably 450 g/L, more preferably 500 g/L, even more preferably, 550 g/L, most preferably 600 g/L; and wherein preferably, the pH of the lactose feed is set between 2.0 and 10.0, preferably between 3.0 and 7.0 and wherein preferably, the temperature of the lactose feed is kept between 20° C. and 80° C.;
the method resulting in a sialylated oligosaccharide, preferably a 3'sialylated oligosaccharide, more preferably 3'SL and/or 3'KDO-lactose, with a concentration of at least 50 g/L, preferably at least 75 g/L, more preferably at least 90 g/L, more preferably at least 100 g/L, more preferably at least 125 g/L, more preferably at least 150 g/L, more preferably at least 175 g/L, more preferably at least 200 g/L in the final volume of the cultivation or incubation.

Preferably the lactose feed is accomplished by adding lactose from the beginning of the cultivation or incubation in a concentration of at least 5 mM, preferably in a concentration of 30, 40, 50, 60, 70, 80, 90, 100, 150 mM, more preferably in a concentration >300 mM.

In another embodiment of the methods, the lactose feed is accomplished by adding lactose to the cultivation or incubation medium in a concentration, such that throughout the production phase of the cultivation or incubation a lactose concentration of at least 5 mM, preferably 10 mM or 30 mM is obtained.

In a further embodiment of the methods described herein the cells are cultivated or incubated for at least about 60, 80, 100, or about 120 hours or in a continuous manner.

In a preferred embodiment, a carbon source is provided, preferably sucrose, in the cultivation medium for 3 or more days, preferably up to 7 days; and/or provided, in the cultivation medium, at least 100, advantageously at least 105, more advantageously at least 110, even more advantageously at least 120 grams of sucrose per liter of initial cultivation volume in a continuous manner, so that the final volume of the cultivation medium is not more than three-fold, advantageously not more than two-fold, more advantageously less than two-fold of the volume of the cultivation medium before the cultivation.

Preferably, when performing the method as described herein, a first phase of exponential cell growth is provided by adding a carbon source, preferably glucose or sucrose, to the cultivation medium before the lactose is added to the cultivation medium in a second phase.

In an alternative preferable embodiment, in the method as described herein, the lactose is added already in the first phase of exponential growth together with the carbon-based substrate.

According to another aspect, this disclosure provides a metabolically engineered cell for the production of a sialylated oligosaccharide, preferably a 3'sialylated oligosaccharide, more preferably 3'SL (Neu5Ac-a2,3-Gal-b1,4-Glc), wherein the cell has been metabolically engineered to possess, preferably to express, more preferably to heterologously express, even more preferably to overexpress, most preferably to heterologously overexpress, a sialyltransferase that has alpha-2,3-sialyltransferase activity on the Gal residue of lactose and comprises an amino acid sequence that is i) at least 67.0% identical over a stretch of at least 150 amino acid residues, preferably at least 200 amino acid residues, to any one of the amino acid sequences as represented by SEQ ID NOs:05, 01, 02, 03, 06, 07 or 08, or ii) at least 85.0% identical over a stretch of at least 150 amino acid residues, preferably at least 200 amino acid residues, to the amino acid sequence as represented by SEQ ID NO:04 or iii) at least 60.0% identical over a stretch of at least 150 amino acid residues, preferably at least 200 amino acid residues, to the amino acid sequence as represented by SEQ ID NO:12. Preferably, the sialyltransferase used in the cell is a sialyltransferase as described herein.

In another and/or additional aspect, this disclosure provides a metabolically engineered cell for the production of a 3'sialylated oligosaccharide as described herein, wherein the cell has been metabolically engineered to possess, preferably to express, more preferably to heterologously express, even more preferably to overexpress, most preferably to heterologously overexpress, a sialyltransferase that has alpha-2,3-sialyltransferase activity on the Gal residue of lactose and comprises an amino acid sequence that is at least 80.0% identical to any one of the full-length amino acid sequences as represented by SEQ ID NOs:5, 4, 12, 1, 2, 3, 6, 7, or 8.

In a preferred embodiment of the cell hereof, the sialyltransferase comprises an amino acid sequence that is at least 80.0%, at least 85.0%, at least 90.0%, at least 95.0%, at least 96.0%, at least 97.0%, at least 98.0%, at least 98.5%, or at least 99.0% identical to any one of the full-length amino acid sequences as represented by SEQ ID NOs:5, 4, 12, 1, 2, 3, 6, 7, or 8. In an alternative preferred embodiment of the cell hereof, the sialyltransferase comprises an amino acid sequence as represented by any one of SEQ ID NOs:5, 4, 12, 1, 2, 3, 6, 7, or 8.

Alternatively or preferably, the cell contains a nucleic acid molecule that comprises a polynucleotide sequence that encodes any one of the sialyltransferases as described herein.

Herein, a metabolically engineered cell comprising a pathway for production of the sialylated oligosaccharide, preferably 3'sialylated oligosaccharide, is provided. Examples of such pathways comprise but are not limited to pathways involved in the synthesis of monosaccharide, phosphorylated monosaccharide, nucleotide-activated sugar, and/or glycosylation pathways like e.g., a fucosylation, sialylation, galactosylation, N-acetylglucosaminylation, N-acetylgalactosaminylation, mannosylation and/or N-acetylmannosaminylation pathway. The pathway for production of a sialylated oligosaccharide preferably comprises at least one sialyltransferase as described herein.

In a preferred embodiment of the method and/or cell hereof, the cell comprises one or more pathway(s) for monosaccharide synthesis. The pathways for monosaccharide synthesis comprise enzymes like e.g., carboxylases, decarboxylases, isomerases, epimerases, reductases, enolases, phosphorylases, carboxykinases, kinases, phosphatases, aldolases, hydrolases, dehydrogenases, enzymes involved in the synthesis of one or more nucleoside triphosphate(s) like UTP, GTP, ATP and CTP, enzymes involved in the synthesis of any one or more nucleoside mono- or diphosphates like e.g., UMP and UDP, respectively, and enzymes involved in the synthesis of phosphoenolpyruvate (PEP).

In another and/or additional preferred embodiment of the method and/or cell hereof, the cell comprises one or more pathway(s) for phosphorylated monosaccharide synthesis. The pathways for phosphorylated monosaccharide synthesis comprise enzymes involved in the synthesis of one or more monosaccharide(s), one or more nucleoside mono-, di- and/or triphosphate(s) and enzymes involved in the synthesis of phosphoenolpyruvate (PEP) like e.g., but not limited to PEP synthase, carboxylases, decarboxylases, isomerases, epimerases, reductases, enolases, phosphorylases, carboxykinases, kinases, phosphatases, aldolases, hydrolases and dehydrogenases. In another and/or additional preferred embodiment of the method and/or cell hereof, the cell comprises one or more pathways for the synthesis of one or more nucleotide-activated sugars. The pathways for nucleotide-activated sugar synthesis comprise enzymes like e.g., PEP synthase, carboxylases, decarboxylases, isomerases, epimerases, reductases, enolases, phosphorylases, carboxykinases, kinases, phosphatases, aldolases, hydrolases, dehydrogenases, mannose-6-phosphate isomerase, phosphomannomutase, mannose-1-phosphate guanylyltransferase, GDP-mannose 4,6-dehydratase, GDP-L-fucose synthase, L-fucokinase/GDP-fucose pyrophosphorylase, L-glutamine-D-fructose-6-phosphate aminotransferase, glucosamine-6-phosphate deaminase, phosphoglucosamine mutase, N-acetylglucosamine-6-phosphate deacetylase, N-acylglucosamine 2-epimerase, UDP-N-acetylglucosamine 2-epimerase, N-acetylglucosamine-6P 2-epimerase, glucosamine 6-phosphate N-acetyltransferase, N-acetylglucosamine-6-phosphatephosphatase, N-acetylmannosamine-6-phosphate2-epimerase, N-acetylmannosamine-6-phosphate phosphatase, N-acetylmannosamine kinase, phosphoacetylglucosamine mutase, N-acetylglucosamine-1-phosphate uridylyltransferase, glucosamine-1-phosphate acetyltransferase, sialic acid synthase, N-acetylneuraminate lyase, N-acylneuraminate-9-phosphate synthase, N-acylneuraminate-9-phosphatase, CMP-sialic acid synthase, d-arabinose 5-phosphate isomerase, KDO-8P synthase, KDO 8-phosphate phosphatase, CMP-KDO synthetase, galactose-1-epimerase, galactokinase, glucokinase, galactose-1-phosphate uridylyltransferase, UDP-glucose 4-epimerase, glucose-1-phosphate uridylyltransferase and/or phosphoglucomutase.

The cell may further comprise and express at least one further glycosyltransferase that is involved in the production of the sialylated oligosaccharide, preferably 3'sialylated oligosaccharide.

In a preferred embodiment of the method and/or cell hereof, the cell is metabolically engineered to comprise a pathway for production of a sialylated oligosaccharide as defined herein, preferably for production of a 3'sialylated oligosaccharide, more preferably 3'SL and/or 3'KDO-lactose, as defined herein. In an alternative preferred embodiment of the method and/or cell hereof, the cell is metabolically engineered to comprise a pathway for production of a sialylated oligosaccharide as defined herein, preferably for production of a 3'sialylated oligosaccharide, preferably 3'SL and/or 3'KDO-lactose, and to have modified expression or activity of a sialyltransferase hereof.

In a further preferred embodiment of the method and/or cell hereof, the cell comprises a recombinant sialyltransferase capable of modifying lactose or another acceptor as defined herein with one or more sialic acid molecules that is/are synthesized by any one or more sialic acid synthases like e.g., Neu5Ac synthases, or by e.g., d-arabinose 5-phosphate isomerase, KDO-8P synthase and KDO 8-phosphate phosphatase expressed in the cell, into a sialylated oligosaccharide, preferably a 3'sialylated oligosaccharide, more preferably 3'SL and/or 3'KDO-lactose.

In a preferred embodiment of the method and/or cell of this disclosure, the metabolically engineered cell is modified with one or more expression modules.

The expression modules are also known as transcriptional units and comprise polynucleotides for expression of recombinant genes including coding gene sequences and appropriate transcriptional and/or translational control signals that are operably linked to the coding genes. The control signals comprise promoter sequences, untranslated regions, ribosome binding sites, terminator sequences. The expression modules can contain elements for expression of one single recombinant gene but can also contain elements for expression of more recombinant genes or can be organized in an operon structure for integrated expression of two or more recombinant genes. The polynucleotides may be produced by recombinant DNA technology using techniques well-known in the art. Methods that are well known to those skilled in the art to construct expression modules include, for example, in vitro recombinant DNA techniques, synthetic techniques, and in vivo genetic recombination. See, for example, the techniques described in Sambrook et al. (2001) Molecular Cloning: a laboratory manual, 3rd Edition, Cold Spring Harbor Laboratory Press, CSH, New York or to Current Protocols in Molecular Biology, John Wiley and Sons, N.Y. (1989 and yearly updates).

The expression of each of the expression modules can be constitutive or is created by a natural or chemical inducer. As used herein, constitutive expression should be understood as expression of a gene that is transcribed continuously in an organism. Expression that is created by a natural inducer should be understood as a facultative or regulatory expression of a gene that is only expressed upon a certain natural condition of the host (e.g., organism being in labor, or during lactation), as a response to an environmental change (e.g., including but not limited to hormone, heat, cold, pH shifts, light, oxidative or osmotic stress/signaling), or dependent on the position of the developmental stage or the cell cycle of the host cell including but not limited to apoptosis and autophagy. Expression that is created by a chemical inducer should be understood as a facultative or regulatory expression of a gene that is only expressed upon sensing of external chemicals (e.g., IPTG, arabinose, lactose, allo-lactose, rhamnose or fucose) via an inducible promoter or via a genetic circuit that either induces or represses the transcription or translation of the polynucleotide to a polypeptide.

The expression modules can be integrated in the genome of the cell or can be presented to the cell on a vector. The vector can be present in the form of a plasmid, cosmid, phage, liposome, or virus, which is to be stably transformed/transfected into the metabolically engineered cell. Such vectors include, among others, chromosomal, episomal and virus-derived vectors, e.g., vectors derived from bacterial plasmids, from bacteriophage, from transposons, from yeast episomes, from insertion elements, from yeast chromosomal elements, from viruses, and vectors derived from combinations thereof, such as those derived from plasmid and bacteriophage genetic elements, such as cosmids and phagemids. These vectors may contain selection markers such as but not limited to antibiotic markers, auxotrophic markers, toxin-antitoxin markers, RNA sense/antisense markers. The expression system constructs may contain control regions that regulate as well as engender expression. Generally, any system or vector suitable to maintain, propagate or express polynucleotides and/or to express a polypeptide in a host may be used for expression in this regard. The appropriate DNA sequence may be inserted into the expression system by any of a variety of well-known and routine techniques, such as, for example, those set forth in Sambrook et al., see above. For recombinant production, cells can be genetically engineered to incorporate expression systems or portions thereof or polynucleotides of the invention. Introduction of a polynucleotide into the cell can be effected by methods described in many standard laboratory manuals, such as Davis et al., Basic Methods in Molecular Biology, (1986), and Sambrook et al., 1989, supra.

As used herein an expression module comprises polynucleotides for expression of at least one recombinant gene. The recombinant gene is involved in the expression of a polypeptide acting in the synthesis of a sialylated oligosaccharide, preferably a 3'sialylated oligosaccharide, such as e.g., 3'SL and/or 3'KDO-lactose; or the recombinant gene is linked to other pathways in the cell that are not involved in the synthesis of a sialylated oligosaccharide. The recombinant genes encode endogenous proteins with a modified expression or activity, preferably the endogenous proteins are overexpressed; or the recombinant genes encode heterologous proteins that are heterogeneously introduced and expressed in the modified cell, preferably overexpressed. The endogenous proteins can have a modified expression in the cell that also expresses a heterologous protein.

In a preferred embodiment of the method and/or cell of this disclosure, the expression of each of the expression modules present in the metabolically engineered cell is constitutive or tuneable as described herein.

In a further embodiment of the method and/or cell of this disclosure, the cell is modified in the expression or activity of at least one of the sialyltransferases. In a preferred embodiment, the sialyltransferase is an endogenous protein of the cell with a modified expression or activity, preferably the endogenous sialyltransferase is overexpressed; alternatively the sialyltransferase is a heterologous protein that is heterogeneously introduced and expressed in the cell, preferably overexpressed. The endogenous sialyltransferase can have a modified expression in the cell that also expresses a heterologous sialyltransferase.

According to a preferred embodiment of the method and/or cell of this disclosure, the cell comprises a pathway for production of a sialylated oligosaccharide, preferably a 3'sialylated oligosaccharide, more preferably 3'SL, comprising at least one sialyltransferase according to present invention. According to another preferred embodiment of the method and/or cell of this disclosure, the pathway for production of a sialylated oligosaccharide, preferably a 3'sialylated oligosaccharide, more preferably 3'SL, further comprises at least one enzyme chosen from the list comprising L-glutamine-D-fructose-6-phosphate aminotransferase, a phosphoglucosamine mutase, an N-acetylglucosamine-6-P deacetylase, an N-acylglucosamine 2-epimerase, a UDP-N-acetylglucosamine 2-epimerase, an N-acetylmannosamine-6-phosphate 2-epimerase, a UDP-GlcNAc 2-epimerase/kinase, a glucosamine 6-phosphate N-acetyltransferase, an N-acetylglucosamine-6-phosphate phosphatase, a phosphoacetylglucosamine mutase, an N-acetylglucosamine 1-phosphate uridylyltransferase, a glucosamine-1-phosphate acetyltransferase, an Neu5Ac synthase, an N-acetylneuraminate lyase, an N-acylneuraminate-9-phosphate synthase, an N-acylneuraminate-9-phosphatase, a sialic acid transporter and a CMP-sialic acid synthase.

In another and/or additional preferred embodiment of the method and/or cell of this disclosure, the cell comprises a pathway for production of a 3'sialylated oligosaccharide, like e.g., 3'KDO-lactose, comprising at least one sialyltransferase according to present invention. According to another preferred embodiment of the method and/or cell of this disclosure, the pathway for production of a 3'sialylated oligosaccharide, preferably 3'KDO-lactose further comprises at least one enzyme chosen from the list comprising a d-arabinose 5-phosphate isomerase, a KDO-8P synthase, a KDO 8-phosphate phosphatase and a CMP-KDO synthetase.

In a preferred embodiment, the cell comprises a pathway for production of a sialylated oligosaccharide, preferably a 3'sialylated oligosaccharide, more preferably 3'SL, wherein the cell expresses at least one enzyme chosen from the list comprising an N-acylglucosamine 2-epimerase like is known e.g., from several species including *Bacteroides ovatus, E. coli, Homo sapiens, Rattus norvegicus*, a Neu5Ac synthase, a CMP sialic acid synthase like is known e.g., from *Neisseria meningitidis*, and a sialyltransferase according to present invention, wherein the enzymes are as defined herein. N-acetylglucosamine (GlcNAc) can be added to the cell and/or can be provided by an enzyme expressed in the cell or by the mechanism of the cell. Such cell producing GlcNAc can express a phosphatase converting GlcNAc-6-phosphate into GlcNAc, like any one or more of e.g., the *E. coli* HAD-like phosphatase genes comprising aphA, Cof, HisB, OtsB, SurE, Yaed, YcjU, YedP, YfbT, YidA, YigB, YihX, YniC, YqaB, YrbL, AppA, Gph, SerB, YbhA, YbiV, YbjL, Yfb, YieH, YjgL, YjjG, YrfG and YbiU, PsMupP from *Pseudomonas putida*, ScDOG1 from *S. cerevisiae* and BsAraL from *Bacillus subtilis* as described in WO18122225. Preferably, the cell is modified to produce GlcNAc. More preferably, the cell is modified for enhanced GlcNAc production. The modification can be any one or more chosen from the group comprising knockout of a glucosamine-6-phosphate deaminase, an N-acetylglucosamine-6-phosphate deacetylase and/or an N-acetyl-D-glucosamine kinase and over-expression of an L-glutamine-D-fructose-6-phosphate aminotransferase and/or a glucosamine 6-phosphate N-acetyltransferase.

In an alternative and/or additional preferred embodiment, the cell comprises a pathway for production of a sialylated oligosaccharide, preferably a 3'sialylated oligosaccharide, more preferably 3'SL, wherein the cell expresses at least one enzyme chosen from the list comprising an UDP-N-acetylglucosamine 2-epimerase like is known e.g., from several species including *Campylobacter jejuni, E. coli, Neisseria meningitidis, Bacillus subtilis, Citrobacter rodentium*, a Neu5Ac synthase, a CMP sialic acid synthase like is known e.g., from *Neisseria meningitidis*, and a sialyltransferase according to present invention, wherein the enzymes are as defined herein. UDP-N-acetylglucosamine (UDP-GlcNAc) can be added to the cell and/or can be provided by an enzyme expressed in the cell or by the metabolism of the cell. Such cell producing an UDP-GlcNAc can express enzymes converting, e.g., GlcNAc, which is to be added to the cell, to UDP-GlcNAc. These enzymes may be any one or more enzymes chosen from the list comprising an N-acetyl-D-glucosamine kinase, an N-acetylglucosamine-6-phosphate deacetylase, a phosphoglucosamine mutase, and an N-acetylglucosamine-1-phosphate uridylyltransferase/ glucosamine-1-phosphate acetyltransferase from several species including *Homo sapiens, Escherichia coli*. Preferably, the cell is modified to produce UDP-GlcNAc. More preferably, the cell is modified for enhanced UDP-GlcNAc production. The modification can be any one or more chosen from the group comprising knock-out of an N-acetylglucosamine-6-phosphate deacetylase, over-expression of an L-glutamine-D-fructose-6-phosphate aminotransferase, over-expression of a phosphoglucosamine mutase, and over-expression of an N-acetylglucosamine-1-phosphate uridylyltransferase/glucosamine-1-phosphate acetyltransferase.

In an alternative and/or additional preferred embodiment, the cell comprises a pathway for production of a sialylated oligosaccharide, preferably a 3'sialylated oligosaccharide, more preferably 3'SL, wherein the cell expresses at least one enzyme chosen from the list comprising an N-acetylmannosamine-6-phosphate 2-epimerase like is known e.g., from several species including *E. coli, Haemophilus influenzae, Enterobacter* sp., *Streptomyces* sp., an N-acylneuraminate-9-phosphate synthetase, an N-acylneuraminate-9-phosphatase like is known e.g., from *Candidatus Magnetomorum* sp. HK-1 or *Bacteroides thetaiotaomicron*, a Neu5Ac synthase, a CMP sialic acid synthase like is known e.g., from *Neisseria meningitidis*, and a sialyltransferase according to present invention, wherein the enzymes are as defined herein. N-acetyl-D-glucosamine 6-phosphate (GlcNAc-6P) can be added to the cell and/or can be provided by an enzyme expressed in the cell or by the metabolism of the cell. Such cell producing GlcNAc-6P can express an enzyme converting, e.g., GlcN6P, which is to be added to the cell, to GlcNAc-6P. This enzyme may be a glucosamine 6-phosphate N-acetyltransferase from several species including *Saccharomyces cerevisiae, Kluyveromyces lactis, Homo sapiens*. Preferably, the cell is modified to produce GlcNAc- 6P. More preferably, the cell is modified for enhanced GlcNAc-6P production. The modification can be any one or more chosen from the group comprising knockout of a glucosamine-6-phosphate deaminase, an N-acetylglucosamine-6-phosphate deacetylase and over-expression of an L-glutamine-D-fructose-6-phosphate aminotransferase and/or a glucosamine 6-phosphate N-acetyltransferase.

In an alternative and/or additional preferred embodiment, the cell comprises a pathway for production of a sialylated oligosaccharide, preferably a 3'sialylated oligosaccharide, more preferably 3'SL, wherein the cell expresses at least one enzyme chosen from the list comprising a bifunctional UDP-GlcNAc 2-epimerase/kinase like is known e.g., from several species including *Homo sapiens, Rattus norvegicus* and *Mus musculus*, an N-acylneuraminate-9-phosphate synthetase, an N-acylneuraminate-9-phosphatase like is known e.g., from *Candidatus Magnetomorum* sp. HK-1 or *Bacteroides thetaiotaomicron*, a Neu5Ac synthase, a CMP sialic acid synthase like is known e.g., from *Neisseria meningitidis*, and a sialyltransferase according to present invention, wherein the enzymes are as defined herein. UDP-N-acetylglucosamine can be added to the cell and/or can be provided by an enzyme expressed in the cell or by the metabolism of the cell. Such cell producing an UDP-GlcNAc can express enzymes converting, e.g., GlcNAc, which is to be added to the cell, to UDP-GlcNAc. These enzymes may be an N-acetyl-D-glucosamine kinase, an N-acetylglucosamine-6-phosphate deacetylase, a phosphoglucosamine mutase, and an N-acetylglucosamine-1-phosphate uridylyltransferase/glucosamine-1-phosphate acetyltransferase from several species including *Homo sapiens, Escherichia coli*. Preferably, the cell is modified to produce UDP-GlcNAc. More preferably, the cell is modified for enhanced UDP-GlcNAc production. The modification can be any one or more chosen from the group comprising knock-out of an N-acetylglucosamine-6-phosphate deacetylase, over-expression of an L-glutamine-D-fructose-6-phosphate aminotransferase, over-expression of a phosphoglucosamine mutase, and over-expression of an N-acetylglucosamine-1-phosphate uridylyltransferase/glucosamine-1-phosphate acetyltransferase.

In an alternative and/or additional preferred embodiment, the cell comprises a pathway for production of a 3'sialylated oligosaccharide, preferably 3'KDO-lactose, wherein the cell expresses at least one enzyme chosen from the list comprising a d-arabinose 5-phosphate isomerase, a KDO-8P synthase, a KDO 8-phosphate phosphatase, a CMP-KDO synthetase from different species like e.g., *Escherichia coli, Pseudomonas aeruginosa, Agrobacterium* sp. and a sialyltransferase according to present invention, wherein the enzymes are as defined herein. Preferably, the cell is capable of making CMP-KDO. More preferably, the cell is modified to produce CMP-KDO. More preferably, the cell is modified for enhanced CMP-KDO production. The modification can be any one or more chosen from the group comprising over-expression of a d-arabinose 5-phosphate isomerase, a KDO-8P synthase, a KDO 8-phosphate phosphatase and/or a CMP-KDO synthetase encoding gene.

Additionally, or alternatively, the cell used herein is optionally genetically engineered to import a precursor and/or an acceptor in the cell, by the introduction and/or overexpression of a transporter able to import the respective precursor and/or acceptor in the cell. Such transporter is, for example, a membrane protein belonging to the major facilitator superfamily (MFS), the ATP-binding cassette (ABC) transporter family or the PTS system involved in the uptake of e.g., mono-, di- and/or oligosaccharides.

Additionally, or alternatively, the cell used herein is optionally genetically engineered to produce polyisoprenoid alcohols like e.g., phosphorylated dolichol that can act as lipid carrier.

Additionally, or alternatively, the cell used herein is optionally genetically engineered to import lactose in the cell, by the introduction and/or overexpression of a lactose permease. The lactose permease is, for example, encoded by the lacY gene or the lac12 gene.

Additionally, or alternatively, the cell expresses a membrane protein that is a transporter protein involved in transport of compounds and/or a sialylated oligosaccharide as defined in present invention out of the cell. In the context hereof, it should be understood that the sialylated oligosaccharide, preferably 3'sialylated oligosaccharide, more preferably 3'SL and/or 3'KDO-lactose, is preferably produced intracellularly. The skilled person will further understand that a fraction or substantially all of the produced sialylated oligosaccharide, preferably 3'sialylated oligosaccharide, remains intracellularly and/or is excreted outside the cell either passively or through active transport.

In a preferred embodiment of the method and/or cell of this disclosure, the cell expresses a membrane transporter protein or a polypeptide having transport activity hereby transporting compounds across the outer membrane of the cell wall. In another preferred embodiment of the method and/or cell of this disclosure, the cell expresses more than one membrane transporter protein or polypeptide having transport activity hereby transporting compounds across the outer membrane of the cell wall. In a more preferred embodiment of the method and/or cell of this disclosure, the cell is modified in the expression or activity of the membrane transporter protein or polypeptide having transport activity. The membrane transporter protein or polypeptide having transport activity is an endogenous protein of the cell with a modified expression or activity, preferably the endogenous membrane transporter protein or polypeptide having transport activity is overexpressed; alternatively the membrane transporter protein or polypeptide having transport activity is a heterologous protein that is heterogeneously introduced and expressed in the cell, preferably overexpressed. The endogenous membrane transporter protein or polypeptide having transport activity can have a modified expression in the cell that also expresses a heterologous membrane transporter protein or polypeptide having transport activity.

In a more preferred embodiment of the method and/or cell of this disclosure, the membrane transporter protein or polypeptide having transport activity is chosen from the list comprising porters, P-P-bond-hydrolysis-driven transporters, b-barrel porins, auxiliary transport proteins and phosphotransfer-driven group translocators. In an even more preferred embodiment of the method and/or cell of this disclosure, the porters comprise MFS transporters, sugar efflux transporters and siderophore exporters. In another more preferred embodiment of the method and/or cell of this disclosure, the P-P-bond-hydrolysis-driven transporters comprise ABC transporters and siderophore exporters.

In another preferred embodiment of the method and/or cell of this disclosure, the membrane transporter protein or polypeptide having transport activity controls the flow over the outer membrane of the cell wall of the sialylated oligosaccharide. In an alternative and/or additional preferred embodiment of the method and/or cell of this disclosure, the membrane transporter protein or polypeptide having transport activity controls the flow over the outer membrane of the cell wall of one or more precursor(s) to be used in the production of the sialylated oligosaccharide, preferably 3'sialylated oligosaccharide.

In another preferred embodiment of the method and/or cell of this disclosure, the membrane transporter protein or polypeptide having transport activity provides improved production of the sialylated oligosaccharide. In an alternative and/or additional preferred embodiment of the method and/or cell of this disclosure, the membrane transporter protein or polypeptide having transport activity provides enabled efflux of the sialylated oligosaccharide, preferably 3'sialylated oligosaccharide. In an alternative and/or additional preferred embodiment of the method and/or cell of this disclosure, the membrane transporter protein or polypeptide having transport activity provides enhanced efflux of the sialylated oligosaccharide, preferably 3'sialylated oligosaccharide.

Preferably the cell is transformed to comprise at least one nucleic acid sequence encoding a protein selected from the group comprising a lactose transporter like e.g., the LacY or lac12 permease, a glucose transporter, a galactose transporter, a transporter for a nucleotide-activated sugar like, for example, a transporter for UDP-GlcNAc, a transporter protein involved in transport of a sialylated oligosaccharide, preferably a 3'sialylated oligosaccharide, more preferably 3'SL and/or 3'KDO-lactose, out of the cell.

In another preferred embodiment of the method and/or cell of this disclosure, the cell expresses a membrane transporter protein belonging to the family of MFS transporters like e.g., an MdfA polypeptide of the multidrug transporter MdfA family from species comprising *E. coli* (UniProt ID P0AEY8), *Cronobacter muytjensii* (UniProt ID AOA2T7ANQ9), *Citrobacter youngae* (UniProt ID D4BC23) and *Yokenella regensburgei* (UniProt ID G9Z5F4). In another preferred embodiment of the method and/or cell of this disclosure, the cell expresses a membrane transporter protein belonging to the family of sugar efflux transporters like e.g., a SetA polypeptide of the SetA family from species comprising *E. coli* (UniProt ID P31675, sequence version 03 (11 Oct. 2004)) and *Citrobacter koseri* (UniProt ID AOA078LM16). In another preferred embodiment of the method and/or cell of this disclosure, the cell expresses a membrane transporter protein belonging to the family of siderophore exporters like e.g., the *E. coli* entS (UniProt ID P24077, sequence version 02 (1 Nov. 1997)), the *K. ascorbata* entS (UniProt ID A0A378GQ13) and the *E. coli* iceT (UniProt ID A0A024L207). In another preferred embodiment of the method and/or cell of this disclosure, the cell expresses a membrane transporter protein belonging to the family of ABC transporters like e.g., oppF from *E. coli* (UniProt ID P77737), lmrA from *Lactococcus lactis* subsp. *lactis* bv. *diacetylactis* (UniProt ID AOAIVONEL4) and Blon_2475 from *Bifidobacterium longum* subsp. *infantis* (UniProt ID B7GPD4). In a more preferred embodiment of the method and/or cell of this disclosure, the cell expresses more than one membrane transporter protein chosen from the list comprising a lactose transporter like e.g., the LacY or lac12 permease, a fucose transporter, a glucose transporter, a galactose transporter, a transporter for a nucleotide-activated sugar like, for example, a transporter for UDP-GlcNAc, UDP-Gal and/or GDP-Fuc, the MdfA protein from *E. coli* (UniProt ID P0AEY8), the MdfA protein from *Cronobacter muytjensii* (UniProt ID AOA2T7ANQ9), the MdfA protein from *Citrobacter youngae* (UniProt ID D4BC23), the MdfA protein from *Yokenella regensburgei* (UniProt ID G9Z5F4), the SetA protein from *E. coli* (UniProt ID P31675, sequence version 03 (11 Oct. 2004)), the SetA protein from *Citrobacter koseri* (UniProt ID AOA078LM16), the entS protein from *E. coli* (UniProt ID P24077, sequence version 02 (1 Nov. 1997)), the entS protein from *K. ascorbata* (UniProt ID A0A378GQ13), the iceT protein from *E. coli* (UniProt ID A0A024L207), the oppF protein from *E. coli* (UniProt ID P77737), the lmrA protein from *Lactococcus lactis* subsp. *lactis* bv. *diacetylactis* (UniProt ID A0A1V0NEL4) and Blon_2475 from *Bifidobacterium longum* subsp. *infantis* (UniProt ID B7GPD4).

Preferably the cell is transformed to comprise at least one nucleic acid sequence encoding a membrane transporter protein selected from the group comprising a siderophore exporter, a major facilitator superfamily (MFS) transporter, an ATP-binding cassette (ABC) transporter or a sugar efflux transporter.

According to another preferred aspect of the method and/or cell of this disclosure, the cell is capable of synthesizing N-acetylmannosamine (ManNAc), N-acetylmannosamine-6-phosphate (ManNAc-6-phosphate) and/or phosphoenolpyruvate (PEP).

In a preferred embodiment, the cell comprises a pathway for production of a sialylated oligosaccharide, preferably a 3'sialylated oligosaccharide, more preferably 3'SL and/or 3'KDO-lactose, comprising a pathway for production of ManNAc. ManNAc can be provided by an enzyme expressed in the cell or by the mechanism of the cell. Such cell producing ManNAc can express an N-acylglucosamine 2-epimerase like is known e.g., from several species including *Bacteroides ovatus, E. coli, Homo sapiens, Rattus norvegicus* that converts GlcNAc into ManNAc. Alternatively, and/or additionally, the cell producing ManNAc can express an UDP-N-acetylglucosamine 2-epimerase like is known e.g., from several species including *Campylobacter jejuni, E. coli, Neisseria meningitidis, Bacillus subtilis, Citrobacter rodentium* that converts UDP-GlcNAc into ManNAc. GlcNAc and/or UDP-GlcNAc can be added to the cell and/or provided by an enzyme expressed in the cell or by the mechanism of the cell as described herein.

In a more preferred embodiment, the cell is modified for enhanced ManNAc production. The modification can be any one or more chosen from the group comprising knock-out of N-acetylmannosamine kinase, over-expression of N-acetylneuraminate lyase.

In another preferred embodiment, the cell comprises a pathway for production of a sialylated oligosaccharide, preferably a 3'sialylated oligosaccharide, more preferably 3'SL and/or 3'KDO-lactose, comprising a pathway for production of ManNAc-6-phosphate. ManNAc-6-phosphate can be provided by an enzyme expressed in the cell or by the mechanism of the cell. Such cell producing ManNAc-6-phosphate can express a bifunctional UDP-GlcNAc 2-epimerase/kinase like is known e.g., from several species including *Homo sapiens, Rattus norvegicus* and *Mus musculus* that converts UDP-GlcNAc into ManNAc-6-phosphate. Alternatively, and/or additionally, the cell producing ManNAc-6-phosphate can express an N-acetylmannosamine-6-phosphate 2-epimerase that converts GlcNAc-6-phosphate into ManNAc-6-phosphate. UDP-GlcNAc and/or GlcNAc-6-phosphate can be added to the cell and/or provided by an enzyme expressed in the cell or by the mechanism of the cell as described herein. In a more preferred embodiment, the cell is modified for enhanced ManNAc-6-phosphate production. The modification can be any one or more chosen from the group comprising over-expression of N-acetylglucosamine-6-phosphate deacetylase, over-expression of N-acetyl-D-glucosamine kinase, over-expression of phosphoglucosamine mutase, over-expression of N-acetylglucosamine-1-phosphate uridylyltransferase/glucosamine-1-phosphate acetyltransferase.

According to another embodiment of the method and/or cell of this disclosure, the cell is further capable of synthesizing any one or more nucleotide-activated sugars. In a preferred embodiment of the method and/or cell of this disclosure, the cell is capable of synthesizing one or more nucleotide-activated sugars chosen from the list comprising UDP-N-acetylglucosamine (UDP-GlcNAc), UDP-N-acetylgalactosamine (UDP-GalNAc), UDP-N-acetylmannosamine (UDP-ManNAc), UDP-glucose (UDP-Glc), UDP-galactose (UDP-Gal), GDP-mannose (GDP-Man), UDP-glucuronate, UDP-galacturonate, UDP-2-acetamido-2,6-dideoxy-L-arabino-4-hexulose, UDP-2-acetamido-2,6-dideoxy-L-lyxo-4-hexulose, UDP-N-acetyl-L-rhamnosamine (UDP-L-RhaNAc or UDP-2-acetamido-2,6-dideoxy-L-mannose), dTDP-N-acetylfucosamine, UDP-N-acetylfucosamine (UDP-L-FucNAc or UDP-2-acetamido-2,6-dideoxy-L-galactose), UDP-N-acetyl-L-pneumosamine (UDP-L-PneNAC or UDP-2-acetamido-2,6-dideoxy-L-talose), UDP-N-acetylmuramic acid, UDP-N-acetyl-L-quinovosamine (UDP-L-QuiNAc or UDP-2-acetamido-2,6-dideoxy-L-glucose), CMP-sialic acid (e.g., CMP-Neu5Ac, CMP-Neu4Ac, CMP-Neu5Ac9N$_3$, CMP-Neu4,5Ac$_2$, CMP-Neu5,7Ac$_2$, CMP-Neu5,9Ac$_2$, CMP-Neu5,7(8,9)Ac$_2$, CMP-Neu5Gc or CMP-KDO), GDP-fucose (GDP-Fuc), GDP-rhamnose and UDP-xylose. In a more preferred embodiment of the method and/or cell of this disclosure, the cell is capable of synthesizing at least the nucleotide-activated sugar CMP-Neu5Ac. In another more preferred embodiment of the method and/or cell of this disclosure, the cell is capable of synthesizing at least the nucleotide-activated sugar CMP-KDO. In an even more preferred embodiment of the method and/or cell of this disclosure, the cell uses at least one of the synthesized nucleotide-activated sugars in the production of a sialylated oligosaccharide, preferably a 3'sialylated oligosaccharide, more preferably 3'SL and/or 3'KDO-lactose.

The cell used herein is optionally genetically engineered to express the de novo synthesis of UDP-GlcNAc. UDP-GlcNAc can be provided by an enzyme expressed in the cell or by the metabolism of the cell. Such cell producing an UDP-GlcNAc can express enzymes converting, e.g., GlcNAc, which is to be added to the cell, to UDP-GlcNAc. These enzymes may be any one or more of the list comprising an N-acetyl-D-glucosamine kinase, an N-acetylglucosamine-6-phosphate deacetylase, a phosphoglucosamine mutase, and an N-acetylglucosamine-1-phosphate uridylyltransferase/glucosamine-1-phosphate acetyltransferase from several species including *Homo sapiens, E. coli*. Preferably, the cell is modified to produce UDP-GlcNAc. More preferably, the cell is modified for enhanced UDP-GlcNAc production. The modification can be any one or more chosen from the group comprising knock-out of an N-acetylglucosamine-6-phosphate deacetylase, over-expression of an L-glutamine-D-fructose-6-phosphate aminotransferase, over-expression of a phosphoglucosamine mutase, and over-expression of an N-acetylglucosamine-1-phosphate uridylyltransferase/glucosamine-1-phosphate acetyltransferase.

Additionally, or alternatively, the cell used herein is optionally genetically engineered to express the de novo synthesis of CMP-Neu5Ac. CMP-Neu5Ac can be provided by an enzyme expressed in the cell or by the metabolism of the cell. Such cell producing CMP-Neu5Ac can express an enzyme converting, e.g., sialic acid to CMP-Neu5Ac. This enzyme may be a CMP-sialic acid synthetase, like the N-acylneuraminate cytidylyltransferase from several species including *Homo sapiens, Neisseria meningitidis*, and *Pasteurella multocida*. Preferably, the cell is modified to produce CMP-Neu5Ac. More preferably, the cell is modified for enhanced CMP-Neu5Ac production. The modification can be any one or more chosen from the group comprising knock-out of an N-acetylglucosamine-6-phosphate deacetylase, knock-out of a glucosamine-6-phosphate deaminase, over-expression of a CMP-sialic acid synthetase, and over-expression of an N-acetyl-D-glucosamine-2-epimerase encoding gene.

Additionally, or alternatively, the cell used herein is optionally genetically engineered to express the de novo synthesis of CMP-KDO. CMP-KDO can be provided by an enzyme expressed in the cell or by the metabolism of the cell. Such cell producing CMP-KDO can express an enzyme converting, e.g., KDO to CMP-KDO. This enzyme may be a CMP-KDO synthetase, like the 3-deoxy-manno-octulosonate cytidylyltransferase kdsB from several species including *E. coli, Arabidopsis thaliana, Pseudomonas aeruginosa, Xanthomonas campestris*. Preferably, the cell is modified to produce CMP-KDO. More preferably, the cell is modified for enhanced CMP-KDO production. The modification can be any one or more chosen from the group comprising over-expression of a d-arabinose 5-phosphate isomerase, a KDO-8P synthase, a KDO 8-phosphate phosphatase and/or a CMP-KDO synthetase encoding gene.

Additionally, or alternatively, the cell used herein is optionally genetically engineered to express the de novo synthesis of GDP-fucose. GDP-fucose can be provided by an enzyme expressed in the cell or by the metabolism of the cell. Such cell producing GDP-fucose can express an enzyme converting, e.g., fucose, which is to be added to the cell, to GDP-fucose. This enzyme may be, e.g., a bifunctional fucose kinase/fucose-1-phosphate guanylyltransferase, like Fkp from *Bacteroides fragilis*, or the combination of one separate fucose kinase together with one separate fucose-1-phosphate guanylyltransferase like they are known from several species including *Homo sapiens, Sus scrofa* and *Rattus norvegicus*. Preferably, the cell is modified to produce GDP-fucose. More preferably, the cell is modified for enhanced GDP-fucose production. The modification can be any one or more chosen from the group comprising knock-out of an UDP-glucose:undecaprenyl-phosphate glucose-1-phosphate transferase encoding gene, over-expression of a GDP-L-fucose synthase encoding gene, over-expression of a GDP-mannose 4,6-dehydratase encoding gene, over-expression of a mannose-1-phosphate guanylyltransferase encoding gene, over-expression of a phosphomannomutase encoding gene and over-expression of a mannose-6-phosphate isomerase encoding gene.

Additionally, or alternatively, the cell used herein is optionally genetically engineered to express the de novo synthesis of UDP-Gal. UDP-Gal can be provided by an enzyme expressed in the cell or by the metabolism of the cell. Such cell producing UDP-Gal can express an enzyme converting, e.g., UDP-glucose, to UDP-Gal. This enzyme may be, e.g., the UDP-glucose-4-epimerase GalE like as known from several species including *Homo sapiens, E. coli*, and *Rattus norvegicus*. Preferably, the cell is modified to produce UDP-Gal. More preferably, the cell is modified for enhanced UDP-Gal production. The modification can be any one or more chosen from the group comprising knock-out of a bifunctional 5'-nucleotidase/UDP-sugar hydrolase encoding gene, knock-out of a galactose-1-phosphate uridylyltransferase encoding gene and over-expression of a UDP-glucose-4-epimerase encoding gene.

Additionally, or alternatively, the cell used herein is optionally genetically engineered to express the de novo synthesis of UDP-GalNAc. UDP-GalNAc can be synthesized from UDP-GlcNAc by the action of a single-step reaction using a UDP-N-acetylglucosamine 4-epimerase like e.g., wbgU from *Plesiomonas shigelloides*, gne from *Yersinia enterocolitica* or wbpP from *Pseudomonas aeruginosa* serotype 06. Preferably, the cell is modified to produce UDP-GalNAc. More preferably, the cell is modified for enhanced UDP-GalNAc production.

Additionally, or alternatively, the cell used herein is optionally genetically engineered to express the de novo synthesis of UDP-ManNAc. UDP-ManNAc can be synthesized directly from UDP-GlcNAc via an epimerization reaction performed by a UDP-GlcNAc 2-epimerase (like e.g., cap5P from *Staphylococcus aureus*, RffE from *E. coli*, Cps19fK from *S. pneumoniae*, and RfbC from *S. enterica*). Preferably, the cell is modified to produce UDP-ManNAc. More preferably, the cell is modified for enhanced UDP-ManNAc production.

According to another embodiment of the method and/or cell of this disclosure, the cell expresses at least one further glycosyltransferase chosen from the list comprising fucosyltransferases, sialyltransferases, galactosyltransferases, glucosyltransferases, mannosyltransferases, N-acetylglucosaminyltransferases, N-acetylgalactosaminyltransferases, N-acetylmannosaminyltransferases, xylosyltransferases, glucuronyltransferases, galacturonyltransferases, glucosaminyltransferases, N-glycolylneuraminyltransferases, rhamnosyltransferases, N-acetylrhamnosyltransferases, UDP-4-amino-4,6-dideoxy-N-acetyl-beta-L-altrosamine transaminases, UDP-N-acetylglucosamine enolpyruvyl transferases and fucosaminyltransferases.

In a preferred embodiment of the method and/or cell of this disclosure, the fucosyltransferase is chosen from the list comprising alpha-1,2-fucosyltransferase, alpha-1,3-fucosyltransferase, alpha-1,3/4-fucosyltransferase, alpha-1,4-fucosyltransferase and alpha-1,6-fucosyltransferase.

In an alternative and/or additional embodiment of the method and/or cell of this disclosure, the further sialyltransferase is chosen from the list comprising alpha-2,3-sialyltransferase, alpha-2,6-sialyltransferase, and alpha-2,8-sialyltransferase.

In an alternative and/or additional embodiment of the method and/or cell of this disclosure, the galactosyltransferase is chosen from the list comprising beta-1,3-galactosyltransferase, N-acetylglucosamine beta-1,3-galactosyltransferase, beta-1,4-galactosyltransferase, N-acetylglucosamine beta-1,4-galactosyltransferase, alpha-1,3-galactosyltransferase and alpha-1,4-galactosyltransferase.

In an alternative and/or additional embodiment of the method and/or cell of this disclosure, the glucosyltransferase is chosen from the list comprising alpha-glucosyltransferase, beta-1,2-glucosyltransferase, beta-1,3-glucosyltransferase and beta-1,4-glucosyltransferase.

In an alternative and/or additional embodiment of the method and/or cell of this disclosure, the mannosyltransferase is chosen from the list comprising alpha-1,2-mannosyltransferase, alpha-1,3-mannosyltransferase and alpha-1,6-mannosyltransferase.

In an alternative and/or additional embodiment of the method and/or cell of this disclosure, the N-acetylglucosaminyltransferase is chosen from the list comprising galactoside beta-1,3-N-acetylglucosaminyltransferase and beta-1,6-N-acetylglucosaminyltransferase.

In an alternative and/or additional embodiment of the method and/or cell of this disclosure, the N-acetylgalactosaminyltransferase is chosen from the list comprising alpha-1,3-N-acetylgalactosaminyltransferase.

In a further embodiment of the method and/or cell of this disclosure, the cell is modified in the expression or activity of at least one of the glycosyltransferases. In a preferred embodiment, the glycosyltransferase is an endogenous protein of the cell with a modified expression or activity, preferably the endogenous glycosyltransferase is overexpressed; alternatively the glycosyltransferase is a heterologous protein that is heterogeneously introduced and expressed in the cell, preferably overexpressed. The endogenous glycosyltransferase can have a modified expression in the cell that also expresses a heterologous glycosyltransferase.

According to another and/or alternative preferred embodiment of the method and/or cell of this disclosure, the cell comprises a fucosylation pathway comprising at least one enzyme chosen from the list comprising mannose-6-phosphate isomerase, phosphomannomutase, mannose-1-phosphate guanylyltransferase, GDP-mannose 4,6-dehydratase, GDP-L-fucose synthase, fucose permease, fucose kinase, fucose-1-phosphate guanylyltransferase, fucosyltransferase.

According to another and/or alternative preferred embodiment of the method and/or cell of this disclosure, the cell comprises a galactosylation pathway comprising at least one enzyme chosen from the list comprising galactose-1-epimerase, galactokinase, glucokinase, galactose-1-phosphate uridylyltransferase, UDP-glucose 4-epimerase, glucose-1-phosphate uridylyltransferase, phosphoglucomutase, galactosyltransferase.

According to another and/or alternative preferred embodiment of the method and/or cell of this disclosure, the cell comprises an N-acetylglucosaminylation pathway comprising at least one enzyme chosen from the list comprising L-glutamine-D-fructose-6-phosphate aminotransferase, N-acetylglucosamine-6-phosphate deacetylase, phosphoglucosamine mutase, N-acetylglucosamine-1-phosphate uridylyltransferase/glucosamine-1-phosphate acetyltransferase, N-acetylglucosaminyltransferase.

In an alternative and/or additional further embodiment of the method and/or cell of this disclosure, the cell is modified in the expression or activity of at least one pyruvate dehydrogenase like e.g., from *E. coli, S. cerevisiae, H. sapiens* and *R norvegicus*. In a preferred embodiment, the cell has been modified to have at least one partially or fully knocked out or mutated pyruvate dehydrogenase encoding gene by means generally known by the person skilled in the art resulting in at least one protein with less functional or being disabled for pyruvate dehydrogenase activity. In a more preferred embodiment, the cell has a full knock-out in the poxB encoding gene resulting in a cell lacking pyruvate dehydrogenase activity.

In an alternative and/or additional further embodiment of the method and/or cell of this disclosure, the cell is modified in the expression or activity of at least one lactate dehydrogenase like e.g., from *E. coli, S. cerevisiae, H. sapiens* and *R norvegicus*. In a preferred embodiment, the cell has been modified to have at least one partially or fully knocked out or mutated lactate dehydrogenase encoding gene by means generally known by the person skilled in the art resulting in at least one protein with less functional or being disabled for lactate dehydrogenase activity. In a more preferred embodiment, the cell has a full knock-out in the ldhA encoding gene resulting in a cell lacking lactate dehydrogenase activity.

According to another preferred embodiment of the method and/or cell of this disclosure, the cell comprises a lower or reduced expression and/or abolished, impaired, reduced or delayed activity of any one or more of the proteins comprising beta-galactosidase, galactoside O-acetyltransferase, N-acetylglucosamine-6-phosphate deacetylase, glucosamine-6-phosphate deaminase, N-acetylglucosamine repressor, ribonucleotide monophosphatase, EIICBA-Nag, UDP-glucose:undecaprenyl-phosphateglucose-1-phosphatetransferase, L-fuculokinase, L-fucose isomerase, N-acetylneuraminate lyase, N-acetylmannosamine kinase, N-acetylmannosamine-6-phosphate 2-epimerase, EIIAB-Man, EIIC-Man, EIID-Man, ushA, galactose-1-phosphate uridylyltransferase, glucose-1-phosphate adenylyltransferase, glucose-1-phosphatase, ATP-dependent 6-phosphofructokinase isozyme 1, ATP-dependent 6-phosphofructokinase isozyme 2, glucose-6-phosphate isomerase, aerobic respiration control protein, transcriptional repressor IclR, ion protease, glucose-specific translocating phosphotransferase enzyme IIBC component ptsG, glucose-specific translocating phosphotransferase (PTS) enzyme IIBC component maX, enzyme $IIA^{Glc}$, beta-glucoside specific PTS enzyme II, fructose-specific PTS multiphosphoryl transfer protein FruA and FruB, ethanol dehydrogenase aldehyde dehydrogenase, pyruvate-formate lyase, acetate kinase, phosphoacyltransferase, phosphate acetyltransferase, pyruvate decarboxylase.

According to another preferred embodiment of the method and/or cell of this disclosure, the cell is using a precursor for the synthesis of a sialylated oligosaccharide, preferably a 3'sialylated oligosaccharide, more preferably 3'SL and/or 3'KDO-lactose. Herein, the precursor is fed to the cell from the cultivation or incubation medium. In another preferred embodiment, the cell is producing a precursor for the synthesis of the sialylated oligosaccharide, preferably 3'sialylated oligosaccharide.

In a preferred embodiment of the method and/or cell hereof, the method results in the production of 45 g/L or more, preferably 50 g/L or more, more preferably 60 g/L or more, of a 3'sialylated oligosaccharide. In a more preferred embodiment, the method results in the production of 45 g/L or more, preferably 50 g/L or more, more preferably 60 g/L or more of 3'SL.

In another more preferred embodiment, the method results in the production of 45 g/L or more, preferably 50 g/L or more, more preferably 60 g/L or more of a saccharide modified with KDO, preferably 3'KDO-lactose.

In an alternative preferred embodiment of the method and/or cell hereof, the method results in the production of 10 g/L or less, preferably 5 g/L or less, more preferably 1 g/L or less, even more preferably 0.5 g/L or less, even more preferably 0.4 g/L or less, even more preferably 0.3 g/L or less, even more preferably 0.2 g/L or less, most preferably 0.1 g/L or less of a saccharide modified with KDO, preferably 3'-KDO-lactose.

In another preferred embodiment of the method and/or cell hereof, the method results in the production of a saccharide mixture comprising a saccharide modified with KDO and another saccharide wherein the other saccharide is a 3'sialylated oligosaccharide different from KDO-lactose, preferably different from 3'KDO-lactose, preferably the other saccharide is 3'SL.

In another preferred embodiment of the method and/or cell hereof, the method results in the production of a saccharide mixture comprising a saccharide modified with KDO and another saccharide wherein the other saccharide is a 3'sialylated oligosaccharide not comprising any KDO-moiety.

In another and/or additional preferred embodiment of the method and/or cell hereof, the method results in the production of a saccharide mixture wherein the saccharide mixture comprises 45 g/L or more, preferably 50 g/L or more, more preferably 60 g/L or more, of a 3'sialylated oligosaccharide wherein the 3'sialylated oligosaccharide is not KDO-lactose, preferably not 3'KDO-lactose, and 10 g/L or less, preferably 5 g/L or less, more preferably 1 g/L or less, even more preferably 0.5 g/L or less, even more preferably 0.4 g/L or less, even more preferably 0.3 g/L or less, even more preferably 0.2 g/L or less, most preferably 0.1 g/L or less of a saccharide modified with KDO, preferably KDO-lactose, more preferably 3'-KDO-lactose. In a more preferred embodiment, the method results in the production of a saccharide mixture wherein the saccharide mixture comprises 45 g/L or more, preferably 50 g/L or more, more preferably 60 g/L or more, of 3'SL and 10 g/L or less, preferably 5 g/L or less, more preferably 1 g/L or less, even more preferably 0.5 g/L or less, even more preferably 0.4 g/L or less, even more preferably 0.3 g/L or less, even more preferably 0.2 g/L or less, most preferably 0.1 g/L or less of 3'KDO-lactose.

According to another preferred embodiment of the method and/or cell of this disclosure, the cell produces 90 g/L or more of a sialylated oligosaccharide, preferably a 3'sialylated oligosaccharide, more preferably 3'SL or 3'KDO-lactose, in the whole broth and/or supernatant. In a more preferred embodiment, a sialylated oligosaccharide, preferably a 3'sialylated oligosaccharide, more preferably 3'SL or 3'KDO-lactose, produced in the whole broth and/or supernatant has a purity of at least 80% measured on the total amount of the sialylated oligosaccharide, preferably a 3'sialylated oligosaccharide, more preferably 3'SL or 3'KDO-lactose, and its precursor produced by the cell in the whole broth and/or supernatant, respectively.

According to another preferred embodiment of the method and/or cell of this disclosure, the method results in the production of a sialylated oligosaccharide, preferably a 3'sialylated oligosaccharide, more preferably 3'SL or 3'KDO-lactose, with a purity equal to or greater than 80% measured on the total amount of the sialylated oligosaccharide, preferably a 3'sialylated oligosaccharide, more preferably 3'SL or 3'KDO-lactose, and its precursor. In a more preferred embodiment, the method results in the production of a sialylated oligosaccharide, preferably a 3'sialylated oligosaccharide, more preferably 3'SL or 3'KDO-lactose, with a purity equal to or greater than 85% measured on the total amount of the sialylated oligosaccharide, preferably a 3'sialylated oligosaccharide, more preferably 3'SL or 3'KDO-lactose, and its precursor. In an even more preferred embodiment, the method results in the production of a sialylated oligosaccharide, preferably a 3'sialylated oligosaccharide, more preferably 3'SL or 3'KDO-lactose, with a purity equal to or greater than 90% measured on the total amount of the sialylated oligosaccharide, preferably a 3'sialylated oligosaccharide, more preferably 3'SL or 3'KDO-lactose, and its precursor. In another even more preferred embodiment, the method results in the production of a sialylated oligosaccharide, preferably a 3'sialylated oligosaccharide, more preferably 3'SL or 3'KDO-lactose, with a purity equal to or greater than 91%, equal to or greater than 92%, equal to or greater than 93%, equal to or greater than 94%, equal to or greater than 95%, equal to or greater than 96%, equal to or greater than 97%, equal to or greater than 98%, equal to or greater than 99% measured on the total amount of the sialylated oligosaccharide, preferably a 3'sialylated oligosaccharide, more preferably 3'SL or 3'KDO-lactose, and its precursor.

According to another preferred embodiment of the method and/or cell of this disclosure, the method results in the production of a mixture comprising a sialylated oligosaccharide, preferably a 3'sialylated oligosaccharide, more preferably 3'SL, together with lactose and sialic acid, wherein the sialylated oligosaccharide, preferably a 3'sialylated oligosaccharide, more preferably 3'SL, has a purity equal to or greater than 80% measured on the total amount of the sialylated oligosaccharide, preferably a 3'sialylated oligosaccharide, more preferably 3'SL, lactose and sialic acid in the mixture and wherein the mixture comprises less than 10% lactose and/or less than 5% sialic acid. In a more preferred embodiment, the mixture comprises less than 9% lactose. In an even more preferred embodiment, the mixture comprises less than 8% lactose. In another even more preferred embodiment, the mixture comprises less than 7%, less than 6%, less than 5%, less than 4%, less than 3%, less than 2%, less than 1% lactose. In an additional and/or alternative more preferred embodiment, the mixture comprises less than 5% sialic acid. In an even more preferred additional and/or alternative embodiment, the mixture comprises less than 4%, less than 3%, less than 2%, less than 1%, less than 0.5%, less than 0.1% sialic acid.

According to another preferred embodiment of the method and/or cell of this disclosure, the method results in the production of a mixture comprising a sialylated oligosaccharide, preferably a 3'sialylated oligosaccharide, more preferably 3'KDO-lactose, together with lactose and sialic acid, wherein the sialylated oligosaccharide, preferably a 3'sialylated oligosaccharide, more preferably 3'KDO-lactose, has a purity equal to or greater than 80% measured on the total amount of the sialylated oligosaccharide, preferably a 3'sialylated oligosaccharide, more preferably 3'KDO-lactose, lactose and sialic acid in the mixture and wherein the mixture comprises less than 10% lactose and/or less than 5% sialic acid. In a more preferred embodiment, the mixture comprises less than 9% lactose. In an even more preferred embodiment, the mixture comprises less than 8% lactose. In another even more preferred embodiment, the mixture comprises less than 7%, less than 6%, less than 5%, less than 4%, less than 3%, less than 2%, less than 1% lactose. In an additional and/or alternative more preferred embodiment, the mixture comprises less than 5% sialic acid. In an even more preferred additional and/or alternative embodiment, the mixture comprises less than 4%, less than 3%, less than 2%, less than 1%, less than 0.5%, less than 0.1% sialic acid.

According to another preferred embodiment of the method and/or cell of this disclosure, the method results in the production of a mixture comprising 3'SL and 3'KDO-lactose, together with lactose and sialic acid, wherein the mixture comprises less than 10% lactose and/or less than 5% sialic acid. In a more preferred embodiment, the mixture comprises less than 9% lactose. In an even more preferred embodiment, the mixture comprises less than 8% lactose. In another even more preferred embodiment, the mixture comprises less than 7%, less than 6%, less than 5%, less than 4%, less than 3%, less than 2%, less than 1% lactose. In an additional and/or alternative more preferred embodiment, the mixture comprises less than 5% sialic acid. In an even more preferred additional and/or alternative embodiment, the mixture comprises less than 4%, less than 3%, less than 2%, less than 1%, less than 0.5%, less than 0.1% sialic acid.

According to another embodiment of the method and/or cell of this disclosure, the sialylated oligosaccharide is chosen from the list comprising a milk oligosaccharide, O-antigen, the oligosaccharide repeats present in capsular polysaccharides, an oligosaccharide present in lipopolysaccharides and amino-sugars. In a more preferred embodiment, the milk oligosaccharide is a mammalian milk oligosaccharide. In an even more preferred embodiment, the milk oligosaccharide is a human milk oligosaccharide.

According to another embodiment of the method and/or cell of this disclosure, the cell is capable of synthesizing a mixture of oligosaccharides. In an alternative and/or additional embodiment, the cell is capable of synthesizing a mixture of di- and oligosaccharides, alternatively, the cell is capable of synthesizing a mixture of sialic acid, di- and/or oligosaccharides.

Another aspect of this disclosure provides for a method and a cell wherein a sialylated oligosaccharide, preferably a 3'sialylated oligosaccharide, more preferably 3'SL and/or 3'KDO-lactose, is produced in and/or by a cell that is a bacterium, fungus, yeast, a plant cell, an animal cell, or a protozoan cell. The latter bacterium preferably belongs to the phylum of the Proteobacteria or the phylum of the Firmicutes or the phylum of the Cyanobacteria or the phylum Deinococcus-*Thermus* or the phylum of Actinobacteria. The latter bacterium belonging to the phylum Proteobacteria belongs preferably to the family Enterobacteriaceae, preferably to the species *E. coli*. The latter bacterium preferably relates to any strain belonging to the species *E. coli* such as but not limited to *E. coli* B, *E. coli* C, *E. coli* W, *E. coli* K12, *E. coli* Nissle. More specifically, the latter term relates to cultivated *Escherichia coli* strains—designated as *E. coli* K12 strains—which are well-adapted to the laboratory environment, and, unlike wild type strains, have lost their ability to thrive in the intestine. Well-known examples of the *E. coli* K12 strains are K12 Wild type, W3110, MG1655, M182, MC1000, MC1060, MC1061, MC4100, JM101, NZN111 and AA200. Hence, this disclosure specifically relates to a mutated and/or transformed *E. coli* cell or strain as indicated above wherein the *E. coli* strain is a K12 strain. More preferably, the *E. coli* K12 strain is *E. coli* MG1655. The latter bacterium belonging to the phylum Firmicutes belongs preferably to the Bacilli, preferably Lactobacilliales, with members such as *Lactobacillus lactis, Leuconostoc mesenteroides*, or Bacillales with members such as from the genus *Bacillus*, such as *Bacillus subtilis* or, *B. amyloliquefaciens*. The latter Bacterium belonging to the phylum Actinobacteria, preferably belonging to the family of the Corynebacteriaceae, with members *Corynebacterium glutamicum* or *C. afermentans*, or belonging to the family of the Streptomycetaceae with members *Streptomyces griseus* or *S. fradiae*. The latter bacterium belonging to the phylum Proteobacteria, preferably belonging to the family of the Vibrionaceae, with member *Vibrio natriegens*. The latter yeast preferably belongs to the phylum of the Ascomycota or the phylum of the Basidiomycota or the phylum of the Deuteromycota or the phylum of the Zygomycetes. The latter yeast belongs preferably to the genus *Saccharomyces* (with members like e.g., *Saccharomyces cerevisiae, S. bayanus, S. boulardii*), *Zygosaccharomyces, Pichia* (with members like e.g., *Pichia pastoris, P. anomala, P. kluyveri*), *Komagataella, Hansenula, Kluyveromyces* (with members like e.g., *Kluyveromyces lactis, K. marxianus, K. thermotolerans*), *Debaromyces, Candida, Schizosaccharomyces, Schwanniomyces, Torulaspora, Yarrowia* (like e.g., *Yarrowia lipolytica*) or *Starmerella* (like e.g., *Starmerella bombicola*). The latter yeast is preferably selected from *Pichia*

*pastoris, Yarrowia lipolytica, Saccharomyces cerevisiae, Kluyveromyces lactis, Hansenula polymorpha, Kluyveromyces marxianus, Pichia methanolica, Pichia stipites, Candida boidini, Schizosaccharomyces pombe, Schwanniomyces occidentalis, Torulaspora delbrueckii, Zygosaccharomyces rouxii,* and *Zygosaccharomyces bailii*. The latter fungus belongs preferably to the genus *Rhizopus, Dictyostelium, Penicillium, Mucor* or *Aspergillus*. Plant cells include cells of flowering and non-flowering plants, as well as algal cells, for example, *Chlamydomonas, Chlorella,* etc. Preferably, the plant is a tobacco, alfalfa, rice, tomato, cotton, rapeseed, soy, maize, or corn plant. The latter animal cell is preferably derived from non-human mammals (e.g., cattle, buffalo, pig, sheep, mouse, rat, primate (e.g., chimpanzee, orangutan, gorilla, monkey (e.g., Old World, New World), lemur), dog, cat, rabbit, horse, cow, goat, ox, deer, musk deer, bovid, whale, dolphin, hippopotamus, elephant, rhinoceros, giraffe, zebra, lion, cheetah, tiger, panda, red panda, otter), birds (e.g., chicken, duck, ostrich, turkey, pheasant), fish (e.g., swordfish, salmon, tuna, sea bass, trout, catfish), invertebrates (e.g., lobster, crab, shrimp, clams, oyster, mussel, sea urchin), reptiles (e.g., snake, alligator, turtle), amphibians (e.g., frogs) or insects (e.g., fly, nematode) or is a genetically engineered cell line derived from human cells excluding embryonic stem cells. Both human and non-human mammalian cells are preferably chosen from the list comprising an epithelial cell like e.g., a mammary epithelial cell, an embryonic kidney cell (e.g., HEK293 or HEK 293T cell), a fibroblast cell, a COS cell, a Chinese hamster ovary (CHO) cell, a murine myeloma cell like e.g., an N20, SP2/0 or YB2/0 cell, an NIH-3T3 cell, a non-mammary adult stem cell or derivatives thereof such as described in WO21067641, a lactocyte derived from mammalian induced pluripotent stem cells, preferably human induced pluripotent stem cells, a lactocyte as part of mammary-like gland organoids, a post-parturition mammary epithelium cell, a polarized mammary cell, preferably a polarized mammary cell selected from the group comprising live primary mammary epithelial cells, live mammary myoepithelial cells, live mammary progenitor cells, live immortalized mammary epithelial cells, live immortalized mammary myoepithelial cells, live immortalized mammary progenitor cells, a non-mammary adult stem cell or derivatives thereof as well-known to the person skilled in the art from e.g., WO2021/219634, WO 2022/054053, WO 2021/141762, WO 2021/142241, WO 2021/067641 and WO2021/242866. The latter insect cell is preferably derived from *Spodoptera frugiperda* like e.g., Sf9 or Sf21 cells, *Bombyx mori, Mamestra brassicae, Trichoplusia ni* like e.g., BTI-TN-5B1-4 cells or *Drosophila melanogaster* like e.g., *Drosophila* S2 cells. The latter protozoan cell preferably is a *Leishmania tarentolae* cell.

More preferably, the cell is selected from the group consisting of prokaryotic cells and eukaryotic cells, preferably from the group consisting of yeast cells, bacterial cells, archaebacterial cells, algae cells, and fungal cells as described herein.

According to another embodiment of the method and/or cell of this disclosure, the cell as described herein comprises a nucleic acid molecule comprising a polynucleotide sequence encoding a sialyltransferase as described herein and operably linked to control sequences recognized by the cell, wherein the sequence is foreign to the cell, the sequence further i) being integrated in the genome of the cell and/or ii) presented to the cell on a vector.

According to another preferred embodiment of the method and/or cell of this disclosure, the cell comprises a catabolic pathway for selected mono-, di- or oligosaccharides that is at least partially inactivated, the mono-, di-, or oligosaccharides being involved in and/or required for the synthesis of a sialylated oligosaccharide. Preferably, the sialylated oligosaccharide is a 3'sialylated oligosaccharide, more preferably 3'SL and/or 3'KDO-lactose.

A further aspect of this disclosure provides for an isolated nucleic acid molecule encoding a sialyltransferase encoding a sialyltransferase wherein the sialyltransferase has alpha-2,3-sialyltransferase activity on the galactose (Gal) residue of lactose and comprises an amino acid sequence that is i) at least 67.0% identical over a stretch of at least 150 amino acid residues, preferably at least 200 amino acid residues, to any one of the amino acid sequences as represented by SEQ ID NOs:5, 1, 2, 3, 6, 7, or 8, ii) at least 85.0% identical over a stretch of at least 150 amino acid residues, preferably at least 200 amino acid residues, to the amino acid sequence as represented by SEQ ID NO:4, or iii) at least 60.0% identical over a stretch of at least 150 amino acid residues, preferably at least 200 amino acid residues, to the amino acid sequence as represented by SEQ ID NO:12.

In a preferred embodiment, the sialyltransferase encoded by the isolated nucleic acid molecule comprises an amino acid sequence that is at least 67.0%, at least 70.0%, at least 75.0%, at least 80.0%, at least 85.0%, at least 90.0%, at least 95.0%, at least 96.0%, at least 97.0%, at least 98.0%, at least 98.5%, or at least 99.0% identical to any one of the amino acid sequences as represented by SEQ ID NOs:5, 1, 2, 3, 6, 7, or 8 over a stretch of at least 150, at least 160, at least 170, at least 180, at least 190, at least 200, at least 210, at least 220, at least 230, at least 240, at least 250, at least 260, at least 270, at least 280, at least 290 or at least 300 amino acid residues.

In another preferred embodiment, the sialyltransferase encoded by the isolated nucleic acid molecule comprises an amino acid sequence that is at least 55.0%, at least 60.0%, at least 65.0%, at least 70.0%, at least 75.0%, at least 80.0%, at least 85.0%, at least 90.0%, at least 95.0%, at least 96.0%, at least 97.0%, at least 98.0%, at least 98.5%, or at least 99.0% identical to any one of the full-length amino acid sequences as represented by SEQ ID NOs:05, 01, 02, 03, 06, 07 or 08.

In another preferred embodiment, the sialyltransferase encoded by the isolated nucleic acid molecule comprises an amino acid sequence that is at least 85.0%, at least 90.0%, at least 95.0%, at least 96.0%, at least 97.0%, at least 98.0%, at least 98.5%, or at least 99.0% identical to the amino acid sequence as represented by SEQ ID NO:04 over a stretch of at least 150, at least 160, at least 170, at least 180, at least 190, at least 200, at least 210, at least 220, at least 230, at least 240, at least 250, at least 260, at least 270, at least 280, at least 290 or at least 300 amino acid residues.

In another preferred embodiment, the sialyltransferase encoded by the isolated nucleic acid molecule comprises an amino acid sequence that is at least 80.0%, at least 85.0%, at least 90.0%, at least 95.0%, at least 96.0%, at least 97.0%, at least 98.0%, at least 98.5%, or at least 99.0% identical to the full-length amino acid sequence as represented by SEQ ID NO:04.

In another preferred embodiment, the sialyltransferase encoded by the isolated nucleic acid molecule comprises an amino acid sequence that is at least 60.0%, at least 65.0%, at least 70.0%, at least 75.0%, at least 80.0%, at least 85.0%, at least 90.0%, at least 95.0%, at least 96.0%, at least 97.0%, at least 98.0%, at least 98.5%, or at least 99.0% identical to the amino acid sequence as represented by SEQ ID NO:12 over a stretch of at least 150, at least 160, at least 170, at least 180, at least 190, at least 200, at least 210, at least 220, at least 230, at least 240, at least 250, at least 260, at least 270, at least 280, at least 290 or at least 300 amino acid residues.

In another preferred embodiment, the sialyltransferase encoded by the isolated nucleic acid molecule comprises an amino acid sequence that is at least 45.0%, at least 50.0%, at least 55.0%, at least 60.0%, at least 65.0%, at least 70.0%, at least 75.0%, at least 80.0%, at least 85.0%, at least 90.0%, at least 95.0%, at least 96.0%, at least 97.0%, at least 98.0%, at least 98.5%, or at least 99.0% identical to the full-length amino acid sequence as represented by SEQ ID NO:12.

In another preferred embodiment, the sialyltransferase encoded by the isolated nucleic acid molecule comprises an amino acid sequence as represented by any one of SEQ ID NOs:5, 4, 12, 1, 2, 3, 6, 7 or 8.

Another further aspect of this disclosure provides for an isolated nucleic acid molecule encoding a sialyltransferase wherein the sialyltransferase has alpha-2,3-sialyltransferase activity on the galactose (Gal) residue of lactose and comprises an amino acid sequence that is at least 80.0% identical to any one of the full-length amino acid sequences as represented by SEQ ID NOs:5, 4, 12, 1, 2, 3, 6, 7, or 8.

In a preferred embodiment, the sialyltransferase encoded by the isolated nucleic acid molecule comprises an amino acid sequence that is at least 80.0%, at least 85.0%, at least 90.0%, at least 95.0%, at least 96.0%, at least 97.0%, at least 98.0%, at least 98.5%, or at least 99.0% identical to any one of the full-length amino acid sequences as represented by SEQ ID NOs:5, 4, 12, 1, 2, 3, 6, 7, or 8.

In another preferred embodiment, the sialyltransferase encoded by the isolated nucleic acid molecule comprises an amino acid sequence as represented by any one of SEQ ID NOs:5, 4, 12, 1, 2, 3, 6, 7, or 8.

Another aspect of this disclosure provides for a vector comprising an isolated nucleic acid molecule encoding a sialyltransferase as described herein.

Another aspect provides for a cell to be stably cultured in a medium, wherein the medium can be any type of growth medium comprising minimal medium, complex medium or growth medium enriched in certain compounds like, for example, but not limited to, vitamins, trace elements, amino acids.

The microorganism or cell as used herein is capable of growing on a monosaccharide, disaccharide, oligosaccharide, polysaccharide, polyol, glycerol, a complex medium or a mixture thereof as the main carbon source. With the term main is meant the most important carbon source for the microorganism or cell for the production of the sialylated oligosaccharide of interest, biomass formation, carbon dioxide and/or by-products formation (such as acids and/or alcohols, such as acetate, lactate, and/or ethanol), i.e., 20, 30, 40, 50, 60, 70, 75, 80, 85, 90, 95, 98, 99% of all the required carbon is derived from the above-indicated carbon source. In one embodiment of this disclosure, the carbon source is the sole carbon source for the organism, i.e., 100% of all the required carbon is derived from the above-indicated carbon source. Common main carbon sources comprise but are not limited to glucose, glycerol, fructose, sucrose, maltose, lactose, arabinose, malto-oligosaccharides, maltotriose, sorbitol, xylose, rhamnose, galactose, mannose, methanol, ethanol, trehalose, starch, cellulose, hemi-cellulose, molasses, corn-steep liquor, high-fructose syrup, acetate, citrate, lactate and pyruvate. As used herein, a precursor as defined herein cannot be used as a carbon source for the production of the sialylated oligosaccharide, preferably 3'sialylated oligosaccharide, hereof.

According to this disclosure, the methods as described herein preferably comprises a step of separating the sialylated oligosaccharide, preferably 3'sialylated oligosaccharide, hereof from the cultivation or incubation, otherwise the recovering the sialylated oligosaccharide, preferably 3'sialylated oligosaccharide, from the cultivation or incubation medium and/or the cell.

The terms "separating from the cultivation or incubation" means harvesting, collecting, or retrieving the sialylated oligosaccharide, preferably 3'sialylated oligosaccharide, from the cell and/or the medium of its cultivation or incubation.

The sialylated oligosaccharide, preferably 3'sialylated oligosaccharide, can be separated in a conventional manner from the aqueous culture medium, in which the cell was cultivated or incubated. In case the sialylated oligosaccharide, preferably 3'sialylated oligosaccharide, is still present in the cells producing the sialylated oligosaccharide, preferably 3'sialylated oligosaccharide, conventional manners to free or to extract the sialylated oligosaccharide, preferably 3'sialylated oligosaccharide, out of the cells can be used, such as cell destruction using high pH, heat shock, sonication, French press, homogenization, enzymatic hydrolysis, chemical hydrolysis, solvent hydrolysis, detergent, hydrolysis, etc. The cultivation or incubation medium and/or cell extract together and separately can then be further used for separating the sialylated oligosaccharide, preferably 3'sialylated oligosaccharide.

This preferably involves clarifying the sialylated oligosaccharide, preferably 3'sialylated oligosaccharide, to remove suspended particulates and contaminants, particularly cells, cell components, insoluble metabolites and debris produced by culturing or incubating the genetically engineered cell. In this step, the sialylated oligosaccharide, preferably 3'sialylated oligosaccharide, can be clarified in a conventional manner. Preferably, the sialylated oligosaccharide, preferably 3'sialylated oligosaccharide, is clarified by centrifugation, flocculation, decantation and/or filtration. Another step of separating the sialylated oligosaccharide, preferably 3'sialylated oligosaccharide, preferably involves removing substantially all the eventually remaining proteins, peptides, amino acids, RNA and DNA, and any endotoxins and glycolipids that could interfere with the subsequent separation step, from the sialylated oligosaccharide, preferably 3'sialylated oligosaccharide, preferably after it has been clarified. In this step, remaining proteins and related impurities can be removed from the sialylated oligosaccharide, preferably 3'sialylated oligosaccharide, in a conventional manner. Preferably, remaining proteins, salts, by-products, color, endotoxins and other related impurities are removed from the sialylated oligosaccharide, preferably 3'sialylated oligosaccharide, by ultrafiltration, nanofiltration, two-phase partitioning, reverse osmosis, microfiltration, activated charcoal or carbon treatment, treatment with non-ionic surfactants, enzymatic digestion, tangential flow high-performance filtration, tangential flow ultrafiltration, electrophoresis (e.g., using slab-polyacrylamide or sodium dodecyl sulphate-polyacrylamide gel electrophoresis (PAGE)), affinity chromatography (using affinity ligands including e.g., DEAE-Sepharose, poly-L-lysine and polymyxin-B, endotoxin-selective adsorber matrices), ion exchange chromatography (such as but not limited to cation exchange, anion exchange, mixed bed ion exchange, inside-out ligand attachment), hydrophobic interaction chromatography and/or gel filtration (i.e., size exclusion chromatography), particularly by chromatography, more particularly by ion exchange chromatography or hydrophobic interaction chromatography or ligand exchange chromatography or electrodialysis. With the exception of size exclusion chromatography, remaining proteins and related impurities are retained by a chromatography medium or a selected membrane.

In a further preferred embodiment, the methods as described herein also provide for a further purification of the sialylated oligosaccharide, preferably 3'sialylated oligosaccharide, hereof. A further purification of the sialylated oligosaccharide, preferably 3'sialylated oligosaccharide, may be accomplished, for example, by use of (activated) charcoal or carbon, nanofiltration, ultrafiltration, electrophoresis, enzymatic treatment or ion exchange, temperature adjustment, pH adjustment or pH adjustment with an alkaline or acidic solution to remove any remaining DNA, protein, LPS, endotoxins, or other impurity. Alcohols, such as ethanol, and aqueous alcohol mixtures can also be used. Another purification step is accomplished by crystallization, evaporation or precipitation of the sialylated oligosaccharide, preferably 3'sialylated oligosaccharide. Another purification step is to dry, e.g., spray dry, lyophilize, spray freeze dry, freeze spray dry, band dry, belt dry, vacuum band dry, vacuum belt dry, drum dry, roller dry, vacuum drum dry or vacuum roller dry the produced sialylated oligosaccharide, preferably 3'sialylated oligosaccharide.

In an exemplary embodiment, the separation and purification of the sialylated oligosaccharide, preferably 3'sialylated oligosaccharide, is made in a process, comprising the following steps in any order:
a) contacting the cultivation or incubation or a clarified version thereof with a nanofiltration membrane with a molecular weight cut-off (MWCO) of 600-3500 Da ensuring the retention of the produced sialylated oligosaccharide, preferably 3'sialylated oligosaccharide, and allowing at least a part of the proteins, salts, by-products, color and other related impurities to pass,
b) conducting a diafiltration process on the retentate from step a), using the membrane, with an aqueous solution of an inorganic electrolyte, followed by optional diafiltration with pure water to remove excess of the electrolyte,
c) and collecting the retentate enriched in the sialylated oligosaccharide, preferably 3'sialylated oligosaccharide, in the form of a salt from the cation of the electrolyte.

In an alternative exemplary embodiment, the separation and purification of the sialylated oligosaccharide, preferably 3'sialylated oligosaccharide, is made in a process, comprising the following steps in any order: subjecting the cultivation or incubation or a clarified version thereof to two membrane filtration steps using different membranes, wherein
one membrane has a molecular weight cut-off of between about 300 to about 500 Dalton, and
the other membrane as a molecular weight cut-off of between about 600 to about 800 Dalton.

In an alternative exemplary embodiment, the separation and purification of the sialylated oligosaccharide, preferably 3'sialylated oligosaccharide, is made in a process, comprising treating the cultivation or incubation or a clarified version thereof with a strong cation exchange resin in H+-form in a step and with a weak anion exchange resin in free base form in another step, wherein the steps can be performed in any order.

In an alternative exemplary embodiment, the separation and purification of the sialylated oligosaccharide, preferably 3'sialylated oligosaccharide, is made in the following way.

The cultivation or incubation comprising the produced sialylated oligosaccharide, preferably 3'sialylated oligosaccharide, biomass, medium components and contaminants is applied to the following purification steps:
i) separation of biomass from the cultivation or incubation,
ii) cationic ion exchanger treatment for the removal of positively charged material,
iii) anionic ion exchanger treatment for the removal of negatively charged material,
iv) nanofiltration step and/or electrodialysis step,
wherein a purified solution comprising the produced sialylated oligosaccharide, preferably 3'sialylated oligosaccharide, at a purity of greater than or equal to 80% is provided. Optionally the purified solution is dried by any one or more drying steps chosen from the list comprising spray drying, lyophilization, spray freeze drying, freeze spray drying, band drying, belt drying, vacuum band drying, vacuum belt drying, drum drying, roller drying, vacuum drum drying and vacuum roller drying.

In an alternative exemplary embodiment, the separation and purification of the sialylated oligosaccharide, preferably 3'sialylated oligosaccharide, is made in a process, comprising the following steps in any order: enzymatic treatment of the cultivation or incubation; removal of the biomass from the cultivation or incubation; ultrafiltration; nanofiltration; and a column chromatography step. Preferably, such column chromatography is a single column or a multiple column. Further preferably, the column chromatography step is simulated moving bed chromatography. Such simulated moving bed chromatography preferably comprises i) at least 4 columns, wherein at least one column comprises a weak or strong cation exchange resin; and/or ii) four zones I, II, III and IV with different flow rates; and/or iii) an eluent comprising water; and/or iv) an operating temperature of 15 degrees to 60 degrees centigrade.

In a specific embodiment, this disclosure provides the produced sialylated oligosaccharide, preferably 3'sialylated oligosaccharide, which is dried to powder by any one or more drying steps chosen from the list comprising spray drying, lyophilization, spray freeze drying, freeze spray drying, band drying, belt drying, vacuum band drying, vacuum belt drying, drum drying, roller drying, vacuum drum drying and vacuum roller drying, wherein the dried powder contains <15%-wt. of water, preferably <10%-wt. of water, more preferably <7%-wt. of water, most preferably <5%-wt. of water.

Another aspect of this disclosure provides the use of a sialyltransferase that has alpha-2,3-sialyltransferase activity on the galactose (Gal) residue of lactose and that comprises an amino acid sequence:
that is at least 67.0%, at least 70.0%, at least 75.0%, at least 80.0%, at least 85.0%, at least 90.0%, at least 95.0%, at least 96.0%, at least 97.0%, at least 98.0%, at least 98.5%, or at least 99.0% identical to any one of the amino acid sequences as represented by SEQ ID NOs: 05, 01, 02, 03, 06, 07 or 08 over a stretch of at least 150, at least 160, at least 170, at least 180, at least 190, at least 200, at least 210, at least 220, at least 230, at least 240, at least 250, at least 260, at least 270, at least 280, at least 290 or at least 300 amino acid residues,
that is at least 55.0%, at least 60.0%, at least 65.0%, at least 70.0%, at least 75.0%, at least 80.0%, at least 85.0%, at least 90.0%, at least 95.0%, at least 96.0%, at least 97.0%, at least 98.0%, at least 98.5%, or at least 99.0% identical to any one of the full-length amino acid sequences as represented by SEQ ID NOs:5, 1, 2, 3, 6, 7, or 8, that is at least 85.0%, at least 90.0%, at least 95.0%, at least 96.0%, at least 97.0%, at least 98.0%, at least 98.5%, or at least 99.0% identical to the amino acid sequence as represented by SEQ ID NO:04 over a stretch of at least 150, at least 160, at least 170, at least 180, at least 190, at least 200, at least 210, at least 220, at least 230, at least 240, at least 250, at least 260, at least 270, at least 280, at least 290 or at least 300 amino acid residues, that is at least 80.0%, at least 85.0%, at least 90.0%, at least 95.0%, at least 96.0%, at least 97.0%, at least 98.0%, at least 98.5%, or at least 99.0% identical to the full-length amino acid sequence as represented by SEQ ID NO:4, that is at least 60.0%, at least 65.0%, at least 70.0%, at least 75.0%, at least 80.0%, at least 85.0%, at least 90.0%, at least 95.0%, at least 96.0%, at least 97.0%, at least 98.0%, at least 98.5%, or at least 99.0% identical to the amino acid sequence as represented by SEQ ID NO:12 over a stretch of at least 150, at least 160, at least 170, at least 180, at least 190, at least 200, at least 210, at least 220, at least 230, at least 240, at least 250, at least 260, at least 270, at least 280, at least 290 or at least 300 amino acid residues, that is at least 45.0%, at least 50.0%, at least 55.0%, at least 60.0%, at least 65.0%, at least 70.0%, at least 75.0%, at least 80.0%, at least 85.0%, at least 90.0%, at least 95.0%, at least 96.0%, at least 97.0%, at least 98.0%, at least 98.5%, or at least 99.0% identical to the full-length amino acid sequence as represented by SEQ ID NO:12, or as represented by any one of SEQ ID NOs:5, 4, 12, 1, 2, 3, 6, 7, or 8, for production of a sialylated oligosaccharide, preferably a 3'sialylated oligosaccharide, more preferably 3'SL.

Another aspect of this disclosure provides the use of a sialyltransferase that has alpha-2,3-sialyltransferase activity on the galactose (Gal) residue of lactose and that comprises an amino acid sequence:

that is at least 80.0%, at least 85.0%, at least 90.0%, at least 95.0%, at least 96.0%, at least 97.0%, at least 98.0%, at least 98.5%, or at least 99.0% identical to any one of the full-length amino acid sequences as represented by SEQ ID NOs:5, 4, 12, 1, 2, 3, 6, 7, or 8, or as represented by any one of SEQ ID NOs:5, 4, 12, 1, 2, 3, 6, 7, or 8, for production of a 3'sialylated oligosaccharide, preferably 3'SL or 3'KDO-lactose.

Another aspect of this disclosure provides the use of a cell as described herein for production of a sialylated oligosaccharide, preferably a 3'sialylated oligosaccharide, more preferably 3'SL and/or 3'KDO-lactose.

A further aspect of this disclosure provides i) use of a method as described herein for production of a sialylated oligosaccharide, preferably a 3'sialylated oligosaccharide, more preferably 3'SL and/or 3'KDO-lactose, ii) use of an isolated nucleic acid molecule as described herein for production of a sialylated oligosaccharide, preferably a 3'sialylated oligosaccharide, more preferably 3'SL and/or 3'KDO-lactose, or iii) use of a vector as described herein for production of a sialylated oligosaccharide, preferably a 3'sialylated oligosaccharide, more preferably 3'SL and/or 3'KDO-lactose.

Furthermore, the disclosure also relates to the sialylated oligosaccharide, preferably 3'sialylated oligosaccharide, obtained by the methods according to this disclosure. The sialylated oligosaccharide, preferably 3'sialylated oligosaccharide, may be used for the manufacture of a preparation, as food additive, prebiotic, symbiotic, for the supplementation of baby food, adult food, infant animal feed, adult animal feed, or as either therapeutically or pharmaceutically active compound or in cosmetic applications. In a preferred embodiment, the preparation comprises at least one sialylated oligosaccharide, preferably a 3'sialylated oligosaccharide, more preferably 3'SL and/or 3'KDO-lactose, that is obtainable, preferably obtained, by the methods as described herein. In another preferred embodiment, a preparation is provided that further comprises at least one probiotic microorganism. In another preferred embodiment, the preparation is a nutritional composition. In a more preferred embodiment, the preparation is a medicinal formulation, a dietary supplement, a dairy drink or an infant formula.

With the novel methods, the sialylated oligosaccharide, preferably 3'sialylated oligosaccharide, can easily and effectively be provided, without the need for complicated, time and cost consuming synthetic processes.

For identification of the sialylated oligosaccharide, preferably 3'sialylated oligosaccharide, hereof produced as described herein, the monosaccharide or the monomeric building blocks (e.g., the monosaccharide or glycan unit composition), the anomeric configuration of side chains, the presence and location of substituent groups, degree of polymerization/molecular weight and the linkage pattern can be identified by standard methods known in the art, such as, e.g., methylation analysis, reductive cleavage, hydrolysis, GC-MS (gas chromatography-mass spectrometry), MALDI-MS (Matrix-assisted laser desorptionfionization-mass spectrometry), ESI-MS (Electrospray ionization-mass spectrometry), HPLC (High-Performance Liquid chromatography with ultraviolet or refractive index detection), HPAEC-PAD (High-Performance Anion-Exchange chromatography with Pulsed Amperometric Detection), CE (capillary electrophoresis), IR (infrared)/Raman spectroscopy, and NMR (Nuclear magnetic resonance) spectroscopy techniques. The crystal structure can be solved using, e.g., solid-state NMR, FT-IR (Fourier transform infrared spectroscopy), and WAXS (wide-angle X-ray scattering). The degree of polymerization (DP), the DP distribution, and polydispersity can be determined by, e.g., viscosimetry and SEC (SEC-HPLC, high performance size-exclusion chromatography). To identify the monomeric components of the sialylated oligosaccharide, preferably 3'sialylated oligosaccharide, methods such as e.g., acid-catalyzed hydrolysis, HPLC (high performance liquid chromatography) or GLC (gas-liquid chromatography) (after conversion to alditol acetates) may be used. To determine the glycosidic linkages, the sialylated oligosaccharide, preferably 3'sialylated oligosaccharide, is methylated with methyl iodide and strong base in DMSO, hydrolysis is performed, a reduction to partially methylated alditols is achieved, an acetylation to methylated alditol acetates is performed, and the analysis is carried out by GLC/MS (gas-liquid chromatography coupled with mass spectrometry). To determine the glycan sequence, a partial depolymerization is carried out using an acid or enzymes to determine the structures. To identify the anomeric configuration, the sialylated oligosaccharide, preferably 3'sialylated oligosaccharide, is subjected to enzymatic analysis, e.g., it is contacted with an enzyme that is specific for a particular type of linkage, e.g., beta-galactosidase, or alpha-glucosidase, etc., and NMR may be used to analyze the products.

The separated and preferably also purified sialylated oligosaccharide, preferably 3'sialylated oligosaccharide, as described herein is incorporated into a food (e.g., human food or feed), dietary supplement, pharmaceutical ingredient, cosmetic ingredient or medicine. In some embodiments, the sialylated oligosaccharide, preferably 3'sialylated oligosaccharide, is mixed with one or more ingredients suitable for food, feed, dietary supplement, pharmaceutical ingredient, cosmetic ingredient or medicine.

In some embodiments, the dietary supplement comprises at least one prebiotic ingredient and/or at least one probiotic ingredient.

A "prebiotic" is a substance that promotes growth of microorganisms beneficial to the host, particularly microorganisms in the gastrointestinal tract. In some embodiments, a dietary supplement provides multiple prebiotics, including the 3'sialylated oligosaccharide being a prebiotic produced and/or purified by a process disclosed in this disclosure, to promote growth of one or more beneficial microorganisms. Examples of prebiotic ingredients for dietary supplements include other prebiotic molecules (such as HMOs) and plant polysaccharides (such as inulin, pectin, b-glucan and xylooligosaccharide). A "probiotic" product typically contains live microorganisms that replace or add to gastrointestinal microflora, to the benefit of the recipient. Examples of such microorganisms include *Lactobacillus* species (for example, *L. acidophilus* and *L. bulgaricus*), *Bifidobacterium* species (for example, *B. animalis*, *B. longum* and *B. infantis* (e.g., Bi-26)), and *Saccharomyces boulardii*. In some embodiments, a sialylated oligosaccharide, preferably 3'sialylated oligosaccharide, produced and/or purified by a process of this disclosure is orally administered in combination with such microorganism.

Examples of further ingredients for dietary supplements include oligosaccharides (such as 2'-fucosyllactose, 3-fucosyllactose, 6'-sialyllactose), disaccharides (such as lactose), monosaccharides (such as glucose, galactose, L-fucose, sialic acid, glucosamine and N-acetylglucosamine), thickeners (such as gum arabic), acidity regulators (such as trisodium citrate), water, skimmed milk, and flavorings.

In some embodiments, the sialylated oligosaccharide, preferably 3'sialylated oligosaccharide, is incorporated into a human baby food (e.g., infant formula). Infant formula is generally a manufactured food for feeding to infants as a complete or partial substitute for human breast milk. In some embodiments, infant formula is sold as a powder and prepared for bottle- or cup-feeding to an infant by mixing with water. The composition of infant formula is typically designed to be roughly mimic human breast milk. In some embodiments, a sialylated oligosaccharide, preferably 3'sialylated oligosaccharide, produced and/or purified by a process in this disclosure is included in infant formula to provide nutritional benefits similar to those provided by the oligosaccharides in human breast milk. In some embodiments, the sialylated oligosaccharide, preferably 3'sialylated oligosaccharide, is mixed with one or more ingredients of the infant formula. Examples of infant formula ingredients include non-fat milk, carbohydrate sources (e.g., lactose), protein sources (e.g., whey protein concentrate and casein), fat sources (e.g., vegetable oils—such as palm, high oleic safflower oil, rapeseed, coconut and/or sunflower oil; and fish oils), vitamins (such as vitamins A, Bb, Bi2, C and D), minerals (such as potassium citrate, calcium citrate, magnesium chloride, sodium chloride, sodium citrate and calcium phosphate) and possibly human milk oligosaccharides (HMOs). Such HMOs may include, for example, DiFL, lacto-N-triose II, LNT, LNnT, lacto-N-fucopentaose I, lacto-N-neofucopentaose, lacto-N-fucopentaose II, lacto-N-fucopentaose III, lacto-N-fucopentaose V, lacto-N-neofucopentaose V, lacto-N-difucohexaose I, lacto-N-difucohexaose II, 6'-galactosyllactose, 3'-galactosyllactose, lacto-N-hexaose and lacto-N-neohexaose.

In some embodiments, the one or more infant formula ingredients comprise non-fat milk, a carbohydrate source, a protein source, a fat source, and/or a vitamin and mineral.

In some embodiments, the one or more infant formula ingredients comprise lactose, whey protein concentrate and/or high oleic safflower oil.

In some embodiments, the concentration of the sialylated oligosaccharide, preferably 3'sialylated oligosaccharide, in the infant formula is approximately the same concentration as the concentration of the sialylated oligosaccharide, preferably 3'sialylated oligosaccharide, generally present in human breast milk.

In some embodiments, the sialylated oligosaccharide, preferably 3'sialylated oligosaccharide, is incorporated into a feed preparation, wherein the feed is chosen from the list comprising pet food, animal milk replacer, veterinary product, veterinary feed supplement, nutrition supplement, post weaning feed, or creep feed.

As will be shown in the examples herein, the methods and the cell of this disclosure preferably provide at least one of the following further surprising advantages when using a sialyltransferase as described herein:

Higher titers of the sialylated oligosaccharide, preferably 3'sialylated oligosaccharide (g/L), Higher purity of the sialylated oligosaccharide, preferably 3'sialylated oligosaccharide (g/L), A purity of the sialylated oligosaccharide, preferably 3'sialylated oligosaccharide, (g/L) equal to or greater than 80%, preferably equal to or greater than 85%, more preferably equal to or greater than 90%, even more preferably equal to or greater than 91%, even more preferably equal to or greater than 92%, even more preferably equal to or greater than 93%, even more preferably equal to or greater than 94%, even more preferably equal to or greater than 95%, even more preferably equal to or greater than 96%, even more preferably equal to or greater than 97%, even more preferably equal to or greater than 98%, even more preferably equal to or greater than 99%, Higher lactose conversion, leading to lower lactose concentration at end of fermentation (g/L lactose), Lower sialic acid formation (g/L), Higher production rate r (g sialylated oligosaccharide/L/h, preferably g 3'sialylated oligosaccharide/L/h), Higher cell performance index CPI (g sialylated oligosaccharide/g X, preferably g 3'sialylated oligosaccharide/g X), Higher specific productivity Qp (g sialylated oligosaccharide/g X/h, preferably g 3'sialylated oligosaccharide/g X/h), Higher yield on the carbon source used Y (g sialylated oligosaccharide/g carbon source used, preferably g 3'sialylated oligosaccharide/g carbon source used), Higher yield on sucrose Ys (g sialylated oligosaccharide/g sucrose, preferably g 3'sialylated oligosaccharide/g sucrose), Higher uptake/conversion rate of the carbon source used Q (g carbon source/g X/h), Higher sucrose uptake/conversion rate Qs (g sucrose/g X/h), Higher lactose conversion/consumption rate rs (g lactose/h), Higher secretion, excretion or extracellular transport of the sialylated oligosaccharide, preferably 3'sialylated oligosaccharide, and/or Higher growth speed of the production host, when compared to a method or a cell using an identical setup or enzymatic or genetic background but lacking the use of a sialyltransferase as described herein.

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry and nucleic acid chemistry and hybridization described above and below are those well-known and commonly employed in the art. Standard techniques are used for nucleic acid and peptide synthesis. Generally, purification steps are performed according to the manufacturer's specifications.

Further advantages follow from the specific embodiments and the examples. It goes without saying that the above-mentioned features and the features that are still to be explained below can be used not only in the respectively specified combinations, but also in other combinations or on their own, without departing from the scope of this disclosure.

Moreover, this disclosure relates to the following specific embodiments:

1. Method for the production of a sialylated oligosaccharide, preferably a 3'sialylated oligosaccharide, more preferably 3'SL (Neu5Ac-a2,3-Gal-b1,4-Glc), the method comprising: contacting a sialyltransferase with a mixture comprising a donor comprising a sialic acid residue, and an acceptor chosen from the list comprising an oligosaccharide or a disaccharide, under conditions wherein the sialyltransferase catalyzes the transfer of a sialic acid residue from the donor to the acceptor, thereby producing the sialylated oligosaccharide, preferably a 3'sialylated oligosaccharide, more preferably 3'SL, wherein the sialyltransferase has alpha-2,3-sialyltransferase activity on the galactose (Gal) residue of lactose and comprises an amino acid sequence that is:

at least 67.0% identical over a stretch of at least 150 amino acid residues, preferably at least 200 amino acid residues, to any one of the amino acid sequences as represented by SEQ ID NOs:05, 01, 02, 03, 06, 07 or 08, at least 85.0% identical over a stretch of at least 150 amino acid residues, preferably at least 200 amino acid residues, to the amino acid sequence as represented by SEQ ID NO:04, or at least 60.0% identical over a stretch of at least 150 amino acid residues, preferably at least 200 amino acid residues, to the amino acid sequence as represented by SEQ ID NO:12.

2. Method according to embodiment 1, wherein the sialylated oligosaccharide is 3'SL and the acceptor is lactose.

3. Method for the production of a sialylated oligosaccharide, preferably a 3'sialylated oligosaccharide, more preferably 3'SL (Neu5Ac-a2,3-Gal-b1,4-Glc), the method comprising the steps of:
a) providing
i. CMP-sialic acid,
ii. an acceptor, preferably lactose, and
iii. a sialyltransferase, wherein the sialyltransferase has alpha-2,3-sialyltransferase activity on the galactose (Gal) residue of lactose and comprises an amino acid sequence that is:
at least 67.0% identical over a stretch of at least 150 amino acid residues, preferably at least 200 amino acid residues, to any one of the amino acid sequences as represented by SEQ ID NOs:05, 01, 02, 03, 06, 07 or 08,
at least 85.0% identical over a stretch of at least 150 amino acid residues, preferably at least 200 amino acid residues, to the amino acid sequence as represented by SEQ ID NO:04, or
at least 60.0% identical over a stretch of at least 150 amino acid residues, preferably at least 200 amino acid residues, to the amino acid sequence as represented by SEQ ID NO:12,
b) contacting the sialyltransferase and CMP-sialic acid with the acceptor, preferably lactose, under conditions where the sialyltransferase catalyzes the transfer of a sialic acid residue from the CMP-sialic acid to the acceptor resulting in the production of a sialylated oligosaccharide, preferably a 3'sialylated oligosaccharide, more preferably 3'SL (Neu5Ac-a2,3-Gal-b1,4-Glc),
c) preferably, separating the produced sialylated oligosaccharide.

4. Method according to any one of previous embodiments, the method comprising: contacting a cell extract comprising the sialyltransferase with a mixture comprising a donor comprising a sialic acid residue, and an acceptor comprising an oligosaccharide or disaccharide, under conditions wherein the sialyltransferase catalyzes the transfer of a sialic acid residue from the donor to the acceptor, thereby producing the sialylated oligosaccharide, preferably a 3'sialylated oligosaccharide, more preferably 3'SL.

5. Method according to any one of previous embodiments, wherein the sialylated oligosaccharide, preferably a 3'sialylated oligosaccharide, more preferably 3'SL, is produced in a cell-free system.

6. Method for the production of a sialylated oligosaccharide, preferably a 3'sialylated oligosaccharide, more preferably 3'SL (Neu5Ac-a2,3-Gal-b1,4-Glc), the method comprising the steps of:
i. providing a cell, preferably a single cell, expressing, preferably heterologously expressing, more preferably overexpressing, even more preferably heterologously overexpressing, a sialyltransferase wherein the sialyltransferase has alpha-2,3-sialyltransferase activity on the galactose (Gal) residue of lactose and comprises an amino acid sequence that is:
at least 67.0% identical over a stretch of at least 150 amino acid residues, preferably at least 200 amino acid residues, to any one of the amino acid sequences as represented by SEQ ID NOs:05, 01, 02, 03, 06, 07 or 08,
at least 85.0% identical over a stretch of at least 150 amino acid residues, preferably at least 200 amino acid residues, to the amino acid sequence as represented by SEQ ID NO:04, or
at least 60.0% identical over a stretch of at least 150 amino acid residues, preferably at least 200 amino acid residues, to the amino acid sequence as represented by SEQ ID NO:12,
ii. providing CMP-sialic acid, optionally the CMP-sialic acid is produced by the cell, and
iii. providing an oligosaccharide or disaccharide, optionally the oligosaccharide or disaccharide is produced by the cell, and
iv. cultivating and/or incubating the cell under conditions permissive to express the sialyltransferase, optionally permissive to produce the CMP-sialic acid and/or the oligosaccharide or disaccharide,
v. preferably, separating the sialylated oligosaccharide, preferably 3'sialylated oligosaccharide, more preferably 3'SL, from the cultivation or incubation.

7. Method according to embodiment 6, wherein the cell is a metabolically engineered cell, preferably wherein the cell is metabolically engineered for the production of the sialylated oligosaccharide, preferably 3'sialylated oligosaccharide, more preferably 3'SL.

8. Method according to any one of previous embodiments, wherein the sialyltransferase comprises an amino acid sequence:
   that is at least 67.0%, at least 70.0%, at least 75.0%, at least 80.0%, at least 85.0%, at least 90.0%, at least 95.0%, at least 96.0%, at least 97.0%, at least 98.0%, at least 98.5%, or at least 99.0% identical to any one of the amino acid sequences as represented by SEQ ID NOs: 05, 01, 02, 03, 06, 07 or 08 over a stretch of at least 150, at least 160, at least 170, at least 180, at least 190, at least 200, at least 210, at least 220, at least 230, at least 240, at least 250, at least 260, at least 270, at least 280, at least 290 or at least 300 amino acid residues,
   that is at least 55.0%, at least 60.0%, at least 65.0%, at least 70.0%, at least 75.0%, at least 80.0%, at least 85.0%, at least 90.0%, at least 95.0%, at least 96.0%, at least 97.0%, at least 98.0%, at least 98.5%, or at least 99.0% identical to any one of the full-length amino acid sequences as represented by SEQ ID NOs: 05, 01, 02, 03, 06, 07 or 08,
   that is at least 85.0%, at least 90.0%, at least 95.0%, at least 96.0%, at least 97.0%, at least 98.0%, at least 98.5%, or at least 99.0% identical to the amino acid sequence as represented by SEQ ID NO:04 over a stretch of at least 150, at least 160, at least 170, at least 180, at least 190, at least 200, at least 210, at least 220, at least 230, at least 240, at least 250, at least 260, at least 270, at least 280, at least 290 or at least 300 amino acid residues,
   that is at least 80.0%, at least 85.0%, at least 90.0%, at least 95.0%, at least 96.0%, at least 97.0%, at least 98.0%, at least 98.5%, or at least 99.0% identical to the full-length amino acid sequence as represented by SEQ ID NO:04,
   that is at least 60.0%, at least 65.0%, at least 70.0%, at least 75.0%, at least 80.0%, at least 85.0%, at least 90.0%, at least 95.0%, at least 96.0%, at least 97.0%, at least 98.0%, at least 98.5%, or at least 99.0% identical to the amino acid sequence as represented by SEQ ID NO:12 over a stretch of at least 150, at least 160, at least 170, at least 180, at least 190, at least 200, at least 210, at least 220, at least 230, at least 240, at least 250, at least 260, at least 270, at least 280, at least 290 or at least 300 amino acid residues,
   that is at least 45.0%, at least 50.0%, at least 55.0%, at least 60.0%, at least 65.0%, at least 70.0%, at least 75.0%, at least 80.0%, at least 85.0%, at least 90.0%, at least 95.0%, at least 96.0%, at least 97.0%, at least 98.0%, at least 98.5%, or at least 99.0% identical to the full-length amino acid sequence as represented by SEQ ID NO:12, or
   as represented by any one of SEQ ID NOs: 05, 04, 12, 01, 02, 03, 06, 07 or 08.

9. Method according to any one of embodiment 6 to 8, wherein the cultivation medium contains at least one carbon source selected from the group consisting of glucose, fructose, sucrose, and glycerol.

10. Method according to any one of previous embodiments, wherein the cultivation or incubation medium contains at least one compound selected from the group consisting of lactose, galactose, glucose, sialic acid and CMP-sialic acid.

11. Method according to any one of previous embodiments, wherein the sialylated oligosaccharide, preferably 3'sialylated oligosaccharide, more preferably 3'SL, is recovered from the cultivation or incubation medium and/or the cell.

12. Method according to any one of previous embodiments, the method comprising:
   i) Use of a cultivation or incubation medium comprising at least one precursor and/or acceptor for the production of the sialylated oligosaccharide, preferably 3'sialylated oligosaccharide, more preferably 3'SL, and/or
   ii) Adding to the cultivation or incubation medium at least one precursor and/or acceptor feed for the production of the sialylated oligosaccharide, preferably 3'sialylated oligosaccharide, more preferably 3'SL,
   preferably the precursor is chosen from the list comprising sialic acid, CMP-sialic acid, glucose, galactose and UDP-galactose,
   preferably the acceptor is lactose.

13. Method according to any one of previous embodiments, the method comprising at least one of the following steps:
   i) Use of a cultivation or incubation medium comprising at least one precursor and/or acceptor;
   ii) Adding to the cultivation or incubation medium in a reactor or incubator at least one precursor and/or acceptor feed wherein the total reactor or incubator volume ranges from 250 mL to 10,000 m$^3$ (cubic meter), preferably in a continuous manner, and preferably so that the final volume of the cultivation or incubation medium is not more than three-fold, preferably not more than two-fold, more preferably less than 2-fold of the volume of the cultivation or incubation medium before the addition of the precursor and/or acceptor feed;
   iii) Adding to the cultivation or incubation medium in a reactor or incubator at least one precursor and/or acceptor feed wherein the total reactor or incubator volume ranges from 250 mL to 10,000 m$^3$ (cubic meter), preferably in a continuous manner, and preferably so that the final volume of the cultivation or incubation medium is not more than three-fold, preferably not more than two-fold, more preferably less than two-fold of the volume of the cultivation or incubation medium before the addition of the precursor and/or acceptor feed and wherein preferably, the pH of the precursor and/or acceptor feed is set between 2.0 and 10.0 and wherein preferably, the temperature of the precursor and/or acceptor feed is kept between 20° C. and 80° C.;
   iv) Adding at least one precursor and/or acceptor feed in a continuous manner to the cultivation or incubation medium over the course of 1 day, 2 days, 3 days, 4 days, 5 days by means of a precursor and/or acceptor feeding solution;
   v) Adding at least one precursor and/or acceptor feed in a continuous manner to the cultivation or incubation medium over the course of 1 day, 2 days, 3 days, 4 days, 5 days by means of a precursor and/or acceptor feeding solution and wherein the concentration of the precursor and/or acceptor feeding solution is 50 g/L, preferably 75 g/L, more preferably 100 g/L, more preferably 125 g/L, more preferably 150 g/L, more preferably 175 g/L, more preferably 200 g/L, more preferably 225 g/L, more preferably 250 g/L, more preferably 275 g/L, more preferably 300 g/L, more preferably 325 g/L, more preferably 350 g/L, more preferably 375 g/L, more preferably, 400 g/L, more preferably 450 g/L, more preferably 500 g/L, even more preferably, 550 g/L, most preferably 600 g/L; and wherein preferably, the pH of the precursor and/or acceptor feeding solution is set between 2.0 and 10.0 and wherein preferably, the temperature of the precursor and/or acceptor feeding solution is kept between 20° C. and 80° C.;

the method resulting in the sialylated oligosaccharide, preferably a 3'sialylated oligosaccharide, more preferably 3'SL, with a concentration of at least 50 g/L, preferably at least 75 g/L, more preferably at least 90 g/L, more preferably at least 100 g/L, more preferably at least 125 g/L, more preferably at least 150 g/L, more preferably at least 175 g/L, more preferably at least 200 g/L in the final volume of the cultivation or incubation, wherein preferably the precursor is chosen from the list comprising sialic acid, CMP-sialic acid, glucose, galactose and UDP-galactose, and wherein preferably the acceptor is lactose.

14. Method according to any one of embodiments 1 to 12, the method comprising at least one of the following steps:
   i) Use of a cultivation or incubation medium comprising at least 50, more preferably at least 75, more preferably at least 100, more preferably at least 120, more preferably at least 150 grams of precursor per liter of initial reactor or incubator volume wherein the reactor or incubator volume ranges from 250 mL to 10,000 m$^3$ (cubic meter);
   ii) Use of a cultivation or incubation medium comprising at least 50, more preferably at least 75, more preferably at least 100, more preferably at least 120, more preferably at least 150 grams of acceptor per liter of initial reactor or incubator volume wherein the reactor or incubator volume ranges from 250 mL to 10,000 m$^3$ (cubic meter);
   iii) Adding to the cultivation or incubation medium in a reactor or incubator a precursor feed comprising at least 50, more preferably at least 75, more preferably at least 100, more preferably at least 120, more preferably at least 150 grams of precursor per liter of initial reactor or incubator volume wherein the reactor or incubator volume ranges from 250 mL to 10,000 m$^3$ (cubic meter), preferably in a continuous manner, and preferably so that the final volume of the cultivation or incubation medium is not more than three-fold, preferably not more than two-fold, more preferably less than 2-fold of the volume of the cultivation or incubation medium before the addition of the precursor feed;
   iv) Adding to the cultivation or incubation medium in a reactor or incubator an acceptor feed comprising at least 50, more preferably at least 75, more preferably at least 100, more preferably at least 120, more preferably at least 150 grams of acceptor per liter of initial reactor or incubator volume wherein the reactor or incubator volume ranges from 250 mL to 10,000 m$^3$ (cubic meter), preferably in a continuous manner, and preferably so that the final volume of the cultivation or incubation medium is not more than three-fold, preferably not more than two-fold, more preferably less than 2-fold of the volume of the cultivation or incubation medium before the addition of the acceptor feed;
   v) Adding to the cultivation or incubation medium a precursor feed comprising at least 50, more preferably at least 75, more preferably at least 100, more preferably at least 120, more preferably at least 150 grams of precursor per liter of initial reactor or incubator volume wherein the total reactor or incubator volume ranges from 250 mL to 10,000 m$^3$ (cubic meter), preferably in a continuous manner, and preferably so that the final volume of the cultivation or incubation medium is not more than three-fold, preferably not more than two-fold, more preferably less than 2-fold of the volume of the cultivation or incubation medium before the addition of the precursor feed and wherein preferably, the pH of the precursor feed is set between 2.0 and 10.0 and wherein preferably, the temperature of the precursor feed is kept between 20° C. and 80° C.;
   vi) Adding to the cultivation or incubation medium an acceptor feed comprising at least 50, more preferably at least 75, more preferably at least 100, more preferably at least 120, more preferably at least 150 grams of acceptor per liter of initial reactor or incubator volume wherein the total reactor or incubator volume ranges from 250 mL to 10,000 m$^3$ (cubic meter), preferably in a continuous manner, and preferably so that the final volume of the cultivation or incubation medium is not more than three-fold, preferably not more than two-fold, more preferably less than 2-fold of the volume of the cultivation or incubation medium before the addition of the acceptor feed and wherein preferably, the pH of the acceptor feed is set between 2.0 and 10.0 and wherein preferably, the temperature of the acceptor feed is kept between 20° C. and 80° C.;
   vii) Adding a precursor and/or acceptor feed in a continuous manner to the cultivation or incubation medium over the course of 1 day, 2 days, 3 days, 4 days, 5 days by means of a precursor and/or acceptor feeding solution;
   viii) Adding a precursor feed in a continuous manner to the cultivation or incubation medium over the course of 1 day, 2 days, 3 days, 4 days, 5 days by means of a precursor feeding solution and wherein the concentration of the precursor feeding solution is 50 g/L, preferably 75 g/L, more preferably 100 g/L, more preferably 125 g/L, more preferably 150 g/L, more preferably 175 g/L, more preferably 200 g/L, more preferably 225 g/L, more preferably 250 g/L, more preferably 275 g/L, more preferably 300 g/L, more preferably 325 g/L, more preferably 350 g/L, more preferably 375 g/L, more preferably, 400 g/L, more preferably 450 g/L, more preferably 500 g/L, even more preferably, 550 g/L, most preferably 600 g/L; and wherein preferably the pH of the precursor feeding solution is set between 2.0 and 10.0 and wherein preferably, the temperature of the precursor feeding solution is kept between 20° C. and 80° C.;
   ix) Adding an acceptor feed in a continuous manner to the cultivation or incubation medium over the course of 1 day, 2 days, 3 days, 4 days, 5 days by means of an acceptor feeding solution and wherein the concentration of the acceptor feeding solution is 50 g/L, preferably 75 g/L, more preferably 100 g/L, more preferably 125 g/L, more preferably 150 g/L, more preferably 175 g/L, more preferably 200 g/L, more preferably 225 g/L, more preferably 250 g/L, more preferably 275 g/L, more preferably 300 g/L, more preferably 325 g/L, more preferably 350 g/L, more preferably 375 g/L, more preferably, 400 g/L, more preferably 450 g/L, more preferably 500 g/L, even more preferably, 550 g/L, most preferably 600 g/L; and wherein preferably the pH of the acceptor feeding solution is set between 2.0 and 10.0 and wherein preferably, the temperature of the acceptor feeding solution is kept between 20° C. and 80° C.;

the method resulting in the sialylated oligosaccharide, preferably a 3'sialylated oligosaccharide, more preferably 3'SL, with a concentration of at least 50 g/L, preferably at least 75 g/L, more preferably at least 90 g/L, more preferably at least 100 g/L, more preferably at least 125 g/L, more preferably at least 150 g/L, more preferably at least 175 g/L, more preferably at least 200 g/L in the final volume of the cultivation or incubation, wherein preferably the precursor is chosen from the list comprising sialic acid, CMP-sialic acid, glucose, galactose and UDP-galactose, and wherein preferably the acceptor is lactose.

15. A metabolically engineered cell for the production of a sialylated oligosaccharide, preferably a 3'sialylated oligosaccharide, more preferably 3'SL (Neu5Ac-a2,3-Gal-b1,4-Glc), wherein the cell has been metabolically engineered to possess, preferably to express, a sialyltransferase wherein the sialyltransferase has alpha-2,3-sialyltransferase activity on the galactose (Gal) residue of lactose and comprises an amino acid sequence that is:

at least 67.0% identical over a stretch of at least 150 amino acid residues, preferably at least 200 amino acid residues, to any one of the amino acid sequences as represented by SEQ ID NOs:05, 01, 02, 03, 06, 07 or 08, at least 85.0% identical over a stretch of at least 150 amino acid residues, preferably at least 200 amino acid residues, to the amino acid sequence as represented by SEQ ID NO:04, or at least 60.0% identical over a stretch of at least 150 amino acid residues, preferably at least 200 amino acid residues, to the amino acid sequence as represented by SEQ ID NO:12.

16. Cell according to embodiment 15, wherein the sialyltransferase comprises an amino acid sequence:

that is at least 67.0%, at least 70.0%, at least 75.0%, at least 80.0%, at least 85.0%, at least 90.0%, at least 95.0%, at least 96.0%, at least 97.0%, at least 98.0%, at least 98.5%, or at least 99.0% identical to any one of the amino acid sequences as represented by SEQ ID NOs: 05, 01, 02, 03, 06, 07 or 08 over a stretch of at least 150, at least 160, at least 170, at least 180, at least 190, at least 200, at least 210, at least 220, at least 230, at least 240, at least 250, at least 260, at least 270, at least 280, at least 290 or at least 300 amino acid residues, that is at least 55.0%, at least 60.0%, at least 65.0%, at least 70.0%, at least 75.0%, at least 80.0%, at least 85.0%, at least 90.0%, at least 95.0%, at least 96.0%, at least 97.0%, at least 98.0%, at least 98.5%, or at least 99.0% identical to any one of the full-length amino acid sequences as represented by SEQ ID NOs:05, 01, 02, 03, 06, 07 or 08, that is at least 85.0%, at least 90.0%, at least 95.0%, at least 96.0%, at least 97.0%, at least 98.0%, at least 98.5%, or at least 99.0% identical to the amino acid sequence as represented by SEQ ID NO:04 over a stretch of at least 150, at least 160, at least 170, at least 180, at least 190, at least 200, at least 210, at least 220, at least 230, at least 240, at least 250, at least 260, at least 270, at least 280, at least 290 or at least 300 amino acid residues, that is at least 80.0%, at least 85.0%, at least 90.0%, at least 95.0%, at least 96.0%, at least 97.0%, at least 98.0%, at least 98.5%, or at least 99.0% identical to the full-length amino acid sequence as represented by SEQ ID NO:04, that is at least 60.0%, at least 65.0%, at least 70.0%, at least 75.0%, at least 80.0%, at least 85.0%, at least 90.0%, at least 95.0%, at least 96.0%, at least 97.0%, at least 98.0%, at least 98.5%, or at least 99.0% identical to the amino acid sequence as represented by SEQ ID NO:12 over a stretch of at least 150, at least 160, at least 170, at least 180, at least 190, at least 200, at least 210, at least 220, at least 230, at least 240, at least 250, at least 260, at least 270, at least 280, at least 290 or at least 300 amino acid residues, that is at least 45.0%, at least 50.0%, at least 55.0%, at least 60.0%, at least 65.0%, at least 70.0%, at least 75.0%, at least 80.0%, at least 85.0%, at least 90.0%, at least 95.0%, at least 96.0%, at least 97.0%, at least 98.0%, at least 98.5%, or at least 99.0% identical to the full-length amino acid sequence as represented by SEQ ID NO:12, or as represented by any one of SEQ ID NOs:5, 4, 12, 1, 2, 3, 6, 7 or 8.

17. Cell according to any one of embodiment 15 or 16, wherein the cell contains a nucleic acid molecule that comprises a polynucleotide sequence that encodes the sialyltransferase.

18. Cell according to any one of embodiments 15 to 17, wherein the cell is a bacterium, fungus, yeast, a plant cell, an animal cell, or a protozoan cell, preferably the bacterium is an *Escherichia coli* strain, more preferably an *E. coli* strain that is a K-12 strain, even more preferably the *E. coli* K-12 strain is *E. coli* MG1655, preferably the fungus belongs to a genus chosen from the group comprising *Rhizopus, Dictyostelium, Penicillium, Mucor* or *Aspergillus,* preferably the yeast belongs to a genus chosen from the group comprising *Saccharomyces, Zygosaccharomyces, Pichia, Komagataella, Hansenula, Yarrowia, Starmerella, Kluyveromyces* or Debaromyces, preferably the plant cell is an algal cell or is derived from tobacco, alfalfa, rice, tomato, cotton, rapeseed, soy, maize, or corn plant, preferably the animal cell is derived from non-human mammals, birds, fish, invertebrates, reptiles, amphibians or insects or is a genetically engineered cell line derived from human cells excluding embryonic stem cells, more preferably the human and non-human mammalian cell is an epithelial cell, an embryonic kidney cell, a fibroblast cell, a COS cell, a Chinese hamster ovary (CHO) cell, a murine myeloma cell, an NIH-3T3 cell, a non-mammary adult stem cell or derivatives thereof, more preferably the insect cell is derived from *Spodoptera frugiperda, Bombyx mori, Mamestra brassicae, Trichoplusia ni* or *Drosophila melanogaster,* preferably the protozoan cell is a *Leishmania tarentolae* cell.

19. Cell according to any one of embodiments 15 to 18, wherein the cell is selected from the group consisting of prokaryotic cells and eukaryotic cells, preferably from the group consisting of yeast cells, bacterial cells, archaebacterial cells, algae cells, and fungal cells.

20. Cell according to any one of embodiments 15 to 19, wherein the cell comprises a nucleic acid molecule comprising a polynucleotide sequence encoding the sialyltransferase and operably linked to control sequences recognized by the cell, wherein the sequence is foreign to the cell, the sequence further i) being integrated in the genome of the cell and/or ii) presented to the cell on a vector.

21. Cell according to any one of embodiments 15 to 20, wherein the cell comprises a catabolic pathway for selected mono-, di- or oligosaccharides that is at least partially inactivated, the mono-, di-, or oligosaccharides being involved in and/or required for the synthesis of a sialylated oligosaccharide, preferably a 3'sialylated oligosaccharide, more preferably 3'SL.

22. An isolated nucleic acid molecule encoding a sialyltransferase wherein the sialyltransferase has alpha-2,3-sialyltransferase activity on the galactose (Gal) residue of lactose and comprises an amino acid sequence that is:
- at least 67.0% identical over a stretch of at least 150 amino acid residues, preferably at least 200 amino acid residues, to any one of the amino acid sequences as represented by SEQ ID NOs:5, 1, 2, 3, 6, 7, or 8,
- at least 85.0% identical over a stretch of at least 150 amino acid residues, preferably at least 200 amino acid residues, to the amino acid sequence as represented by SEQ ID NO:4, or
- at least 60.0% identical over a stretch of at least 150 amino acid residues, preferably at least 200 amino acid residues, to the amino acid sequence as represented by SEQ ID NO:12.

23. An isolated nucleic acid molecule according to embodiment 22, wherein the sialyltransferase comprises an amino acid sequence:
- that is at least 67.0%, at least 70.0%, at least 75.0%, at least 80.0%, at least 85.0%, at least 90.0%, at least 95.0%, at least 96.0%, at least 97.0%, at least 98.0%, at least 98.5%, or at least 99.0% identical to any one of the amino acid sequences as represented by SEQ ID NOs: 05, 01, 02, 03, 06, 07 or 08 over a stretch of at least 150, at least 160, at least 170, at least 180, at least 190, at least 200, at least 210, at least 220, at least 230, at least 240, at least 250, at least 260, at least 270, at least 280, at least 290 or at least 300 amino acid residues,
- that is at least 55.0%, at least 60.0%, at least 65.0%, at least 70.0%, at least 75.0%, at least 80.0%, at least 85.0%, at least 90.0%, at least 95.0%, at least 96.0%, at least 97.0%, at least 98.0%, at least 98.5%, or at least 99.0% identical to any one of the full-length amino acid sequences as represented by SEQ ID NOs:5, 1, 2, 3, 6, 7, or 8,
- that is at least 85.0%, at least 90.0%, at least 95.0%, at least 96.0%, at least 97.0%, at least 98.0%, at least 98.5%, or at least 99.0% identical to the amino acid sequence as represented by SEQ ID NO:4 over a stretch of at least 150, at least 160, at least 170, at least 180, at least 190, at least 200, at least 210, at least 220, at least 230, at least 240, at least 250, at least 260, at least 270, at least 280, at least 290 or at least 300 amino acid residues,
- that is at least 80.0%, at least 85.0%, at least 90.0%, at least 95.0%, at least 96.0%, at least 97.0%, at least 98.0%, at least 98.5%, or at least 99.0% identical to the full-length amino acid sequence as represented by SEQ ID NO:4,
- that is at least 60.0%, at least 65.0%, at least 70.0%, at least 75.0%, at least 80.0%, at least 85.0%, at least 90.0%, at least 95.0%, at least 96.0%, at least 97.0%, at least 98.0%, at least 98.5%, or at least 99.0% identical to the amino acid sequence as represented by SEQ ID NO:12 over a stretch of at least 150, at least 160, at least 170, at least 180, at least 190, at least 200, at least 210, at least 220, at least 230, at least 240, at least 250, at least 260, at least 270, at least 280, at least 290 or at least 300 amino acid residues,
- that is at least 45.0%, at least 50.0%, at least 55.0%, at least 60.0%, at least 65.0%, at least 70.0%, at least 75.0%, at least 80.0%, at least 85.0%, at least 90.0%, at least 95.0%, at least 96.0%, at least 97.0%, at least 98.0%, at least 98.5%, or at least 99.0% identical to the full-length amino acid sequence as represented by SEQ ID NO:12, or
- as represented by any one of SEQ ID NOs:5, 4, 12, 1, 2, 3, 6, 7, or 8.

24. A vector comprising the nucleic acid molecule of any one of embodiments 22 or 23.

25. Use of a sialyltransferase that has alpha-2,3-sialyltransferase activity on the galactose (Gal) residue of lactose and that comprises an amino acid sequence:
- that is at least 67.0%, at least 70.0%, at least 75.0%, at least 80.0%, at least 85.0%, at least 90.0%, at least 95.0%, at least 96.0%, at least 97.0%, at least 98.0%, at least 98.5%, or at least 99.0% identical to any one of the amino acid sequences as represented by SEQ ID NOs: 05, 01, 02, 03, 06, 07 or 08 over a stretch of at least 150, at least 160, at least 170, at least 180, at least 190, at least 200, at least 210, at least 220, at least 230, at least 240, at least 250, at least 260, at least 270, at least 280, at least 290 or at least 300 amino acid residues,
- that is at least 55.0%, at least 60.0%, at least 65.0%, at least 70.0%, at least 75.0%, at least 80.0%, at least 85.0%, at least 90.0%, at least 95.0%, at least 96.0%, at least 97.0%, at least 98.0%, at least 98.5%, or at least 99.0% identical to any one of the full-length amino acid sequences as represented by SEQ ID NOs:5, 1, 2, 3, 6, 7, or 8,
- that is at least 85.0%, at least 90.0%, at least 95.0%, at least 96.0%, at least 97.0%, at least 98.0%, at least 98.5%, or at least 99.0% identical to the amino acid sequence as represented by SEQ ID NO:4 over a stretch of at least 150, at least 160, at least 170, at least 180, at least 190, at least 200, at least 210, at least 220, at least 230, at least 240, at least 250, at least 260, at least 270, at least 280, at least 290 or at least 300 amino acid residues,
- that is at least 80.0%, at least 85.0%, at least 90.0%, at least 95.0%, at least 96.0%, at least 97.0%, at least 98.0%, at least 98.5%, or at least 99.0% identical to the full-length amino acid sequence as represented by SEQ ID NO:4,
- that is at least 60.0%, at least 65.0%, at least 70.0%, at least 75.0%, at least 80.0%, at least 85.0%, at least 90.0%, at least 95.0%, at least 96.0%, at least 97.0%, at least 98.0%, at least 98.5%, or at least 99.0% identical to the amino acid sequence as represented by SEQ ID NO:12 over a stretch of at least 150, at least 160, at least 170, at least 180, at least 190, at least 200, at least 210, at least 220, at least 230, at least 240, at least 250, at least 260, at least 270, at least 280, at least 290 or at least 300 amino acid residues,
- that is at least 45.0%, at least 50.0%, at least 55.0%, at least 60.0%, at least 65.0%, at least 70.0%, at least 75.0%, at least 80.0%, at least 85.0%, at least 90.0%, at least 95.0%, at least 96.0%, at least 97.0%, at least 98.0%, at least 98.5%, or at least 99.0% identical to the full-length amino acid sequence as represented by SEQ ID NO:12, or as represented by any one of SEQ ID NOs:5, 4, 12, 1, 2, 3, 6, 7, or 8,
for production of a sialylated oligosaccharide, preferably a 3'sialylated oligosaccharide, more preferably 3'SL.

26. Use of a cell according to any one of embodiments 15 to 21 for production of a sialylated oligosaccharide, preferably a 3'sialylated oligosaccharide, more preferably 3'SL.

27. Use of a method according to any one of embodiments 1 to 14 for production of a sialylated oligosaccharide, preferably a 3'sialylated oligosaccharide, more preferably 3'SL.

28. Use of an isolated nucleic acid molecule according to any one of embodiments 22 or 23 for production of a sialylated oligosaccharide, preferably a 3'sialylated oligosaccharide, more preferably 3'SL.

29. Use of a vector according to embodiment 24 for production of a sialylated oligosaccharide, preferably a 3'sialylated oligosaccharide, more preferably 3'SL.

Moreover, this disclosure relates to the following preferred specific embodiments:

1. Method for the production of a 3'sialylated oligosaccharide, the method comprising: contacting a sialyltransferase with a mixture comprising a donor comprising a sialic acid residue, and an acceptor chosen from the list comprising an oligosaccharide or a disaccharide, under conditions wherein the sialyltransferase catalyzes the transfer of a sialic acid residue from the donor to the acceptor, thereby producing the 3'sialylated oligosaccharide, wherein the sialyltransferase has alpha-2,3-sialyltransferase activity on the galactose (Gal) residue of lactose and comprises an amino acid sequence that is at least 80.0% identical to any one of the full-length amino acid sequences as represented by SEQ ID NOs:05, 04, 12, 01, 02, 03, 06, 07 or 08, preferably, separating the produced 3'sialylated oligosaccharide.

2. Method according to preferred embodiment 1, the method comprising: contacting a cell extract comprising the sialyltransferase with a mixture comprising a donor comprising a sialic acid residue, and an acceptor comprising an oligosaccharide or disaccharide, under conditions wherein the sialyltransferase catalyzes the transfer of a sialic acid residue from the donor to the acceptor, thereby producing the 3'sialylated oligosaccharide.

3. Method according to any one of preferred embodiment 1 or 2, wherein the 3'sialylated oligosaccharide is produced in a cell-free system.

4. Method for the production of a 3'sialylated oligosaccharide, the method comprising the steps of:
   i. providing a cell, preferably a single cell, expressing, preferably heterologously expressing, more preferably overexpressing, even more preferably heterologously overexpressing, a sialyltransferase wherein the sialyltransferase has alpha-2,3-sialyltransferase activity on the galactose (Gal) residue of lactose and comprises an amino acid sequence that is at least 80.0% identical to any one of the full-length amino acid sequences as represented by SEQ ID NOs:5, 4, 12, 1, 2, 3, 6, 7, or 8,
   ii. providing CMP-sialic acid, optionally the CMP-sialic acid is produced by the cell, and
   iii. providing an oligosaccharide or disaccharide, optionally the oligosaccharide or disaccharide is produced by the cell, and
   iv. cultivating and/or incubating the cell under conditions a) permissive to express the sialyltransferase, optionally permissive to produce the CMP-sialic acid and/or the oligosaccharide or disaccharide, and b) wherein the sialyltransferase catalyzes the transfer of a sialic residue from the CMP-sialic acid to the acceptor resulting in the production of the 3'sialylated oligosaccharide,
   v. preferably, separating the 3'sialylated oligosaccharide from the cultivation or incubation.

5. Method according to preferred embodiment 4, wherein the cell is a metabolically engineered cell, preferably wherein the cell is metabolically engineered for the production of the 3'sialylated oligosaccharide.

6. Method according to any one of previous preferred embodiments, wherein the sialic acid residue is at least one chosen from the list consisting of Neu4Ac; Neu5Ac; Neu4,5Ac2; Neu5,7Ac2; Neu5,8Ac2; Neu5,9Ac2; Neu4,5,9Ac3; Neu5,7,9Ac3; Neu5,8,9Ac3; Neu4,5,7,9Ac4; Neu5,7,8,9Ac4; Neu4,5,7,8,9Ac5; Neu5Gc and 2-keto-3-deoxy-manno-octulonic acid (KDO).

7. Method according to any one of previous preferred embodiments, wherein the donor comprising a sialic acid residue is CMP-sialic acid, preferably chosen from the list consisting of CMP-Neu5Ac, CMP-Neu4Ac, CMP-Neu5Ac9N3, CMP-Neu4,5Ac2, CMP-Neu5,7Ac2, CMP-Neu5,9Ac2, CMP-Neu5,7(8,9)Ac2, CMP-N-glycolyl-neuraminic acid (CMP-Neu5Gc) and CMP-KDO.

8. Method according to any one of previous preferred embodiments, wherein the 3'sialylated oligosaccharide is 3'sialyllactose (3'SL, Neu5Ac-a2,3-Gal-b1,4-Glc) and the acceptor is lactose.

9. Method according to any one of previous preferred embodiments, wherein the 3'sialylated oligosaccharide is a saccharide modified with KDO, preferably 3'KDO-lactose, and the acceptor is lactose.

10. Method according to any one of previous preferred embodiments, wherein the 3'sialylated oligosaccharide is a mixture of 3'sialyllactose and 3'KDO-lactose, and the acceptor is lactose.

11. Method according to any one of previous preferred embodiments, wherein the sialyltransferase comprises an amino acid sequence:
   that is at least 80.0%, at least 85.0%, at least 90.0%, at least 95.0%, at least 96.0%, at least 97.0%, at least 98.0%, at least 98.5%, or at least 99.0% identical to any one of the full-length amino acid sequences as represented by SEQ ID NOs:5, 4, 12, 1, 2, 3, 6, 7, or 8, or
   as represented by any one of SEQ ID NOs:5, 4, 12, 1, 2, 3, 6, 7, or 8.

12. Method according to any one of previous preferred embodiments, the method comprising:
   i) Use of a cultivation or incubation medium comprising at least one precursor and/or acceptor for the production of the 3'sialylated oligosaccharide, and/or
   ii) Adding to the cultivation or incubation medium at least one precursor and/or acceptor feed for the production of the 3'sialylated oligosaccharide,
   preferably the precursor is chosen from the list comprising sialic acid, CMP-sialic acid, CMP-Neu5Ac, CMP-KDO, glucose, galactose and UDP-galactose,
   preferably the acceptor is lactose.

13. Method according to preferred embodiment 12, wherein the cultivation medium or incubation medium contains
   at least one carbon source selected from the group consisting of glucose, fructose, sucrose, and glycerol, and/or
   at least one compound selected from the group consisting of lactose, galactose, glucose, sialic acid, CMP-sialic acid, CMP-Neu5Ac and CMP-KDO.

14. Method according to any one of previous preferred embodiments, wherein the 3'sialylated oligosaccharide is recovered from the cultivation or incubation medium and/or the cell.

15. Method according to any one of previous preferred embodiments, wherein the method results in the production of 45 g/L or more, preferably 50 g/L or more, more preferably 60 g/L or more, of a 3'sialylated oligosaccharide.

16. Method according to any one of previous preferred embodiments, wherein the method results in the production of 10 g/L or less, preferably 5 g/L or less, more preferably 1 g/L or less, even more preferably 0.5 g/L or less, even more preferably 0.4 g/L or less, even more preferably 0.3 g/L or less, even more preferably 0.2 g/L or less, most preferably 0.1 g/L or less of 3'-KDO-lactose.

17. Method according to any one of previous preferred embodiments, wherein the method results in the production of a saccharide mixture comprising 45 g/L or more, preferably 50 g/L or more, more preferably 60 g/L or more, of a 3'sialylated oligosaccharide wherein the 3'sialylated oligosaccharide is not 3'KDO-lactose, preferably the 3'sialylated oligosaccharide is 3'SL, and 10 g/L or less, preferably 5 g/L or less, more preferably 1 g/L or less, even more preferably 0.5 g/L or less, even more preferably 0.4 g/L or less, even more preferably 0.3 g/L or less, even more preferably 0.2 g/L or less, most preferably 0.1 g/L or less of a saccharide modified with KDO, preferably KDO-lactose, more preferably 3'-KDO-lactose.

18. A metabolically engineered cell for the production of a 3'sialylated oligosaccharide, wherein the cell has been metabolically engineered to possess, preferably to express, a sialyltransferase wherein the sialyltransferase has alpha-2,3-sialyltransferase activity on the galactose (Gal) residue of lactose and comprises an amino acid sequence that is at least 80.0% identical to any one of the full-length amino acid sequences as represented by SEQ ID NOs:05, 04, 12, 01, 02, 03, 06, 07 or 08.

19. Cell according to preferred embodiment 18, wherein the sialyltransferase comprises an amino acid sequence:
that is at least 80.0%, at least 85.0%, at least 90.0%, at least 95.0%, at least 96.0%, at least 97.0%, at least 98.0%, at least 98.5%, or at least 99.0% identical to any one of the full-length amino acid sequences as represented by SEQ ID NOs:5, 4, 12, 1, 2, 3, 6, 7, or 8, or
as represented by any one of SEQ ID NOs:5, 4, 12, 1, 2, 3, 6, 7, or 8.

20. Cell according to any one of preferred embodiment 18 or 19, wherein the cell is selected from the group consisting of prokaryotic cells and eukaryotic cells, preferably from the group consisting of yeast cells, bacterial cells, archaebacterial cells, algae cells, and fungal cells.

21. Cell according to any one of preferred embodiments 18 to 20, wherein the cell comprises a nucleic acid molecule comprising a polynucleotide sequence encoding the sialyltransferase and operably linked to control sequences recognized by the cell, wherein the sequence is foreign to the cell, the sequence further i) being integrated in the genome of the cell and/or ii) presented to the cell on a vector.

22. Cell according to any one of preferred embodiments 18 to 21, wherein the cell comprises a catabolic pathway for selected mono-, di- or oligosaccharides that is at least partially inactivated, the mono-, di-, or oligosaccharides being involved in and/or required for the synthesis of a 3'sialylated oligosaccharide.

23. An isolated nucleic acid molecule encoding a sialyltransferase wherein the sialyltransferase has alpha-2,3-sialyltransferase activity on the galactose (Gal) residue of lactose and comprises an amino acid sequence that is at least 80.0% identical to any one of the full-length amino acid sequences as represented by SEQ ID NOs:05, 04, 12, 01, 02, 03, 06, 07 or 08.

24. An isolated nucleic acid molecule according to preferred embodiment 23, wherein the sialyltransferase comprises an amino acid sequence:
that is at least 80.0%, at least 85.0%, at least 90.0%, at least 95.0%, at least 96.0%, at least 97.0%, at least 98.0%, at least 98.5%, or at least 99.0% identical to any one of the full-length amino acid sequences as represented by SEQ ID NOs:5, 4, 12, 1, 2, 3, 6, 7, or 8, or
as represented by any one of SEQ ID NOs:5, 4, 12, 1, 2, 3, 6, 7, or 8.

25. A vector comprising the nucleic acid molecule of any one of preferred embodiment 23 or 24.

26. Use of a sialyltransferase that has alpha-2,3-sialyltransferase activity on the galactose (Gal) residue of lactose and that comprises an amino acid sequence:
that is at least 80.0%, at least 85.0%, at least 90.0%, at least 95.0%, at least 96.0%, at least 97.0%, at least 98.0%, at least 98.5%, or at least 99.0% identical to any one of the full-length amino acid sequences as represented by SEQ ID NOs:05, 04, 12, 01, 02, 03, 06, 07 or 08, or
as represented by any one of SEQ ID NOs:5, 4, 12, 1, 2, 3, 6, 7, or 8,
for production of a 3'sialylated oligosaccharide.

27. Use of a cell according to any one of preferred embodiments 18 to 21 for production of a 3'sialylated oligosaccharide.

28. Use of a method according to any one of preferred embodiments 1 to 17 for production of a 3'sialylated oligosaccharide.

29. Use of an isolated nucleic acid molecule according to any one of preferred embodiment 23 or 24 for production of a 3'sialylated oligosaccharide.

30. Use of a vector according to preferred embodiment 25 for production of a 3'sialylated oligosaccharide.

This disclosure will be described in more detail in the examples. The following examples will serve as further illustration and clarification of this disclosure and are not intended to be limiting.

Examples

Example 1. Calculation of Percentage Identity Between Nucleotide or Polypeptide Sequences Methods for the alignment of sequences for comparison are well known in the art, such methods include GAP, BESTFIT, BLAST, FASTA and TFASTA. GAP uses the algorithm of Needleman and Wunsch (J. Mol. Biol. (1970) 48: 443-453) to find the global (i.e., spanning the full-length sequences) alignment of two sequences that maximizes the number of matches and minimizes the number of gaps. The BLAST algorithm (Altschul et al., J. Mol. Biol. (1990) 215: 403-10) calculates the global percentage sequence identity (i.e., over the full-length sequence) and performs a statistical analysis of the similarity between the two sequences. The software for performing BLAST analysis is publicly available through the National Centre for Biotechnology Information (NCBI). Homologs may readily be identified using, for example, the ClustalW multiple sequence alignment algorithm (version 1.83), with the default pairwise alignment parameters, and a scoring method in percentage. Global percentages of similarity and identity (i.e., spanning the full-length sequences) may also be determined using one of the methods available in the MatGAT software package (Campanella et al., BMC Bioinformatics (2003) 4:29). Minor manual editing may be performed to optimize alignment between conserved motifs, as would be apparent to a person skilled in the art. Furthermore, instead of using full-length sequences for the identification of homologs, specific domains may also be used, to determine the so-called local sequence identity. The sequence identity values may be determined over the entire nucleic acid or amino acid sequence (=local sequence identity search over the full-length sequence resulting in a global sequence identity score) or over selected domains or conserved motif(s) (=local sequence identity search over a partial sequence resulting in a local sequence identity score), using the programs mentioned above using the default parameters. For local alignments, the Smith-Waterman algorithm is particularly useful (Smith T F, Waterman M S (1981) J. Mol. Biol 147(1); 195-7).

Example 2. Materials and Methods

A. *Escherichia coli*
Media and Cultivation

The Luria Broth (LB) medium consisted of 1% tryptone peptone (Difco, Erembodegem, Belgium), 0.5% yeast extract (Difco) and 0.5% sodium chloride (VWR. Leuven, Belgium). The minimal medium used in the cultivation experiments in 96-well plates or in shake flasks contained 2.00 g/L $NH_4Cl$, 5.00 g/L $(NH_4)_2SO_4$, 2.993 g/L $KH_2PO_4$, 7.315 g/L $K_2HPO_4$, 8.372 g/L MOPS, 0.5 g/L NaCl, 0.5 g/L $MgSO_4·7H_2O$, 30 g/L sucrose or 30 g/L glycerol, 1 ml/L vitamin solution, 100 μl/L molybdate solution, and 1 mL/L selenium solution. As specified in the respective examples, 0.30 g/L sialic acid and/or 20 g/L lactose were additionally added to the medium. The minimal medium was set to a pH of 7.0 with 1M KOH. Vitamin solution consisted of 3.6 g/L $FeCl_2·4H_2O$, 5.0 g/L $CaCl_2O·2H_2O$, 1.3 g/L $MnCl_2·2H_2O$, 0.38 g/L $CuCl_2·2H_2O$, 0.5 g/L $CoCl_2·6H_2O$, 0.94 g/L $ZnCl_2$, 0.0311 g/L $H_3BO_4$, 0.4 g/L $Na_2EDTA·2H_2O$ and 1.01 g/L thiamine·HCl. The molybdate solution contained 0.967 g/L $NaMoO_4·2H_2O$. The selenium solution contained 42 g/L $SeO_2$.

The minimal medium for fermentations contained 6.75 g/L $NH_4Cl$, 1.25 g/L $(NH_4)_2SO_4$, 2.93 g/L $KH_2PO_4$ and 7.31 g/L $KH_2PO_4$, 0.5 g/L NaCl, 0.5 g/L $MgSO_4·7H_2O$, 30 g/L sucrose or 30 g/L glycerol, 1 mL/L vitamin solution, 100 μL/L molybdate solution, and 1 mL/L selenium solution with the same composition as described above. As specified in the respective examples, 0.30 g/L sialic acid and/or 20 g/L lactose were additionally added to the medium.

Complex medium was sterilized by autoclaving (121° C., 21 min) and minimal medium by filtration (0.22 μm Sartorius). When necessary, the medium was made selective by adding an antibiotic: e.g., chloramphenicol (20 mg/L), carbenicillin (100 mg/L), spectinomycin (40 mg/L) and/or kanamycin (50 mg/L).

A preculture of 96-well microtiter plate experiments was started from a cryovial, in 150 μL LB and was incubated overnight at 37° C. on an orbital shaker at 800 rpm. This culture was used as inoculum for a 96 well square microtiter plate, with 400 μL minimal medium by diluting 400×. These final 96-well culture plates were then incubated at 37° C. on an orbital shaker at 800 rpm for 72h, or shorter, or longer. To measure sugar concentrations at the end of the cultivation experiment whole broth samples were taken from each well by boiling the culture broth for 15 min at 60° C. before spinning down the cells (=average of intra- and extracellular sugar concentrations).

A preculture for the bioreactor was started from an entire 1 mL cryovial of a certain strain, inoculated in 250 mL or 500 mL minimal medium in a 1 L or 2.5 L shake flask and incubated for 24 h at 37° C. on an orbital shaker at 200 rpm. A 5 L bioreactor was then inoculated (250 mL inoculum in 2 L batch medium); the process was controlled by MFCS control software (Sartorius Stedim Biotech, Melsungen, Germany). Culturing condition were set to 37° C., and maximal stirring; pressure gas flow rates were dependent on the strain and bioreactor. The pH was controlled at 6.8 using 0.5 M $H_2SO_4$ and 20% $NH_4OH$. The exhaust gas was cooled. 10% solution of silicone antifoaming agent was added when foaming raised during the fermentation.

Plasmids pKD46 (Red helper plasmid, Ampicillin resistance), pKD3 (contains an FRT-flanked chloramphenicol resistance (cat) gene), pKD4 (contains an FRT-flanked kanamycin resistance (kan) gene), and pCP20 (expresses FLP recombinase activity) plasmids were obtained from Prof. R. Cunin (Vrije Universiteit Brussel, Belgium in 2007). Plasmids were maintained in the host *E. coli* DH5alpha (F⁻, phi80dlacZΔM15, Δ(lacZYA-argF) U169, deoR, recA1, endA1, hsdR17(rk⁻, mk⁺), phoA, supE44, lambda, thi-1, gyrA96, relA1) bought from Invitrogen.

Strains and Mutations

*Escherichia coli* K12 MG1655 [λ⁻, F⁻, rph-1] was obtained from the *Coli* Genetic Stock Center (US), CGSC Strain #: 7740, in March 2007. Gene disruptions, gene introductions and gene replacements were performed using the technique published by Datsenko and Wanner (PNAS 97 (2000), 6640-6645).

In an example for sialic acid production, the mutant strain was derived from *E. coli* K12 MG1655 comprising genomic knock-ins of constitutive transcriptional units containing one or more copies of a glucosamine 6-phosphate N-acetyltransferase like e.g., GNA1 from *Saccharomyces cerevisiae* (UniProt ID P43577), an N-acylglucosamine 2-epimerase like e.g., AGE from *Bacteroides ovatus* (UniProt ID A7LVG6) and an N-acetylneuraminate synthase like e.g., NeuB from *Neisseria meningitidis* (UniProt ID E0NCD4) or NeuB *Campylobacter jejuni* (UniProt ID Q93MP9). Alternatively, and/or additionally, sialic acid production can be obtained by genomic knock-ins of constitutive transcriptional units containing an UDP-N-acetylglucosamine 2-epimerase like e.g., NeuC from *C. jejuni* (UniProt ID Q93MP8) and an N-acetylneuraminate synthase like e.g., NeuB from *N. meningitidis* (UniProt ID E0NCD4) or NeuB from *Campylobacter jejuni* (UniProt ID Q93MP9). Alternatively and/or additionally, sialic acid production can be obtained by genomic knock-ins of constitutive transcriptional units containing a phosphoglucosamine mutase like e.g., glmM from *E. coli* (UniProt ID P31120, sequence version 03 (23 Jan. 2007)), an N-acetylglucosamine-1-phosphate uridylyltransferase/glucosamine-1-phosphate acetyltransferase like e.g., glmU from *E. coli* (UniProt ID P0ACC7), an UDP-N-acetylglucosamine 2-epimerase like e.g., NeuC from *C. jejuni* (UniProt ID Q93MP8) and an N-acetylneuraminate synthase like e.g., NeuB from *Neisseria meningitidis* (UniProt ID E0NCD4) or NeuB from *Campylobacter jejuni* (UniProt ID Q93MP9). Alternatively, and/or additionally, sialic acid production can be obtained by genomic knock-ins of constitutive transcriptional units containing a bifunctional UDP-GlcNAc 2-epimerase/N-acetylmannosamine kinase like e.g., GNE from *Mus musculus* (strain C57BL6J) (Uni- Prot ID Q91WG8), an N-acylneuraminate-9-phosphate synthetase like e.g., NANS from *Pseudomonas* sp. UW4 (UniProt ID K9NPH9) and an N-acylneuraminate-9-phosphatase like e.g., NANP from *Candidatus Magnetomorum* sp. HK-1 (UniProt ID KPA15328.1) or NANP from *Bacteroides thetaiotaomicron* (UniProt ID Q8A712). Alternatively, and/or additionally, sialic acid production can be obtained by genomic knock-ins of constitutive transcriptional units containing a phosphoglucosamine mutase like e.g., glmM from *E. coli* (UniProt ID P31120, sequence version 03 (23 Jan. 2007)), an N-acetylglucosamine-1-phosphate uridylyltransferase/glucosamine-1-phosphate acetyltransferase like e.g., glmU from *E. coli* (UniProt ID P0ACC7), a bifunctional UDP-GlcNAc 2-epimerase/N-acetylmannosamine kinase like e.g., GNE from *M. musculus* (strain C57BL6J) (UniProt ID Q91WG8), an N-acylneuraminate-9-phosphate synthetase like e.g., NANS from *Pseudomonas* sp. UW4 (UniProt ID K9NPH9) and an N-acylneuraminate-9-phosphatase like e.g., NANP from *Candidatus Magnetomorum* sp. HK-1 (UniProt ID KPA15328.1) or NANP from *Bacteroides thetaiotaomicron* (UniProt ID Q8A712).

Sialic acid production can further be optimized in the modified *E. coli* strain with genomic knock-outs of the *E. coli* genes comprising any one or more of nagA, nagB, nagC, nagD, nagE, nanA, nanE, nanK, manX, manY and manZ as described in WO18122225, and/or genomic knock-outs of the *E. coli* genes comprising any one or more of nanT, poxB, ldhA, adhE, aldB, pflA, pflC, ybiY, ackA and/or pta and with genomic knock-ins of constitutive transcriptional units comprising one or more copies of an L-glutamine-D-fructose-6-phosphate aminotransferase like e.g., the mutant glmS*54 from *E. coli* with SEQ ID NO:10 (differing from the wild-type *E. coli* glmS, having UniProt ID P17169 (sequence version 04 (23 Jan. 2007), by an A39T, an R250C and an G472S mutation as described by Deng et al. (Biochimie 88, 419-29 (2006)) and an acetyl-CoA synthetase like e.g., acs from *E. coli* (UniProt ID P27550, Sequence version 02 (1 Oct. 1993)).

In an example for sialylated oligosaccharide production like e.g., 3'SL (Neu5Ac-a2,3-Gal-b1,4-Glc), the sialic acid production strains were further modified to express an N-acylneuraminate cytidylyltransferase like e.g., the NeuA enzyme from *Pasteurella multocida* (SEQ ID NO:09) and to express an alpha-2,3-sialyltransferase like e.g., PmultST3 from *Pasteurella multocida* (UniProt ID Q9CLP3), a PmultST3-like polypeptide with SEQ ID NO:11 consisting of amino acid residues 1 to 268 of UniProt ID Q9CLP3 having beta-galactoside alpha-2,3-sialyltransferase activity and/or a sialyltransferase selected from the list comprising SEQ ID NOs:1, 2, 3, 4, 5, 6, 7, 8, 12, 14 and 15. Constitutive transcriptional units of the N-acylneuraminate cytidylyltransferase and the sialyltransferase(s) can be delivered to the modified strain either via genomic knock-in or via expression plasmids. The strains were additionally modified with genomic knock-outs of the *E. coli* LacZ, LacY and LacA genes and with a genomic knock-in of a constitutive transcriptional unit for a lactose permease like e.g., *E. coli* LacY (UniProt ID P02920). All modified strains producing sialic acid, CMP-sialic acid and/or sialylated oligosaccharides could optionally be adapted for growth on sucrose via genomic knock-ins of constitutive transcriptional units containing a sucrose transporter like e.g., CscB from *E. coli* W (UniProt ID E0IXR1), a fructose kinase like e.g., Frk originating from *Z. mobilis* (UniProt ID Q03417) and a sucrose phosphorylase like e.g., BaSP from *B. adolescentis* (UniProt ID A0ZZH6).

Alternatively, and/or additionally, sialic acid and/or sialylated oligosaccharide production can further be optimized in the mutant *E. coli* strains with genomic knock-ins of constitutive transcriptional units comprising a membrane transporter protein like e.g., a sialic acid transporter like e.g., nanT from *E. coli* K-12 MG1655 (UniProt ID P41036, sequence version 02 (1 Nov. 1995)), nanT from *E. coli* O6:H1 (UniProt ID Q8FD59), nanT from *E. albertii* (UniProt ID B1EFH1) or a porter like e.g., EntS from *E. coli* (UniProt ID P24077, sequence version 02 (1 Nov. 1997)), EntS from *Kluyvera ascorbata* (UniProt ID A0A378GQ13) or EntS from *Salmonella enterica* subsp. *arizonae* (UniProt ID A0A6Y2K4E8), MdfA from *Cronobacter muytjensii* (UniProt ID A0A2T7ANQ9), MdfA from *Citrobacter youngae* (UniProt ID D4BC23), MdfA from *E. coli* (UniProt ID P0AEY8), MdfA from *Yokenella regensburgei* (UniProt ID G9Z5F4), iceT from *E. coli* (UniProt ID A0A024L207), iceT from *Citrobacter youngae* (UniProt ID D4B8A6), SetA from *E. coli* (UniProt ID P31675, sequence version 03 (11 Oct. 2004)), SetB from *E. coli* (UniProt ID P33026) or SetC from *E. coli* (UniProt ID P31436) or an ABC transporter like e.g., oppF from *E. coli* (UniProt ID P77737), lmrA from *Lactococcus lactis* subsp. *lactis* bv. *diacetylactis* (UniProt ID A0A1V0NEL4), or Blon_2475 from *Bifidobacterium longum* subsp. *infantis* (UniProt ID B7GPD4).

Preferably but not necessarily, any one or more of the glycosyltransferases, the proteins involved in nucleotide-activated sugar synthesis and/or the membrane transporter proteins were N- and/or C-terminally fused to a solubility enhancer tag like e.g., a SUMO-tag, an MBP-tag, His, FLAG, Strep-II, Halo-tag, NusA, thioredoxin, GST and/or the Fh8-tag to enhance their solubility (Costa et al., Front. Microbiol. 2014, /doi.org/10.3389/fmicb.2014.00063; Fox et al., Protein Sci. 2001, 10(3), 622-630; Jia and Jeaon, Open Biol. 2016, 6: 160196).

Optionally, the modified *E. coli* strains were modified with a genomic knock-ins of a constitutive transcriptional unit encoding a chaperone protein like e.g., DnaK, DnaJ, GrpE or the GroEL/ES chaperonin system (Baneyx F., Palumbo J. L. (2003) Improving Heterologous Protein Folding via Molecular Chaperone and Foldase Co-Expression. In: Vaillancourt P. E. (eds) *E. coli* Gene Expression Protocols. Methods in Molecular Biology™, vol 205. Humana Press).

Optionally, the mutant *E. coli* strains are modified to create a glycominimized *E. coli* strain comprising genomic knock-out of any one or more of non-essential glycosyltransferase genes comprising pgaC, pgaD, rfe, rftT, rffM, bcsA, bcsB, bcsC, wcaA, wcaC, wcaE, wcaI, wcaJ, wcaL, waaH, waaF, waaC, waaU, waaZ, waaJ, waaO, waaB, waaS, waaG, waaQ, wbbI, arnC, arnT, yfdH, wbbK, opgG, opgH, ycjM, glgA, glgB, malQ, otsA and yaiP.

All constitutive promoters, UTRs and terminator sequences originated from the libraries described by Cambray et al. (Nucleic Acids Res. 2013, 41(9), 5139-5148), Dunn et al. (Nucleic Acids Res. 1980, 8, 2119-2132), Edens et al. (Nucleic Acids Res. 1975, 2, 1811-1820), Kim and Lee (FEBS Letters 1997, 407, 353-356) and Mutalik et al. (Nat. Methods 2013, No. 10, 354-360).

All strains were stored in cryovials at −80° C. (overnight LB culture mixed in a 1:1 ratio with 70% glycerol).

B. *Saccharomyces cerevisiae*

Media and Cultivation

Strains were grown on Synthetic Defined yeast medium with Complete Supplement Mixture (SD CSM) or CSM drop-out (SD CSM-Ura, SD CSM-Trp, SD CSM-His) containing 6.7 g/L Yeast Nitrogen Base without amino acids (YNB w/o AA, Difco), 20 g/L agar (Difco) (solid cultures), 22 g/L glucose monohydrate or 20 g/L lactose and 0.79 g/L CSM or 0.77 g/L CSM-Ura, 0.77 g/L CSM-Trp, or 0.77 g/L CSM-His (MP Biomedicals). In general, yeast strains were initially grown on SD CSM plates to obtain single colonies. These plates were grown for 2-3 days at 30° C. Starting from a single colony, a preculture was grown over night in 5 mL at 30° C., shaking at 200 rpm. Subsequent 125 mL shake flask experiments were inoculated with 2% of this preculture, in 25 mL media. These shake flasks were incubated at 30° C. with an orbital shaking of 200 rpm.

Strains and Plasmids

S. cerevisiae BY4742 created by Brachmann et al. (Yeast (1998) 14:115-32) was used, available in the Euroscarf culture collection. All mutant strains were created by homologous recombination or plasmid transformation using the method of Gietz (Yeast 11:355-360, 1995). Genes were expressed using synthetic constitutive promoters, as described by e.g., Blazeck (Biotechnology and Bioengineering, Vol. 109, No. 11, 2012), Redden and Alper (Nat. Commun. 2015, 6, 7810), Liu et al. (Microb. Cell Fact. 2020, 19, 38), Xu et al. (Microb. Cell Fact. 2021, 20, 148) and Lee et al. (ACS Synth. Biol. 2015, 4(9), 975-986).

In an example to produce sialic acid and CMP-sialic acid, a yeast expression plasmid was derived from the pRS420-plasmid series (Christianson et al., 1992, Gene 110: 119-122) containing the TRP1 selection marker and constitutive transcriptional units for an L-glutamine-D-fructose-6-phosphate aminotransferase like e.g., the mutant glmS*54 from E. coli with SEQ ID NO:10 (differing from the wild-type E. coli glmS, having UniProt ID P17169 (sequence version 04 (23 Jan. 2007), by an A39T, an R250C and an G472S mutation as described by Deng et al. (Biochimie 88, 419-29 (2006)), a phosphatase like e.g., SurE from E. coli (UniProt ID P0A840), an N-acylglucosamine 2-epimerase like e.g., AGE from B. ovatus (UniProt ID A7LVG6), an N-acetylneuraminate synthase like e.g., NeuB from N. meningitidis (UniProt ID E0NCD4) and an N-acylneuraminate cytidylyltransferase like e.g., NeuA from P. multocida with SEQ ID NO:09. Optionally, a constitutive transcriptional unit for a glucosamine 6-phosphate N-acetyltransferase like e.g., GNA1 from S. cerevisiae (UniProt ID P43577) was added as well. In an example to produce sialylated oligosaccharides, the plasmid further comprised constitutive transcriptional units for a lactose permease like e.g., LAC12 from K. lactis (UniProt ID P07921), and a sialyltransferase with SEQ ID NOs:01, 02, 03, 04, 05, 06, 07, 08, 1112, 14 or 15. Preferably but not necessarily, any one or more of the glycosyltransferases and/or the proteins involved in nucleotide-activated sugar synthesis were N- and/or C-terminally fused to a SUMOstar tag (e.g., obtained from pYSUMOstar, Life Sensors, Malvern, PA) to enhance their solubility. Optionally, the mutant yeast strains were modified with a genomic knock-in of a constitutive transcriptional unit encoding a chaperone protein like e.g., Hsp31, Hsp32, Hsp33, Sno4, Kar2, Ssb1, Sse1, Sse2, Ssa1, Ssa2, Ssa3, Ssa4, Ssb2, Ecml0, Ssc1, Ssq1, Ssz1, Lhs1, Hsp82, Hsc82, Hsp78, Hsp104, Tcp1, Cct4, Cct8, Cct2, Cct3, Cct5, Cct6 or Cct7 (Gong et al., 2009, Mol. Syst. Biol. 5: 275). Plasmids were maintained in the host E. coli DH5alpha (F−, phi80dlacZdeltaM15, delta(lacZYA-argF)U169, deoR, recA1, endA1, hsdR17(rk−, mk+), phoA, supE44, lambda, thi-1, gyrA96, relA1) bought from Invitrogen.

C. Bacillus subtilis

Media and Cultivation

Two media are used to cultivate B. subtilis: i.e., a rich Luria Broth (LB) and a minimal medium for shake flask cultures. The LB medium consisted of 1% tryptone peptone (Difco), 0.5% yeast extract (Difco) and 0.5% sodium chloride (VWR). Luria Broth agar (LBA) plates consisted of the LB media, with 12 g/L agar (Difco) added. The minimal medium contained 2.00 g/L $(NH_4)_2SO_4$, 7.5 g/L $KH_2PO_4$, 17.5 g/L $K_2HPO_4$, 1.25 g/L Na-citrate, 0.25 g/L $MgSO_4·7H_2O$, 0.05 g/L tryptophan, from 10 up to 30 g/L glucose (or another carbon source including but not limited to fructose, maltose, sucrose, glycerol and maltotriose), 10 mL/L trace element mix and 10 mL/L Fe-citrate solution. The medium was set to a pH of 7.0 with 1 M KOH. Depending on the experiment lactose is added as a precursor. The trace element mix consisted of 0.735 g/L $CaCl_2O·2H_2O$, 0.1 g/L $MnCl_2·2H_2O$, 0.033 g/L $CuCl_2·2H_2O$, 0.06 g/L $CoCl_2·6H_2O$, 0.17 g/L $ZnCl_2$, 0.0311 g/L $H_3BO_4$, 0.4 g/L $Na_2EDTA·2H_2O$ and 0.06 g/L $Na_2MoO_4$. The Fe-citrate solution contained 0.135 g/L $FeCl_3·6H_2O$, 1 g/L Na-citrate (Hoch 1973 PMC1212887).

Complex medium, e.g., LB, was sterilized by autoclaving (121° C., 21 min) and minimal medium by filtration (0.22 µm Sartorius). When necessary, the medium was made selective by adding an antibiotic (e.g., zeocin (20 mg/L)).

A preculture of 96-well microtiter plate experiments was started from a cryovial or a single colony from an LB plate, in 150 µL LB and was incubated overnight at 37° C. on an orbital shaker at 800 rpm. This culture was used as inoculum for a 96-well square microtiter plate, with 400 µL minimal medium by diluting 400×. Each strain was grown in multiple wells of the 96-well plate as biological replicates. These final 96-well culture plates were then incubated at 37° C. on an orbital shaker at 800 rpm for 72h, or shorter, or longer. At the end of the cultivation experiment samples were taken from each well to measure the supernatant concentration (extracellular sugar concentrations, after 5 min. spinning down the cells), or by boiling the culture broth for 15 min at 90° C. or for 60 min at 60° C. before spinning down the cells (=whole broth concentration, intra- and extracellular sugar concentrations, as defined herein).

Also, a dilution of the cultures was made to measure the optical density at 600 nm. The cell performance index or CPI was determined by dividing the oligosaccharide concentrations by the biomass, in relative percentages compared to a reference strain. The biomass is empirically determined to be approximately ⅓rd of the optical density measured at 600 nm.

Strains, Plasmids and Mutations

Bacillus subtilis 168 is used as available at the Bacillus Genetic Stock Center (Ohio, USA).

Plasmids for gene deletion via Cre/lox are constructed as described by Yan et al. (Appl & Environm microbial, Sept 2008, p5556-5562). Gene disruption is done via homologous recombination with linear DNA and transformation via the electroporation as described by Xue et al. (J. Microb. Meth. 34 (1999) 183-191). The method of gene knockouts is described by Liu et al. (Metab. Engine. 24 (2014) 61-69). This method uses 1000 bp homologies up- and downstream of the target gene.

Integrative vectors as described by Popp et al. (Sci. Rep., 2017, 7, 15158) are used as expression vector and could be further used for genomic integrations if necessary. A suitable promoter for expression can be derived from the part repository (iGem): sequence id: BBa_K143012, BBa_K823000, BBa_K823002 or BBa_K823003. Cloning can be performed using Gibson Assembly, Golden Gate assembly, Cliva assembly, LCR or restriction ligation.

In an example for sialic acid (Neu5Ac) production, the engineered strain was derived from B. subtilis comprising knockouts of the *B. subtilis* nagA, nagB and gamA genes and genomic knock-ins of constitutive transcriptional units containing a phosphoglucosamine mutase like e.g., glmM from *E. coli* (UniProt ID P31120, sequence version 03 (23 Jan. 2007)), an N-acetylglucosamine-1-phosphate uridylyltransferase/glucosamine-1-phosphate acetyltransferase like e.g., glmU from *E. coli* (UniProt ID P0ACC7), an UDP-N-acetylglucosamine 2-epimerase like e.g., neuC from *C. jejuni* (UniProt ID Q93MP8) and an N-acetylneuraminate synthase like e.g., neuB from *N. meningitidis* (UniProt ID E0NCD4). Sialic acid production can also be obtained in modified *B. subtilis* comprising knockouts of the *B. subtilis* nagA, nagB and gamA genes and genomic knock-ins of constitutive transcriptional units containing an N-acylglucosamine 2-epimerase like e.g., AGE from *B. ovatus* (UniProt ID A7LVG6) and an N-acetylneuraminate synthase like e.g., NeuB from *N. meningitidis* (UniProt ID E0NCD4). To enhance the intracellular glucosamine-6-phosphate pool, the modified strain can further be modified with a genomic knock-in of one or more constitutive transcriptional units containing a glutamine-fructose-6-P-aminotransferase like e.g., the native glutamine-fructose-6-P-aminotransferase glmS (UniProt ID P0CI73). Optionally, the strains were also modified for expression of a phosphatase like e.g., SurE from *E. coli* (UniProt ID P0A840). In an example for sialylated oligosaccharide production, the sialic acid production strains further need to express an N-acylneuraminate cytidylyltransferase like e.g., neuA from *P. multocida* with SEQ ID NO:09, and a sialyltransferase with SEQ ID NOs: 01, 02, 03, 04, 05, 06, 07, 08, 11, 12, 14 or 15. Constitutive transcriptional units of the N-acylneuraminate cytidylyltransferase and the sialyltransferases can be delivered to the engineered strain either via genomic knock-in or via expression plasmids. If the engineered strains producing sialic acid and CMP-sialic acid were intended to make sialylated lactose structures, the strains were additionally modified with a genomic knock-in of a constitutive transcriptional unit for a lactose permease like e.g., the *E. coli* LacY (UniProt ID P02920).

D. *Corynebacterium glutamicum*

Media and Cultivation

Two different media are used to cultivate *C. glutamicum*: i.e., a rich tryptone-yeast extract (TY) medium and a minimal medium. The TY medium consisted of 1.6% tryptone (Difco), 1% yeast extract (Difco) and 0.5% sodium chloride (VWR). TY agar (TYA) plates consisted of the TY media, with 12 g/L agar (Difco) added. The minimal medium for the shake flask experiments contained 20 g/L $(NH_4)_2SO_4$, 5 g/L urea, 1 g/L $KH_2PO_4$, 1 g/L $K2HPO_4$, 0.25 g/L $MgSO_4·7H_2O$, 42 g/L MOPS, from 10 up to 30 g/L glucose (or another carbon source including but not limited to fructose, maltose, sucrose, glycerol and maltotriose) and 1 mL/L trace element mix. Depending on the experiment lactose is added as a precursor. The trace element mix consisted of 10 g/L $CaCl_2$, 10 g/L $FeSO_4·7H_2O$, 10 g/L $MnSO_4·H_2O$, 1 g/L $ZnSO_4·7H_2O$, 0.2 g/L $CuSO_4$, 0.02 g/L $NiCl_2·6H_2O$, 0.2 g/L biotin (pH 7.0) and 0.03 g/L protocatechuic acid.

Complex medium, e.g., TY, was sterilized by autoclaving (121° C., 21 min) and minimal medium by filtration (0.22 µm Sartorius). When necessary, the medium was made selective by adding an antibiotic (e.g., kanamycin, ampicillin).

A preculture of 96-well microtiter plate experiments was started from a cryovial or a single colony from a TY plate, in 150 µL TY and was incubated overnight at 37° C. on an orbital shaker at 800 rpm. This culture was used as inoculum for a 96-well square microtiter plate, with 400 µL minimal medium by diluting 400×. Each strain was grown in multiple wells of the 96-well plate as biological replicates. These final 96-well culture plates were then incubated at 37° C. on an orbital shaker at 800 rpm for 72h, or shorter, or longer. At the end of the cultivation experiment samples were taken from each well to measure the supernatant concentration (extracellular sugar concentrations, after 5 min. spinning down the cells), or by boiling the culture broth for 15 min at 60° C. before spinning down the cells (=whole broth concentration, intra- and extracellular sugar concentrations, as defined herein).

Also, a dilution of the cultures was made to measure the optical density at 600 nm. The cell performance index or CPI was determined by dividing the oligosaccharide concentrations, e.g., 3'SL concentrations, measured in the whole broth by the biomass, in relative percentages compared to the reference strain. The biomass is empirically determined to be approximately ⅓rd of the optical density measured at 600 nm.

Strains and Mutations

*Corynebacterium glutamicum* ATCC 13032 was used as available at the American Type Culture Collection.

Integrative plasmid vectors based on the Cre/loxP technique as described by Suzuki et al. (Appl. Microbiol. Biotechnol., 2005 Apr, 67(2):225-33) and temperature-sensitive shuttle vectors as described by Okibe et al. (J. Microbiol. Meth. 85, 2011, 155-163) are constructed for gene deletions, mutations and insertions. Suitable promoters for (heterologous) gene expression can be derived from Yim et al. (Biotechnol. Bioeng., 2013 Nov, 110(11):2959-69). Cloning can be performed using Gibson Assembly, Golden Gate assembly, Cliva assembly, LCR or restriction ligation.

In an example for sialic acid production, the engineered strain was derived from *C. glutamicum* comprising knockouts of the *C. glutamicum* ldh, cgl2645 and nagB genes and genomic knock-ins of constitutive transcriptional units containing a phosphoglucosamine mutase like e.g., glmM from *E. coli* (UniProt ID P31120, sequence version 03 (23 Jan. 2007)), an N-acetylglucosamine-1-phosphate uridylyltransferase/glucosamine-1-phosphate acetyltransferase like e.g., glmU from *E. coli* (UniProt ID P0ACC7), an UDP-N-acetylglucosamine 2-epimerase like e.g., neuC from *C. jejuni* (UniProt ID Q93MP8) and an N-acetylneuraminate synthase like e.g., neuB from *N. meningitidis* (UniProt ID E0NCD4). To enhance the intracellular glucosamine-6-phosphate pool, the modified strain can further be modified with a genomic knock-in of one or more constitutive transcriptional units containing a glutamine-fructose-6-P-aminotransferase like e.g., the native glutamine-fructose-6-P-aminotransferase glmS (UniProt ID Q8NND3, sequence version 02 (23 Jan. 2007)). In an example for sialylated oligosaccharide production, the sialic acid production strains further need to express an N-acylneuraminate cytidylyltransferase like e.g., neuA from *P. multocida* with SEQ ID NO:09, and a sialyltransferase with SEQ ID NOs:01, 02, 03, 04, 05, 06, 07, 08, 11, 12, 14 or 15. Constitutive transcriptional units of the N-acylneuraminate cytidylyltransferase and the sialyltransferases can be delivered to the engineered strain either via genomic knock-in or via expression plasmids. If the engineered strains producing sialic acid and CMP-sialic acid were intended to make sialylated lactose structures, the strains were additionally modified with a genomic knock-in of a constitutive transcriptional unit for a lactose permease like e.g., the *E. coli* LacY (UniProt ID P02920).

E. *Chlamydomonas reinhardtii*
Media and Cultivation

*C. reinhardtii* cells were cultured in Tris-acetate-phosphate (TAP) medium (pH 7.0). The TAP medium uses a 1000× stock Hutner's trace element mix. Hutner's trace element mix consisted of 50 g/L $Na_2EDTA \cdot H_2O$ (Titriplex III), 22 g/L $ZnSO_4 \cdot 7H_2O$, 11.4 g/L $H_3BO_3$, 5 g/L $MnCl_2 \cdot 4H_2O$, 5 g/L $FeSO_4 \cdot 7H_2O$, 1.6 g/L $CoCl_2 \cdot 6H_2O$, 1.6 g/L $CuSO_4 \cdot 5H_2O$ and 1.1 g/L $(NH_4)_6MoO_3$.

The TAP medium contained 2.42 g/L Tris(tris(hydroxymethyl)aminomethane), 25 mg/L salt stock solution, 0.108 g/L $K2HPO_4$, 0.054 g/L $KH_2PO_4$ and 1.0 mL/L glacial acetic acid. The salt stock solution consisted of 15 g/L $NH_4Cl$, 4 g/L $MgSO_4 \cdot 7H_2O$ and 2 g/L $CaCl_2O \cdot 2H_2O$. As precursor for saccharide synthesis, precursors like e.g., galactose, glucose, fructose, fucose, GlcNAc could be added. Medium was sterilized by autoclaving (121° C., 21 min). For stock cultures on agar slants TAP medium was used containing 1% agar (of purified high strength, 1000 g/cm2).

Cells of *C. reinhardtii* were cultured in selective TAP-agar plates at 23+/−0.5° C. under 14/10 h light/dark cycles with a light intensity of 8000 Lx. Cells were analyzed after 5 to 7 days of cultivation.

For high-density cultures, cells could be cultivated in closed systems like e.g., vertical or horizontal tube photo-closed systems, stirred tank photobioreactors or flat panel photobioreactors as described by Chen et al. (Bioresour. Technol. 2011, 102: 71-81) and Johnson et al. (Biotechnol. Prog. 2018, 34: 811-827).

Strains, Plasmids and Mutations

*C. reinhardtii* wild-type strains 21 gr (CC-1690, wild-type, mt+), 6145C (CC-1691, wild-type, mt−), CC-125 (137c, wild-type, mt+), CC-124 (137c, wild-type, mt−) as available from *Chlamydomonas* Resource Center (www.chlamycollection.org), University of Minnesota, U.S.A.

Expression plasmids originated from pSI103, as available from *Chlamydomonas* Resource Center. Cloning can be performed using Gibson Assembly, Golden Gate assembly, Cliva assembly, LCR or restriction ligation. Suitable promoters for (heterologous) gene expression can be derived from e.g., Scranton et al. (Algal Res. 2016, 15: 135-142). Targeted gene modification (like gene knock-out or gene replacement) can be carried using the Crispr-Cas technology as described e.g., by Jiang et al. (Eukaryotic Cell 2014, 13(11): 1465-1469).

Transformation via electroporation was performed as described by Wang et al. (Biosci. Rep. 2019, 39: BSR2018210). Cells were grown in liquid TAP medium under constant aeration and continuous light with a light intensity of 8000 Lx until the cell density reached 1.0-2.0× $10^7$ cells/mL. Then, the cells were inoculated into fresh liquid TAP medium in a concentration of 1.0×$10^6$ cells/mL and grown under continuous light for 18-20 h until the cell density reached 4.0×$10^6$ cells/mL. Next, cells were collected by centrifugation at 1250 g for 5 min at room temperature, washed and resuspended with pre-chilled liquid TAP medium containing 60 mM sorbitol (Sigma, U.S.A.), and iced for 10 min. Then, 250 µL of cell suspension (corresponding to 5.0×$10^7$ cells) were placed into a pre-chilled 0.4 cm electroporation cuvette with 100 ng plasmid DNA (400 ng/mL). Electroporation was performed with 6 pulses of 500 V each having a pulse length of 4 ms and pulse interval time of 100 ms using a BTX ECM830 electroporation apparatus (1575 Ω, 50 µFD). After electroporation, the cuvette was immediately placed on ice for 10 min. Finally, the cell suspension was transferred into a 50 mL conical centrifuge tube containing 10 mL of fresh liquid TAP medium with 60 mM sorbitol for overnight recovery at dim light by slowly shaking. After overnight recovery, cells were recollected and plated with starch embedding method onto selective 1.5% (w/v) agar-TAP plates containing ampicillin (100 mg/L) or chloramphenicol (100 mg/L). Plates were then incubated at 23+−0.5° C. under continuous illumination with a light intensity of 8000 Lx. Cells were analyzed 5-7 days later.

In an example for production of UDP-galactose, *C. reinhardtii* cells were modified with transcriptional units comprising the gene encoding the galactokinase from *Arabidopsis thaliana* (KIN, UniProt ID Q9SEE5) and the gene encoding the UDP-sugar pyrophosphorylase (USP) from *A. thaliana* (UniProt ID Q9C5I1).

In an example for CMP-sialic acid synthesis, *C. reinhardtii* cells were modified with constitutive transcriptional units for a UDP-N-acetylglucosamine-2-epimerase/N-acetylmannosamine kinase like e.g., GNE from *Homo sapiens* (UniProt ID Q9Y223) or a mutant form of the human GNE polypeptide comprising the R263L mutation, an N-acylneuraminate-9-phosphate synthetase like e.g., NANS from *Homo sapiens* (UniProt ID Q9NR45, sequence version 03 (13 Oct. 2009)) and an N-acylneuraminate cytidylyltransferase like e.g., CMAS from *Homo sapiens* (UniProt ID Q8NFW8, sequence version 02 (1 Feb. 2005)). In an example for production of sialylated oligosaccharides, *C. reinhardtii* cells are modified with a CMP-sialic acid transporter like e.g., CST from *Mus musculus* (UniProt ID Q61420), and a sialyltransferase with SEQ ID NOs:01, 02, 03, 04, 05, 06, 07, 08, 11, 12, 14 or 15.

F. Animal Cells
Isolation of Mesenchymal Stem Cells from Adipose Tissue of Different Animals Fresh adipose tissue is obtained from slaughterhouses (e.g., cattle, pigs, sheep, chicken, ducks, catfish, snake, frogs) or liposuction (e.g., in case of humans, after informed consent) and kept in phosphate buffer saline supplemented with antibiotics. Enzymatic digestion of the adipose tissue is performed followed by centrifugation to isolate mesenchymal stem cells. The isolated mesenchymal stem cells are transferred to cell culture flasks and grown under standard growth conditions, e.g., 37° C., 5% CO2. The initial culture medium includes DMEM-F12, RPMI, and Alpha-MEM medium (supplemented with 15% fetal bovine serum), and 1% antibiotics. The culture medium is subsequently replaced with 10% FBS (fetal bovine serum)-supplemented media after the first passage. For example, Ahmad and Shakoori (2013, Stem Cell Regen. Med. 9(2): 29-36), which is incorporated herein by reference in its entirety for all purposes, describes certain variation(s) of the method(s) described herein in this example.

Isolation of Mesenchymal Stem Cells from Milk

This example illustrates isolation of mesenchymal stem cells from milk collected under aseptic conditions from human or any other mammal(s) such as described herein. An equal volume of phosphate buffer saline is added to diluted milk, followed by centrifugation for 20 min. The cell pellet is washed thrice with phosphate buffer saline and cells are seeded in cell culture flasks in DMEM-F12, RPMI, and Alpha-MEM medium supplemented with 10% fetal bovine serum and 1% antibiotics under standard culture conditions. For example, Hassiotou et al. (2012, Stem Cells. 30(10): 2164-2174), which is incorporated herein by reference in its entirety for all purposes, describes certain variation(s) of the method(s) described herein in this example.

Differentiation of Stem Cells Using 2D and 3D Culture Systems

The mesenchymal cells isolated from adipose tissue of different animals or from milk as described above can be differentiated into mammary-like epithelial and luminal cells in 2D and 3D culture systems. See, for example, Huynh et al. 1991. Exp Cell Res. 197(2): 191-199; Gibson et al. 1991, In Vitro Cell Dev Biol Anim. 27(7): 585-594; Blatchford et al. 1999; Animal Cell Technology': Basic & Applied Aspects, Springer, Dordrecht. 141-145; Williams et al. 2009, Breast Cancer Res 11(3): 26-43; and Arevalo et al. 2015, Am J Physiol Cell Physiol. 310(5): C348-C356; each of which is incorporated herein by reference in their entireties for all purposes.

For 2D culture, the isolated cells were initially seeded in culture plates in growth media supplemented with 10 ng/mL epithelial growth factor and 5 pg/mL insulin. At confluence, cells were fed with growth medium supplemented with 2% fetal bovine serum, 1% penicillin-streptomycin (100 U/mL penicillin, 100 ug/mL streptomycin), and 5 pg/mL insulin for 48h. To induce differentiation, the cells were fed with complete growth medium containing 5 pg/mL insulin, 1 pg/mL hydrocortisone, 0.65 ng/mL triiodothyronine, 100 nM dexamethasone, and 1 pg/mL prolactin. After 24h, serum is removed from the complete induction medium.

For 3D culture, the isolated cells were trypsinized and cultured in Matrigel, hyaluronic acid, or ultra-low attachment surface culture plates for six days and induced to differentiate and lactate by adding growth media supplemented with 10 ng/mL epithelial growth factor and 5 pg insulin. At confluence, cells were fed with growth medium supplemented with 2% fetal bovine serum, 1% penicillin-streptomycin (100 U/mL penicillin, 100 pg streptomycin), and 5 pg insulin for 48h. To induce differentiation, the cells were fed with complete growth medium containing 5 pg insulin, 1 pg hydrocortisone, 0.65 ng/mL triiodothyronine, 100 nM dexamethasone, and 1 pg prolactin. After 24h, serum is removed from the complete induction medium.

Method of Making Mammary-Like Cells

In a next step, the cells are brought to induced pluripotency by reprogramming with viral vectors encoding for Oct4, Sox2, Klf4, and c-Myc. The resultant reprogrammed cells are then cultured in Mammocult media (available from Stem Cell Technologies), or mammary cell enrichment media (DMEM, 3% FBS, estrogen, progesterone, heparin, hydrocortisone, insulin, EGF) to make them mammary-like, from which expression of select milk components can be induced. Alternatively, epigenetic remodeling is performed using remodeling systems such as CRISPR/Cas9, to activate select genes of interest, such as casein, a-lactalbumin to be constitutively on, to allow for the expression of their respective proteins, and/or to down-regulate and/or knock-out select endogenous genes as described e.g., in WO21067641, which is incorporated herein by reference in its entirety for all purposes.

Cultivation

Completed growth media includes high glucose DMEM/F12, 10% FBS, 1% NEAA, 1% pen/strep, 1% ITS-X, 1% F-Glu, 10 ng/mL EGF, and 5 pg/mL hydrocortisone. Completed lactation media includes high glucose DMEM/F12, 1% NEAA, 1% pen/strep, 1% ITS-X, 1% F-Glu, 10 ng/mL EGF, 5 pg/mL hydrocortisone, and 1 pg/mL prolactin (5 ug/mL in Hyunh 1991). Cells are seeded at a density of 20,000 cells/cm2 onto collagen coated flasks in completed growth media and left to adhere and expand for 48 hours in completed growth media, after which the media is switched out for completed lactation media. Upon exposure to the lactation media, the cells start to differentiate and stop growing. Within about a week, the cells start secreting lactation product(s) such as milk lipids, lactose, casein and whey into the media. A desired concentration of the lactation media can be achieved by concentration or dilution by ultrafiltration. A desired salt balance of the lactation media can be achieved by dialysis, for example, to remove unwanted metabolic products from the media. Hormones and other growth factors used can be selectively extracted by resin purification, for example, the use of nickel resins to remove His-tagged growth factors, to further reduce the levels of contaminants in the lactated product.

G. Optical Density

Cell density of the cultures was frequently monitored by measuring optical density at 600 nm (Implen Nanophotometer NP80, Westburg, Belgium or with a Spark 10M microplate reader, Tecan, Switzerland). The maximum growth speed (mumax) was calculated based on the observed optical densities at 600 nm using the R package grofit.

H. Heterologous and Homologous Expression

Genes that needed to be expressed, be it from a plasmid or from the genome were synthetically synthetized with one of the following companies: IDT, Twist Bioscience, DNA2.0 or Gen9. Proteins described in present disclosure are summarized in Table 1. Unless stated otherwise, the UniProt IDs of the proteins described correspond to their sequence version 01 as present in the UniProt Database version release 2021_03 of 9 Jun. 2021. Expression could be further facilitated by optimizing the codon usage to the codon usage of the expression host. Genes were optimized using the tools of the supplier.

TABLE 1

Overview of proteins with corresponding SEQ ID NOs or UniProt IDs (sequence version 01, UniProt Database 2021_03 of 9 Jun. 2021) as described herein

| SEQ ID NO | Name | Organism | Origin | Country of origin of digital sequence information |
|---|---|---|---|---|
| 01 | a23-ST | Streptococcus acidominimus | Synthetic | Unknown |
| 02 | a23-ST | Streptococcus azizii | Synthetic | USA |
| 03 | a23-ST | Helicobacter mustelae 12198 | Synthetic | USA |
| 04 | a23-ST | Actinobacillus vicugnae strain W16181 | Synthetic | United Kingdom |
| 05 | a23-ST | Glaesserella australis strain HS4635 | Synthetic | Australia |
| 06 | a23-ST | Vespertiliibacter pulmonis | Synthetic | Germany |
| 07 | a23-ST | Streptococcus agalactiae 7271 (VII) | Synthetic | Unknown |
| 08 | a23-ST | Streptococcus agalactiae 2603V/R | Synthetic | Unknown |
| 09 | neuA | Pasteurella multocida | Synthetic | USA |
| 10 | glmS*54 | Escherichia coli K-12 MG1655 | Synthetic | USA |

TABLE 1-continued

Overview of proteins with corresponding SEQ ID NOs or UniProt IDs (sequence version 01, UniProt Database 2021_03 of 9 Jun. 2021) as described herein

| SEQ ID NO | Name | Organism | Origin | Country of origin of digital sequence information |
|---|---|---|---|---|
| 11 | a23-ST | Pasteurella multocida | Synthetic | USA |
| 12 | a23-ST | Avibacterium paragallinarum | Synthetic | USA |
| 13 | GNE | Homo sapiens | Synthetic | Unknown |
| 14 | a23-ST | Neisseria meningitidis MC58 | Synthetic | United Kingdom |
| 15 | a23-ST | Neisseria gonorrhoeae | Synthetic | Unknown |
| Q9CLP3 | a23-ST | Pasteurella multocida | Synthetic | USA |
| P27550[a] | acs | Escherichia coli K-12 MG1655 | Synthetic | USA |
| A7LVG6 | AGE | Bacteroides ovatus | Synthetic | USA |
| A0ZZH6 | BaSP | Bifidobacterium adolescentis | Synthetic | Germany |
| B7GPD4 | Blon 2475 | Bifidobacterium longum subsp. infantis | Synthetic | Germany |
| Q8NFW8[b] | CMAS | Homo sapiens | Synthetic | Unknown |
| E0IXR1 | cscB | Escherichia coli W | Synthetic | USA |
| Q61420 | CST | Mus musculus | Synthetic | USA |
| P24077[c] | entS | Escherichia coli K-12 MG1655 | Synthetic | USA |
| A0A378GQ13 | entS | Kluyvera ascorbata | Synthetic | USA |
| A0A6Y2K4E8 | entS | Salmonella enterica subsp. arizonae | Synthetic | USA |
| Q03417 | Frk | Zymomonas mobilis | Synthetic | United Kingdom |
| Q06210[d] | GFPT1 | Homo sapiens | Synthetic | Unknown |
| P31120[e] | glmM | Escherichia coli K-12 MG1655 | Synthetic | USA |
| P17169[f] | glmS | Escherichia coli K-12 MG1655 | Synthetic | USA |
| P0CI73 | glmS | Bacillus subtilis | Synthetic | USA |
| Q8NND3[g] | glmS | Corynebacterium glutamicum | Synthetic | USA |
| P0ACC7 | glmU | Escherichia coli K-12 MG1655 | Synthetic | USA |
| Q96EK6 | GNA1 | Homo sapiens | Synthetic | Unknown |
| P43577 | GNA1 | Saccharomyces cerevisiae | Synthetic | USA |
| Q9Y223 | GNE | Homo sapiens | Synthetic | Unknown |
| Q91WG8 | GNE | Mus musculus (strain C57BL/6J) | Synthetic | USA |
| D4B8A6 | iceT | Citrobacter youngae | Synthetic | USA |
| A0A024L207 | iceT | Escherichia coli K-12 MG1655 | Synthetic | USA |
| Q9SEE5 | KIN | Arabidopsis thaliana | Synthetic | USA |
| P07921 | LAC12 | Kluyveromyces lactis | Synthetic | USA |
| P02920 | LacY | Escherichia coli K-12 MG1655 | Synthetic | USA |
| A0A1V0NEL4 | lmrA | Lactococcus lactis subsp. lactis bv. diacetylactis | Synthetic | Serbia |
| D4BC23 | MdfA | Citrobacter youngae | Synthetic | USA |
| A0A2T7ANQ9 | MdfA | Cronobacter muytjensii | Synthetic | USA |
| P0AEY8 | MdfA | Escherichia coli K-12 MG1655 | Synthetic | USA |
| G9Z5F4 | MdfA | Yokenella regensburgei | Synthetic | Unknown |
| KPA15328.1 | NANP | Candidatus Magnetomorum sp. HK-1 | Synthetic | Germany |
| Q8A712 | NANP | Bacteroides thetaiotaomicron | Synthetic | Unknown |
| Q9NR45[h] | NANS | Homo sapiens | Synthetic | Unknown |
| K9NPH9 | NANS | Pseudomonas sp. UW4 | Synthetic | Unknown |
| B1EFH1 | nanT | Escherichia albertii | Synthetic | USA |
| P41036[i] | nanT | Escherichia coli K-12 MG1655 | Synthetic | USA |
| Q8FD59 | nanT | Escherichia coli O6:H1 | Synthetic | USA |
| Q99KK2[j] | neuA | Mus musculus | Synthetic | USA |
| E0NCD4 | neuB | Neisseria meningitidis | Synthetic | United Kingdom |
| Q93MP9 | neuB | Campylobacter jejuni | Synthetic | USA |
| Q93MP8 | neuC | Campylobacter jejuni | Synthetic | USA |
| P77737 | oppF | Escherichia coli K-12 MG1655 | Synthetic | USA |
| O95394 | PGM3 | Homo sapiens | Synthetic | Unknown |
| Q9CLP3 | PmultST3 | Pasteurella multocida | Synthetic | USA |
| A0A078LM16 | SetA | Citrobacter koseri | Synthetic | Unknown |
| P31675[k] | SetA | Escherichia coli K-12 MG1655 | Synthetic | USA |
| P33026 | SetB | Escherichia coli K-12 MG1655 | Synthetic | USA |
| P31436 | SetC | Escherichia coli K-12 MG1655 | Synthetic | USA |
| P0A840 | surE | E. coli K-12 MG1655 | Synthetic | USA |
| Q16222[l] | UAP1 | Homo sapiens | Synthetic | Unknown |
| Q9C511 | USP | Arabidopsis thaliana | Synthetic | USA |

[a]Sequence version 02 (1 Oct. 1993) as present in the UniProt Database 2021_03 of 9 Jun. 2021
[b]Sequence version 02 (1 Feb. 2005) as present in the UniProt Database 2021_03 of 9 Jun. 2021
[c]Sequence version 02 (1 Nov. 1997) as present in the UniProt Database 2021_03 of 9 Jun. 2021
[d]Sequence version 03 (10 Feb. 2009) as present in the UniProt Database 2021_03 of 9 Jun. 2021
[e]Sequence version 03 (23 Jan. 2007) as present in the UniProt Database 2021 03 of 9 Jun. 2021
[f]Sequence version 04 (23 Jan. 2007) as present in the UniProt Database 2021_03 of 9 Jun. 2021
[g]Sequence version 02 (23 Jan. 2007) as present in the UniProt Database 2021_03 of 9 Jun. 2021
[h]Sequence version 03 (13 Oct. 2009) as present in the UniProt Database 2021 03 of 9 Jun. 2021
[i]Sequence version 02 (1 Nov. 1995) as present in the UniProt Database 2021 03 of 9 Jun. 2021
[j]Sequence version 02 (1 Feb. 2005) as present in the UniProt Database 2021_03 of 9 Jun. 2021
[k]Sequence version 03 (11 Oct. 2004) as present in the UniProt Database 2021_03 of 9 Jun. 2021
[l]Sequence version 03 (5 Jul. 2005) as present in the UniProt Database 2021_03 of 9 Jun. 2021

I. Analytical Analysis

Standards such as but not limited to sucrose, lactose, 3'SL and 6'SL were purchased from Carbosynth (UK), Elicityl (France) and IsoSep (Sweden). Other compounds were analyzed with in-house made standards.

Neutral oligosaccharides were analyzed on a Waters Acquity H-class UPLC with Evaporative Light Scattering Detector (ELSD) or a Refractive Index (RI) detection. A volume of 0.7 µL sample was injected on a Waters Acquity UPLC BEH Amide column (2.1×100 mm; 130 Å; 1.7 µm) column with an Acquity UPLC BEH Amide VanGuard column, 130 Å, 2.1×5 mm. The column temperature was 50° C. The mobile phase consisted of a ¼ water and ¾ acetonitrile solution to which 0.2% triethylamine was added. The method was isocratic with a flow of 0.130 mL/min. The ELS detector had a drift tube temperature of 50° C. and the N2 gas pressure was 50 psi, the gain 200 and the data rate 10 pps. The temperature of the RI detector was set at 35° C.

Sialylated oligosaccharides were analyzed on a Waters Acquity H-class UPLC with Refractive Index (RI) detection. A volume of 0.5 µL sample was injected on a Waters Acquity UPLC BEH Amide column (2.1×100 mm; 130 Å; 1.7 µm). The column temperature was 50° C. The mobile phase consisted of a mixture of 70% acetonitrile, 26% ammonium acetate buffer (150 mM) and 4% methanol to which 0.05% pyrrolidine was added. The method was isocratic with a flow of 0.150 mL/min. The temperature of the RI detector was set at 35° C.

Both neutral and sialylated sugars were analyzed on a Waters Acquity H-class UPLC with Refractive Index (RI) detection. A volume of 0.5 µL sample was injected on a Waters Acquity UPLC BEH Amide column (2.1×100 mm; 130 Å; 1.7 µm). The column temperature was 50° C. The mobile phase consisted of a mixture of 72% acetonitrile and 28% ammonium acetate buffer (100 mM) to which 0.1% triethylamine was added. The method was isocratic with a flow of 0.260 mL/min. The temperature of the RI detector was set at 35° C.

For analysis on a mass spectrometer, a Waters Xevo TQ-MS with Electron Spray Ionization (ESI) was used with a desolvation temperature of 450° C., a nitrogen desolvation gas flow of 650 L/h and a cone voltage of 20 V. The MS was operated in selected ion monitoring (SIM) in negative mode for all oligosaccharides. Separation was performed on a Waters Acquity UPLC with a Thermo Hypercarb column (2.1×100 mm; 3 µm) on 35° C. A gradient was used wherein eluent A was ultrapure water with 0.1% formic acid and wherein eluent B was acetonitrile with 0.1% formic acid. The oligosaccharides were separated in 55 min using the following gradient: an initial increase from 2 to 12% of eluent B over 21 min, a second increase from 12 to 40% of eluent B over 11 min and a third increase from 40 to 100% of eluent B over 5 min. As a washing step 100% of eluent B was used for 5 min. For column equilibration, the initial condition of 2% of eluent B was restored in 1 min and maintained for 12 min.

Both neutral and sialylated sugars at low concentrations (below 50 mg/L) were analyzed on a Dionex HPAEC system with pulsed amperometric detection (PAD). A volume of 5 µL of sample was injected on a Dionex CarboPac PA200 column 4×250 mm with a Dionex CarboPac PA200 guard column 4×50 mm. The column temperature was set to 30° C. A gradient was used wherein eluent A was deionized water, wherein eluent B was 200 mM Sodium hydroxide and wherein eluent C was 500 mM Sodium acetate. The oligosaccharides were separated in 60 min while maintaining a constant ratio of 25% of eluent B using the following gradient: an initial isocratic step maintained for 10 min of 75% of eluent A, an initial increase from 0 to 4% of eluent C over 8 min, a second isocratic step maintained for 6 min of 71% of eluent A and 4% of eluent C, a second increase from 4 to 12% of eluent C over 2.6 min, a third isocratic step maintained for 3.4 min of 63% of eluent A and 12% of eluent C and a third increase from 12 to 48% of eluent C over 5 min. As a washing step 48% of eluent C was used for 3 min. For column equilibration, the initial condition of 75% of eluent A and 0% of eluent C was restored in 1 min and maintained for 11 min. The applied flow was 0.5 mL/min.

J. Protein Quantification

For protein quantification a method is used that is compatible with reducing agents, such as reducing sugars or oligosaccharides with a reducing end. To this end, a Bradford assay (Thermo Scientific, Pierce) was used with a linear range between 1 and 1500 µg/mL. The assay was calibrated with a standard curve of BSA. The protein content of dried oligosaccharide products was quantified by dissolving a pre-weighed quantify in 18.2 Ma cm (Millipore, Bedford, MA, USA) de-ionized water (DIW) up to a quantity of 50% (m/v). The amount of protein is measured at 595 nm and converted to concentration with the calibration curve based on BSA.

K. DNA Quantification

Production host specific DNA residue is quantified by RT-qPCR, for which specific primers on the host are designed so that residual DNA of the production host is amplified. The RT-qPCR was performed according to the standard protocol of a kit obtained from Sigma and was based on SYBR Green detection.

Total DNA is measured by means of a Threshold assay (Molecular Devices), based on an immunoassay allowing to measure as low as 2 pg of DNA in a sample in solution. Double stranded DNA is measured by means of SPECTRA-MAX® QUANT™ ACCUBLUE™ Pico dsDNA Assay Kit (Molecular Devices) having a linear range between 5 pg and 3 ng of dsDNA.

Example 3. Production of 3'SL with a Modified *E. coli* Host

An *E. coli* K-12 MG1655 strain modified for production of sialic acid comprising genomic knock-ins of constitutive transcriptional units containing the mutant glmS*54 from *E. coli* with SEQ ID NO:10 (differing from the wild-type *E. coli* glmS, having UniProt ID P17169 (sequence version 04 (23 Jan. 2007), by an A39T, an R250C and an G472S mutation as described by Deng et al. (Biochimie 88, 419-29 (2006)), the glucosamine 6-phosphate N-acetyltransferase GNA1 from *S. cerevisiae* (UniProt ID P43577), the N-acyl-glucosamine 2-epimerase AGE from *B. ovatus* (UniProt ID A7LVG6) and the N-acetylneuraminate synthase NeuB from *N. meningitidis* (UniProt ID E0NCD4) and modified for growth on sucrose as described in Example 2 was further transformed with an expression plasmid containing a constitutive transcriptional unit for the N-acylneuraminate cytidylyltransferase neuA from *P. multocida* with SEQ ID NO:09 and for i) a sialyltransferase with SEQ ID NOs:01, 02, 03, 04, 05, 06, 07, 08 or 12 or ii) a PmultST3-like polypeptide with SEQ ID NO:11 consisting of amino acid residues 1 to 268 of UniProt ID Q9CLP3 having beta-galactoside alpha-2,3-sialyltransferase activity acting as a reference alpha-2,3-sialyltransferase. The novel strains were evaluated in a growth experiment for production of 3'SL (Neu5Ac-a2,3-Gal-b1,4-Glc) according to the culture conditions provided in Example 2, in which the strains were cultivated in minimal medium with 30 g/L sucrose and 20 g/L lactose. The strains were grown in four biological replicates in a 96-well plate. After 72h of incubation, the culture broth was harvested, and the sugars were analyzed on UPLC. For each strain with a particular sialyltransferase tested, the measured 3'SL concentration and maximum growth speed was averaged over all biological replicates and then normalized to the averaged 3'SL concentration or maximum growth speed of a reference strain expressing a PmultST3-like polypeptide with SEQ ID NO:11 consisting of amino acid residues 1 to 268 of UniProt ID Q9CLP3 having beta-galactoside alpha-2,3-sialyltransferase activity. The experiment showed all sialyltransferases were able to produce 3'SL. Surprisingly, and as demonstrated in Table 2, the sialyltransferases with SEQ ID NOs:01, 02, 03, 04, 05, 06, 07, 08 or 12 had a better 3-sialyltransferase binding activity on lactose than the reference PmultST3-like polypeptide with SEQ ID NO:11 consisting of amino acid residues 1 to 268 of UniProt ID Q9CLP3 having beta-galactoside alpha-2,3-sialyltransferase activity. The experiment also showed that strains expressing a sialyltransferase with SEQ ID NOs:01, 02, 03, 04, 05, 06, 07, 08 or 12 had a higher maximum growth speed compared to the reference strain expressing the reference PmultST3-like polypeptide with SEQ ID NO:11 consisting of amino acid residues 1 to 268 of UniProt ID Q9CLP3 having beta-galactoside alpha-2,3-sialyltransferase activity (Table 2).

TABLE 2

Relative production of 3 'SL (%) in and relative maximum growth speed (%) of a modified *E. coli* strain expressing a sialyltransferase with SEQ ID NOs: 01, 02, 03, 04, 05, 06, 07, 08 or 12 and compared to a reference strain expressing a PmultST3-like polypeptide with SEQ ID NO: 11 consisting of amino acid residues 1 to 268 of UniProt ID Q9CLP3, when evaluated in a growth experiment according to the culture conditions provided in Example 2, in which the culture medium contained 30 g/L sucrose and 20 g/L lactose.

| Strain | Sialyltransferase expressed | 3'SL (%) | mumax (%) |
|---|---|---|---|
| A | PmultST3-like polypeptide with SEQ ID NO: 11 consisting of amino acid residues 1 to 268 of UniProt ID Q9CLP3 | 100 | 100 |
| B | SEQ ID NO: 01 | 236 | 134 |
| C | SEQ ID NO: 02 | 220 | 136 |
| D | SEQ ID NO: 03 | 180 | 128 |
| E | SEQ ID NO: 04 | 277 | 136 |
| F | SEQ ID NO: 05 | 287 | 134 |
| G | SEQ ID NO: 06 | 302 | 126 |
| H | SEQ ID NO: 07 | 235 | 136 |
| I | SEQ ID NO: 08 | 205 | 131 |
| J | SEQ ID NO: 12 | 118 | 107 |

Example 4. Production of 3'SL with a Modified *E. coli* Host

An *E. coli* K-12 MG1655 strain containing a knock-out of the *E. coli* lacZ gene is further transformed with an expression plasmid containing a constitutive transcriptional unit for the N-acylneuraminate cytidylyltransferase neuA from *P. multocida* with SEQ ID NO:09 and for a sialyltransferase with SEQ ID NOs:01, 02, 03, 04, 05, 06, 07, 08 or 12. The novel strains are evaluated in a growth experiment for production of 3'SL according to the culture conditions provided in Example 2, in which the strains are cultivated in minimal medium with glycerol as carbon source and sialic acid and lactose added to the medium. After 72h of incubation, the culture broth is harvested, and the sugars are analyzed on UPLC.

Example 5. Production of 3'SL with a Modified *E. coli* Host

An *E. coli* K-12 MG1655 strain containing a knock-out of the *E. coli* lacZ gene is further modified for growth on sucrose as described in Example 2. Next, the strain is transformed with an expression plasmid containing a constitutive transcriptional unit for the N-acylneuraminate cytidylyltransferase neuA from *P. multocida* with SEQ ID NO:09 and for a sialyltransferase with SEQ ID NOs:01, 02, 03, 04, 05, 06, 07, 08, or 12. The novel strains are evaluated in a growth experiment for production of 3'SL according to the culture conditions provided in Example 2, in which the strains are cultivated in minimal medium with sucrose as carbon source and sialic acid and lactose added to the medium. After 72h of incubation, the culture broth is harvested, and the sugars are analyzed on UPLC.

Example 6. Production of 3'SL with Modified *E. coli* Hosts when Evaluated in a Fed-Batch Fermentation Process with Sucrose and Lactose The modified *E. coli* strains expressing a sialyltransferase with SEQ ID NOs:1, 2, 3, 4, 5, 6, 7, 8, or 12 as described in Example 3 are selected for further evaluation in a fed-batch fermentation process. Fed-batch fermentations at bioreactor scale are performed as described in Example 2. Sucrose was used as a carbon source and lactose was added in the batch medium. During fed-batch, sucrose was added via an additional feed. In contrast to the cultivation experiments that are described herein and wherein only end samples were taken at the end of cultivation (i.e., 72 hours as described herein), regular broth samples were taken at several time points during the fermentation process and the 3'SL produced was measured using UPLC as described in Example 2. At the end of the fermentations, the percentage of lactose on total sugar was <10%, the percentage of sialic acid on total sugar was <5%, the percentage of sucrose was 0% and the percentage of 3'SL on total sugar was >85%.

Example 7. Evaluation of Alpha-2,3-Sialyltransferase Activity In Vitro

Another example provides the evaluation of alpha-2,3-sialyltransferase activity of the enzymes with SEQ ID NOs: 1, 2, 3, 4, 5, 6, 7, 8, or 12 in an in vitro enzymatic assay. The enzyme can be produced in a cell-free expression system such as but not limited to the PURExpress system (NEB), or in a host organism such as but not limited to *Escherichia coli* or *Saccharomyces cerevisiae*, after which the enzyme can be isolated and optionally further purified. The enzyme extract or purified enzyme is added to a reaction mixture together with CMP-sialic acid and a buffering component such as Tris-HCl or HEPES and a substrate like e.g., lactose. The reaction mixture is then incubated at a certain temperature (for example, 37° C.) for a certain amount of time (for example, 8 hours, 16 hours, 24 hours), during which the lactose will be converted by the enzyme using CMP-sialic acid to 3'SL. The 3'SL is then separated from the reaction mixture by methods known in the art. Further purification of 3'SL can be performed if preferred. At the end of the reaction or after separation and/or purification, the production of 3'SL is measured via analytical methods as described in Example 2 and known by the person skilled in the art.

Example 8. Production of 3'SL with a Modified *S. cerevisiae* Host

A *S. cerevisiae* strain is modified for production of CMP-sialic acid and for expression of a sialyltransferase as described in Example 2 with a yeast expression plasmid comprising constitutive transcriptional units for LAC12 from *K. lactis* (UniProt ID P07921), the mutant glmS*54 from *E. coli* with SEQ ID NO:10 (differing from the wild-type *E. coli* glmS, having UniProt ID P17169 (sequence version 04 (23 Jan. 2007), by an A39T, an R250C and an G472S mutation as described by Deng et al. (Biochimie 88, 419-29 (2006)), the phosphatase SurE from *E. coli* (UniProt ID P0A840), AGE from *B. ovatus* (UniProt ID A7LVG6), NeuB from *N. meningitidis* (UniProt ID E0NCD4), NeuA from *P. multocida* with SEQ ID NO:09, and a sialyltransferase with SEQ ID NOs:1, 2, 3, 4, 5, 6, 7, 8, or 12. The novel strains are evaluated for production of 3'SL when evaluated in a 3-days growth experiment according to the culture conditions provided in Example 2 using appropriate selective medium comprising lactose.

Example 9. Production of 3'SL with a Modified *B. subtilis* Host

A wild-type *B. subtilis* strain is first modified with genomic knockouts of the *B. subtilis* genes nagA, nagB and gamA together with genomic knock-ins of constitutive transcriptional units for the N-acylglucosamine 2-epimerase AGE from *B. ovatus* (UniProt ID A7LVG6), the N-acetylneuraminate synthase NeuB from *N. meningitidis* (UniProt ID E0NCD4) and the lactose permease LacY from *E. coli* (UniProt ID P02920) as described in Example 2. In a next step, the modified *B. subtilis* strain is transformed with an expression plasmid comprising constitutive transcriptional units for the N-acylneuraminate cytidylyltransferase neuA from *P. multocida* (SEQ ID NO:09) and a sialyltransferase with SEQ ID NOs:1, 2, 3, 4, 5, 6, 7, 8 or 12. The novel strains are evaluated for production of 3'SL when evaluated in a 3-days growth experiment according to the culture conditions provided in Example 2 using appropriate selective medium comprising lactose.

Example 10. Production of 3'SL with a Modified *C. glutamicum* Host

A wild-type *C. glutamicum* strain is first modified with genomic knockouts of the ldh, cgl2645 and nagB genes together with genomic knock-ins of constitutive transcriptional units for the phosphoglucosamine mutase glmM from *E. coli* (UniProt ID P31120, sequence version 03 (23 Jan. 2007)), the N-acetylglucosamine-1-phosphate uridylyltransferase/glucosamine-1-phosphate acetyltransferase glmU from *E. coli* (UniProt ID P0ACC7), the UDP-N-acetylglucosamine 2-epimerase neuC from *C. jejuni* (UniProt ID Q93MP8), the N-acetylneuraminate synthase neuB from *N. meningitidis* (UniProt ID E0NCD4) and the lactose permease LacY from *E. coli* (UniProt ID P02920). In a next step, the modified *C. glutamicum* strain is transformed with an expression plasmid comprising constitutive transcriptional units for the N-acylneuraminate cytidylyltransferase neuA from *P. multocida* (SEQ ID NO:09) and a sialyltransferase with SEQ ID NOs:1, 2, 3, 4, 5, 6, 7, 8, or 12. The novel strains are evaluated for production of 3'SL when evaluated in a 3-days growth experiment according to the culture conditions provided in Example 2 using appropriate selective medium comprising lactose.

Example 11. Production of 3'SL with Modified *C. reinhardtii* Cells

*C. reinhardtii* cells are engineered as described in Example 2 with genomic knock-ins of constitutive transcriptional units comprising the galactokinase from *A. thaliana* (KIN, UniProt ID Q9SEE5) and the UDP-sugar pyrophosphorylase (USP) from *A. thaliana* (UniProt ID Q9C5I1). In a next step, the engineered cells are modified for CMP-sialic acid synthesis with genomic knock-ins of constitutive transcriptional units comprising a mutant form of the UDP-N-acetylglucosamine-2-epimerase/N-acetylmannosamine kinase GNE from *Homo sapiens* with SEQ ID NO:13 differing from the native polypeptide (UniProt ID Q9Y223) with a R263L mutation, the N-acylneuraminate-9-phosphate synthetase NANS from *H. sapiens* (UniProt ID Q9NR45, sequence version 03 (13 Oct. 2009)), the N-acylneuraminate cytidylyltransferase CMAS from *Homo sapiens* (UniProt ID Q8NFW8, sequence version 02 (1 Feb. 2005)) and the CMP-sialic acid transporter CST from *Mus musculus* (UniProt ID Q61420). In a final step, the engineered cells are modified with an expression plasmid comprising constitutive transcriptional units comprising a sialyltransferase with SEQ ID NOs:1, 2, 3, 4, 5, 6, 7, 8, or 12. The novel strains are evaluated for production of 3'SL in a cultivation experiment on TAP-agar plates comprising galactose, glucose and GlcNAc as precursors according to the culture conditions provided in Example 2. After 5 days of incubation, the cells are harvested, and the saccharide production is analyzed on UPLC.

Example 12. Production of 3'SL with Non-Mammary Adult Stem Cells

Isolated mesenchymal cells and re-programmed into mammary-like cells as described in Example 2 are modified via CRISPR-CAS to express the GlcN6P synthase from *Homo sapiens* (UniProt ID Q06210, sequence version 03 (10 Feb. 2009)), the glucosamine 6-phosphate N-acetyltransferase from *H. sapiens* (UniProt ID Q96EK6), the phosphoacetylglucosamine mutase from *H. sapiens* (UniProt ID O95394), the UDP-N-acetylhexosamine pyrophosphorylase from *H. sapiens* (UniProt ID Q16222, sequence version 03 (5 Jul. 2005)), the N-acylneuraminate cytidylyltransferases neuA from *Mus musculus* (UniProt ID Q99KK2, sequence version 02 (1 Feb. 2005)) and a sialyltransferase with SEQ ID NOs:1, 2, 3, 4, 5, 6, 7, 8, or 12. Cells are seeded at a density of 20,000 cells/cm2 onto collagen coated flasks in completed growth media and left to adhere and expand for 48 hours in completed growth media, after which the media is switched out for completed lactation media for about 7 days. After cultivation as described in Example 2, cells are subjected to UPLC to analyze for production of 3'SL.

Example 13. Production of 3'SL with a Modified *E. coli* Host

An *E. coli* K-12 MG1655 strain modified for production of sialic acid comprising genomic knock-ins of constitutive transcriptional units containing the mutant glmS*54 from *E. coli* with SEQ ID NO:10, the glucosamine 6-phosphate N-acetyltransferase GNA1 from *S. cerevisiae* (UniProt ID P43577), the N-acylglucosamine 2-epimerase AGE from *B. ovatus* (UniProt ID A7LVG6) and the N-acetylneuraminate synthase NeuB from *N. meningitidis* (UniProt ID E0NCD4) and modified for growth on sucrose as described in Example 2 was further modified with genomic knock-ins of constitutive transcriptional units containing the alpha-2,3-sialyltransferase PmultST3-like polypeptide from *P. multocida* with SEQ ID NO:11 consisting of amino acid residues 1 to 268 of UniProt ID Q9CLP3 having beta-galactoside alpha- 2,3-sialyltransferase activity and the alpha-2,3-sialyltransferase AparaST from *A. paragallinarum* (SEQ ID NO:12). In a next step, the strain was either transformed with an expression plasmid containing a constitutive transcriptional unit for the N-acylneuraminate cytidylyltransferase neuA from *P. multocida* with SEQ ID NO:9 and for the alpha-2,3-sialyltransferase PmultST3-like polypeptide from *P. multocida* with SEQ ID NO:11 or with an expression plasmid containing a constitutive transcriptional unit for the N-acylneuraminate cytidylyltransferase neuA from *P. multocida* with SEQ ID NO:09 and for the alpha-2,3-sialyltransferase from *Glaesserella australis* strain HS4635 with SEQ ID NO:5. The novel strains were evaluated in a growth experiment for production of 3'SL according to the culture conditions provided in Example 2, in which the strains were cultivated in minimal medium with sucrose as carbon source and lactose added to the medium. After 72h of incubation, the culture broth was harvested, and the production of 3'SL was analyzed on UPLC.

Example 14. Production of 3'KDO-Lactose with a Modified *E. coli* Host

An *E. coli* K-12 MG1655 strain containing a knock-out of the *E. coli* lacZ gene is further modified for growth on sucrose as described in Example 2. Next, the strain is transformed with an expression plasmid containing a constitutive transcriptional unit for the N-acylneuraminate cytidylyltransferase neuA from *P. multocida* with SEQ ID NO:09 and for a sialyltransferase with SEQ ID NOs:01, 02, 03, 04, 05, 06, 07, 08, or 12. The novel strains are evaluated in a growth experiment for production of 3'KDO-lactose according to the culture conditions provided in Example 2, in which the strains are cultivated in minimal medium with sucrose as carbon source and sialic acid and lactose added to the medium. After 72h of incubation, the culture broth is harvested, and the sugars are analyzed on UPLC.

Example 15. Production of a Saccharide Mixture Comprising 3'SL and 3'KDO-Lactose with a Modified *E. Coli* Host An *E. coli* strain modified for sialic acid production as described in Example 2 was transformed with an expression plasmid comprising a constitutive transcriptional unit for the membrane protein entS from *Kluyvera ascorbata* (UniProt ID A0A378GQ13), the N-acylneuraminate cytidylyltransferase NeuA from *P. multocida* (SEQ ID NO:09) and an alpha-2,3-sialyltransferase selected from the list comprising SEQ ID NOs:1, 2, 4, 5, 6, 8, and 11. The novel strains were evaluated in a fed-batch fermentation process. Fed-batch fermentations at bioreactor scale were performed as described in Example 2. Sucrose was used as a carbon source and lactose was added in the batch medium. During fed-batch, sucrose was added via an additional feed. In contrast to the cultivation experiments that are described herein and wherein only end samples were taken at the end of cultivation (i.e., 72 hours as described herein), regular broth samples were taken at several time points during the fermentation process and the 3'SL and 3'-KDO-lactose produced were measured using UPLC as described in Example 2. For each strain with a particular sialyltransferase tested, the measured 3'SL concentration and 3'KDO-lactose concentration were averaged over all biological replicates and then normalized to the averaged 3'SL concentration and 3'KDO-lactose concentration measured of a reference strain with identical genetic make-up as the tested strains but expressing a PmultST3-like polypeptide with SEQ ID NO:11, consisting of amino acid residues 1 to 268 of UniProt ID Q9CLP3 having beta-galactoside alpha-2,3-sialyltransferase activity. The experiment showed all strains were able to produce a saccharide mixture comprising 3'SL and 3'-KDO-lactose. Table 3 demonstrates the ratio of 3'KDO-lactose produced over the 3'SL produced in a particular strain to be lower than 0.1 for all strains.

TABLE 3

Ratio of 3 'KDO-lactose produced over 3 'SL in a modified *E. coli* strain expressing a sialyltransferase with SEQ ID NOs: 1, 2, 4, 5, 6, 8, or 11 when evaluated in a fed-batch fermentation process according to the culture conditions provided in Example 2, in which the batch medium contained in sucrose and lactose, and in which sucrose was added in an additional feed during fed-batch.

| Strain | Sialyltransferase expressed | Ratio 3'KDO-lactose/3'SL |
|---|---|---|
| A | PmultST3-like polypeptide with SEQ ID NO: 11 consisting of amino acid residues 1 to 268 of UniProt ID Q9CLP3 | 0.00125 |
| B | SEQ ID NO: 01 | 0.022 |
| C | SEQ ID NO: 02 | 0.0014 |
| E | SEQ ID NO: 04 | 0.0039 |
| F | SEQ ID NO: 05 | 0.0017 |
| G | SEQ ID NO: 06 | 0.0108 |
| I | SEQ ID NO: 08 | 0.071 |

Example 16. Production of 3'SL with a Modified *E. coli* Host

An *E. coli* K-12 MG1655 strain modified for production of sialic acid comprising genomic knock-ins of constitutive transcriptional units containing the mutant glmS*54 from *E. coli* with SEQ ID NO:10 (differing from the wild-type *E. coli* glmS, having UniProt ID P17169 (sequence version 04 (23 Jan. 2007), by an A39T, an R250C and an G472S mutation as described by Deng et al. (Biochimie 88, 419-29 (2006)), the glucosamine 6-phosphate N-acetyltransferase GNA1 from *S. cerevisiae* (UniProt ID P43577), the N-acylglucosamine 2-epimerase AGE from *B. ovatus* (UniProt ID A7LVG6) and the N-acetylneuraminate synthase NeuB from *N. meningitidis* (UniProt ID E0NCD4) and modified for growth on sucrose as described in Example 2 was further transformed with an expression plasmid containing a constitutive transcriptional unit for the N-acylneuraminate cytidylyltransferase neuA from *P. multocida* with SEQ ID NO:9 and for i) a sialyltransferase with SEQ ID NOs:1, 2, 3, 4, 5, 6, 7, 8, 11, or 12 or ii) an alpha-2,3-sialyltransferase from *N. meningitidis* with SEQ ID NO:14 acting as a reference K alpha-2,3-sialyltransferase or iii) an alpha-2,3-sialyltransferase from *N. gonorrhoeae* with SEQ ID NO:15 acting as a reference L alpha-2,3-sialyltransferase. The novel strains were evaluated in a growth experiment for production of 3'SL according to the culture conditions provided in Example 2, in which the strains were cultivated in minimal medium with 30 g/L sucrose and 20 g/L lactose. The strains were grown in four biological replicates in a 96-well plate. After 72h of incubation, the culture broth was harvested, and the sugars were analyzed on UPLC. For each strain with a particular sialyltransferase tested, the measured 3'SL concentration and maximum growth speed was averaged over all biological replicates and then normalized to the averaged 3'SL concentration or maximum growth speed of a reference K strain expressing an alpha-2,3-sialyltransferase from *N. meningitidis* with SEQ ID NO:14 or normalized to the averaged 3'SL concentration or maximum growth speed of a reference L strain expressing an alpha-2,3-sialyltransferase from *N. gonorrhoeae* with SEQ ID NO:15. The experiment showed all sialyltransferases were able to produce 3'SL. Surprisingly, and as demonstrated in Table 4, the sialyltransferases with SEQ ID NOs:1, 2, 3, 4, 5, 6, 7, 8, or 12 had a better 3-sialyltransferase binding activity on lactose than the reference K alpha-2,3-sialyltransferase from *N. meningitidis* with SEQ ID NO:14, and had a better 3-sialyltransferase binding activity on lactose than the reference L alpha-2,3-sialyltransferase from *N. gonorrhoeae* with SEQ ID NO:15. The experiment also showed that strains expressing a sialyltransferase with SEQ ID NOs:1, 2, 3, 4, 5, 6, 7, 8, or 12 had a higher maximum growth speed compared to the reference K strain expressing the reference K alpha-2,3-sialyltransferase from *N. meningitidis* with SEQ ID NO:14 and that strains expressing a sialyltransferase with SEQ ID NOs:1, 2, 3, 4, 5, 6, 7, 8, or 12 had a lower or equal maximum growth speed compared to the reference L strain expressing the reference L alpha-2,3-sialyltransferase from *N. gonorrhoeae* with SEQ ID NO:15 (Table 4).

TABLE 4

Relative production of 3'SL (%) in and relative maximum growth speed (%) of a modified *E. coli* strain expressing a sialyltransferase with SEQ ID NOs: 01, 02, 03, 04, 05, 06, 07, 08, 11 or 12 and compared to a reference strain K expressing an alpha-2,3-sialyltransferase from *N. meningitidis* with SEQ ID NO:14 or compared to a reference strain L expressing an alpha-2,3-sialyltransferase from *N. gonorrhoeae* with SEQ ID NO: 15, when evaluated in a growth experiment according to the culture conditions provided in Example 2, in which the culture medium contained 30 g/L sucrose and 20 g/L lactose.

| Strain | Sialyltransferase expressed | 3'SL (%) - ref K | mumax (%) - ref K | 3'SL (%) - ref L | mumax (%) - ref L |
|---|---|---|---|---|---|
| K | SEQ ID NO: 14 | 100 | 100 | 71 | 70 |
| L | SEQ ID NO: 15 | 142 | 144 | 100 | 100 |
| A | PmultST3-like polypeptide with SEQ ID NO: 11 consisting of amino acid residues 1 to 268 of UniProt ID Q9CLP3 | 129 | 105 | 91 | 73 |
| B | SEQ ID NO: 01 | 304 | 141 | 215 | 98 |
| C | SEQ ID NO: 02 | 283 | 143 | 200 | 100 |
| D | SEQ ID NO: 03 | 232 | 135 | 164 | 94 |
| E | SEQ ID NO: 04 | 357 | 143 | 252 | 99 |
| F | SEQ ID NO: 05 | 370 | 141 | 261 | 98 |
| G | SEQ ID NO: 06 | 388 | 132 | 274 | 92 |
| H | SEQ ID NO: 07 | 302 | 142 | 213 | 99 |
| I | SEQ ID NO: 08 | 264 | 138 | 187 | 96 |
| J | SEQ ID NO: 12 | 151 | 113 | 107 | 79 |

The invention claimed is:

1. A method of producing a 3'sialylated oligosaccharide, the method comprising:
contacting a sialyltransferase with a mixture comprising a donor comprising a sialic acid residue and an acceptor selected from an oligosaccharide or a disaccharide under conditions wherein the sialyltransferase catalyzes transfer of the sialic acid residue from the donor to the acceptor, thereby producing the 3'sialylated oligosaccharide,
wherein the sialyltransferase has α-2,3-sialyltransferase activity on the galactose (Gal) residue of lactose and comprises an amino acid sequence that has at least 80.0% amino acid sequence identity to the full-length amino acid sequence of SEQ ID NO: 5,
wherein the contacting occurs in a cell-free system or a cell that is heterologous to the sialyltransferase, and, optionally, separating the produced 3'sialylated oligosaccharide.

2. The method according to claim 1, wherein the sialyltransferase is within a cell extract and the cell extract is contacted with the mixture to produce the 3'sialylated oligosaccharide.

3. The method according to claim 1, wherein the 3'sialylated oligosaccharide is produced in a cell-free system.

4. A method of producing a 3'sialylated oligosaccharide, the method comprising:
i) providing a cell, heterologously expressing a sialyltransferase, wherein the sialyltransferase has α-2,3-sialyltransferase activity on the Gal residue of lactose and comprises an amino acid sequence that has at least 80.0% amino acid sequence identity to the full-length amino acid sequence of SEQ ID NO: 5,
ii) providing CMP-sialic acid, optionally wherein the CMP-sialic acid is produced by the cell,
iii) providing an oligosaccharide or disaccharide, optionally wherein the oligosaccharide or disaccharide is produced by the cell,
iv) cultivating and/or incubating the cell under conditions
a) permissive to express the sialyltransferase, optionally permissive to produce the CMP-sialic acid and/or the oligosaccharide or disaccharide, and
b) wherein the sialyltransferase catalyzes the transfer of a sialic acid residue from the CMP-sialic acid to an acceptor resulting in producing the 3'sialylated oligosaccharide, and
v) optionally, separating the 3'sialylated oligosaccharide from the cultivation or incubation.

5. The method according to claim 4, wherein the cell is a metabolically engineered cell.

6. The method according to claim 1, wherein the sialic acid residue is at least one selected from the group consisting of
Neu4Ac,
Neu5Ac,
Neu4,5Ac2,
Neu5,7Ac2,
Neu5,8Ac2,
Neu5,9Ac2,
Neu4,5,9Ac3,
Neu5,7,9Ac3,
Neu5,8,9Ac3,
Neu4,5,7,9Ac4,
Neu5,7,8,9Ac4,
Neu4,5,7,8,9Ac5,
Neu5Gc, and
2-keto-3-deoxymanno-octulonic acid (KDO).

7. The method according to claim 1, wherein the donor comprising a sialic acid residue is CMP-sialic acid.

8. The method according to claim 1, wherein the 3'sialylated oligosaccharide is 3'sialyllactose and the acceptor is lactose.

9. The method according to claim 1, wherein the 3'sialylated oligosaccharide is a saccharide modified with KDO and the acceptor is lactose.

10. The method according to claim 1, wherein the 3'sialylated oligosaccharide is a mixture of 3'sialyllactose and 3'KDO-lactose, and the acceptor is lactose.

11. The method according to claim 1, wherein the sialyltransferase comprises an amino acid sequence that has at least 90.0% amino acid sequence identity to the full-length amino acid sequence of SEQ ID NO: 5 or comprises the amino acid sequence of SEQ ID NO: 5.

12. The method according to claim 1, the method comprising:
  i) using a cultivation or incubation medium comprising at least one precursor and/or acceptor for producing the 3'sialylated oligosaccharide, and/or
  ii) adding to ae cultivation or incubation medium at least one precursor and/or acceptor feed for producing the 3'sialylated oligosaccharide,
  wherein, optionally, the precursor is selected from the group consisting of sialic acid, CMP-sialic acid, CMP-Neu5Ac, CMP-KDO, glucose, Gal and UDP-galactose.

13. The method according to claim 12, wherein the cultivation medium or incubation medium contains
  at least one carbon source selected from the group consisting of glucose, fructose, sucrose, and glycerol, and/or
  at least one compound selected from the group consisting of lactose, Gal, glucose, sialic acid, CMP-sialic acid, CMP-Neu5Ac, and CMP-KDO.

14. The method according to claim 12, further comprising:
  recovering the 3'sialylated oligosaccharide from the cultivation or incubation medium and/or the cell.

15. The method according to claim 1, wherein the method produces at least 45 g/L of a 3'sialylated oligosaccharide.

16. The method according to claim 1, wherein the method results in producing less than 10 g/L of 3'-KDO-lactose.

17. The method according to claim 1, wherein the method results in production of a saccharide mixture comprising at least 45 g/L of a 3'sialylated oligosaccharide, wherein the 3'sialylated oligosaccharide is not 3'KDO-lactose, and less than 10 g/L of a saccharide modified with KDO.

* * * * *